(12) United States Patent
Romanelli et al.

(10) Patent No.: US 11,395,796 B2
(45) Date of Patent: Jul. 26, 2022

(54) ANTI-CD37 IMMUNOCONJUGATE AND ANTI-CD20 ANTIBODY COMBINATIONS

(71) Applicant: Debiopharm International, S.A., Lausanne (CH)

(72) Inventors: Angela Romanelli, Lexington, MA (US); Rodrigo R. Ruiz-Soto, Boston, MA (US); Jose Ponte, Weymouth, MA (US); Jutta Deckert, Lexington, MA (US); Jan Pinkas, Belmont, MA (US)

(73) Assignee: Debiopharm International, S.A., Lausanne (CH)

( * ) Notice: Subject to any disclaimer, the term of this patent is extended or adjusted under 35 U.S.C. 154(b) by 600 days.

(21) Appl. No.: 16/170,160

(22) Filed: Oct. 25, 2018

(65) Prior Publication Data

US 2019/0183788 A1  Jun. 20, 2019

Related U.S. Application Data

(63) Continuation of application No. 15/171,732, filed on Jun. 2, 2016, now abandoned.
(Continued)

(51) Int. Cl.
*A61K 9/00* (2006.01)
*C07K 16/28* (2006.01)
*A61K 47/68* (2017.01)
*A61P 35/02* (2006.01)
*A61K 39/00* (2006.01)

(52) U.S. Cl.
CPC ........ *A61K 9/0019* (2013.01); *A61K 47/6801* (2017.08); *A61K 47/6803* (2017.08); *A61K 47/6849* (2017.08); *A61K 47/6867* (2017.08); *A61P 35/02* (2018.01); *C07K 16/2887* (2013.01); *C07K 16/2896* (2013.01); *A61K 2039/507* (2013.01); *A61K 2039/545* (2013.01); *C07K 2317/24* (2013.01)

(58) Field of Classification Search
None
See application file for complete search history.

(56) References Cited

U.S. PATENT DOCUMENTS

| 5,122,368 A | 6/1992 | Greenfield et al. |
| 5,595,756 A | 1/1997 | Bally |

(Continued)

FOREIGN PATENT DOCUMENTS

| CN | 1446104 A | 10/2003 |
| CN | 1494433 A | 5/2004 |

(Continued)

OTHER PUBLICATIONS

Smith et al., Blood Cells, Molecules, and Diseases, 2010, 45:317-323 (Year: 2010).*

(Continued)

*Primary Examiner* — Karl J Puttlitz
(74) *Attorney, Agent, or Firm* — Sterne, Kessler, Goldstein and Fox P.L.L.C.

(57) ABSTRACT

Methods of administering immunoconjugates that bind to CD37 (e.g., IMGN529) in combination with antibodies that bind to CD20 are provided. The methods comprise administering an anti-CD37 immunoconjugate (e.g., IMGN529) and an anti-CD20 antibody to a person in need thereof, for example, a cancer patient.

10 Claims, 18 Drawing Sheets

Specification includes a Sequence Listing.

A  DOHH2     B  SUDHL4     C  U2932

D  GRANTA-519     E  JVM2     F  Ramos

Related U.S. Application Data

(60) Provisional application No. 62/263,449, filed on Dec. 4, 2015, provisional application No. 62/172,672, filed on Jun. 8, 2015.

(56) References Cited

U.S. PATENT DOCUMENTS

| | | |
|---|---|---|
| 7,303,749 B1 | 12/2007 | Chari |
| 7,585,491 B2 | 9/2009 | Govindan |
| 7,601,354 B2 | 10/2009 | Chari |
| 7,989,598 B2 | 8/2011 | Steeves et al. |
| 8,088,387 B2 | 1/2012 | Steeves et al. |
| 8,765,917 B2 | 7/2014 | Deckert et al. |
| 9,346,887 B2 | 5/2016 | Deckert et al. |
| 9,447,189 B2 | 9/2016 | Deckert et al. |
| 10,202,460 B2 | 2/2019 | Deckert et al. |
| 10,556,958 B2 | 2/2020 | Deckert et al. |
| 11,104,740 B2 | 8/2021 | Deckert et al. |
| 2003/0114398 A1 | 6/2003 | Chatterjee et al. |
| 2004/0166115 A1 | 8/2004 | Griffiths et al. |
| 2005/0136049 A1 | 6/2005 | Ledbetter et al. |
| 2005/0287538 A1 | 12/2005 | Cheung et al. |
| 2006/0039913 A1 | 2/2006 | Das et al. |
| 2006/0233822 A1 | 10/2006 | Xia et al. |
| 2006/0263349 A1 | 11/2006 | McCutcheon et al. |
| 2007/0009519 A1 | 1/2007 | Hariharan et al. |
| 2007/0059306 A1* | 3/2007 | Grosmaire .............. A61P 35/00 424/144.1 |
| 2007/0237779 A1 | 11/2007 | Ledbetter et al. |
| 2007/0270585 A1 | 11/2007 | Chari et al. |
| 2008/0075726 A1 | 3/2008 | Smith et al. |
| 2008/0226626 A1 | 9/2008 | Hariharan et al. |
| 2008/0227198 A1 | 9/2008 | Hariharan et al. |
| 2008/0279850 A1 | 11/2008 | Brady et al. |
| 2009/0041783 A1 | 2/2009 | Takayama et al. |
| 2009/0136516 A1 | 5/2009 | Tedder et al. |
| 2009/0148447 A1 | 6/2009 | Ledbetter et al. |
| 2009/0175867 A1 | 7/2009 | Thompson et al. |
| 2009/0269336 A1 | 10/2009 | Hong et al. |
| 2009/0274692 A1 | 11/2009 | Tan et al. |
| 2009/0274713 A1 | 11/2009 | Chari et al. |
| 2010/0135900 A1 | 6/2010 | Cerveny et al. |
| 2010/0189722 A1 | 7/2010 | Heider et al. |
| 2010/0034820 A1 | 11/2010 | Ledbetter |
| 2011/0256056 A1 | 10/2011 | Alper |
| 2011/0256153 A1 | 10/2011 | Deckert et al. |
| 2012/0020963 A1 | 1/2012 | Banchereau |
| 2012/0020983 A9 | 1/2012 | Braun |
| 2012/0276119 A1* | 11/2012 | Deckert .................. A61P 27/02 424/172.1 |
| 2013/0058947 A1 | 3/2013 | Stull et al. |
| 2013/0295104 A1 | 11/2013 | Deckert et al. |
| 2014/0120083 A1 | 5/2014 | Stern et al. |
| 2014/0170063 A1 | 6/2014 | Govindan et al. |
| 2014/0348745 A1 | 11/2014 | Larsen et al. |
| 2015/0093397 A1 | 4/2015 | Carrigan |
| 2015/0343077 A1 | 12/2015 | Deckert et al. |
| 2016/0326258 A1 | 11/2016 | Deckert et al. |
| 2016/0340438 A1 | 11/2016 | Deckert et al. |
| 2017/0000900 A1 | 1/2017 | Romanelli |
| 2018/0244795 A1 | 8/2018 | Deckert |
| 2019/0218303 A1 | 7/2019 | Deckert et al. |
| 2020/0054763 A1 | 2/2020 | Bertoni et al. |
| 2020/0270361 A1 | 8/2020 | Deckert et al. |
| 2020/0330604 A1 | 10/2020 | Li et al. |
| 2021/0196835 A1 | 7/2021 | Rouits et al. |

FOREIGN PATENT DOCUMENTS

| | | |
|---|---|---|
| CN | 1568198 A | 1/2005 |
| EP | 0 328 147 B1 | 5/1994 |
| JP | 2006513203 A | 4/2006 |
| JP | 2013524777 A | 6/2013 |
| JP | 2016536298 A | 11/2016 |
| WO | WO 01/24763 A2 | 4/2001 |
| WO | WO 02/04021 A1 | 1/2002 |
| WO | WO 02/060484 A1 | 8/2002 |
| WO | WO 02/060485 A2 | 8/2002 |
| WO | WO 2002/102972 A2 | 12/2002 |
| WO | WO-03048306 A2 | 6/2003 |
| WO | WO 03/083069 A2 | 10/2003 |
| WO | WO-2004058298 A1 | 7/2004 |
| WO | WO 2005/017148 A1 | 2/2005 |
| WO | WO 2005/037989 A2 | 4/2005 |
| WO | WO 2005/037992 A2 | 4/2005 |
| WO | WO-2006074397 A2 | 7/2006 |
| WO | WO 2006/133450 A2 | 12/2006 |
| WO | WO 2007/014278 A2 | 2/2007 |
| WO | WO-2007077173 A1 | 7/2007 |
| WO | WO 2007/146968 A2 | 12/2007 |
| WO | WO-2007140371 A2 | 12/2007 |
| WO | WO 2008/052030 A2 | 5/2008 |
| WO | WO-2008119567 A2 | 10/2008 |
| WO | WO 2009/019312 A2 | 2/2009 |
| WO | WO 2009/065576 A1 | 5/2009 |
| WO | WO 2009/085576 A2 | 7/2009 |
| WO | WO 2009/126858 A2 | 10/2009 |
| WO | WO 2009/126944 A1 | 10/2009 |
| WO | WO 2009/134977 A1 | 11/2009 |
| WO | WO 2010/008726 A1 | 1/2010 |
| WO | WO 2010/009124 A2 | 1/2010 |
| WO | WO-2010126551 A1 | 11/2010 |
| WO | WO 2011/090754 A1 | 7/2011 |
| WO | WO 2011/090762 A1 | 7/2011 |
| WO | WO 2011/100398 A1 | 8/2011 |
| WO | WO 2011/100403 A1 | 8/2011 |
| WO | WO 2011/112978 A1 | 9/2011 |
| WO | WO 2012/135740 A2 | 10/2012 |
| WO | WO 2013/149171 A2 | 10/2013 |
| WO | WO 2013/171289 A1 | 11/2013 |
| WO | WO 2014/143807 A2 | 9/2014 |
| WO | WO 2014/195460 A1 | 12/2014 |
| WO | WO-2014197411 A | 12/2014 |
| WO | WO 2015/038777 A1 | 3/2015 |
| WO | WO-2015067586 A2 | 5/2015 |
| WO | WO 2015/116729 A2 | 8/2015 |
| WO | WO-2015175533 A2 | 11/2015 |
| WO | WO 2016/200676 A1 | 12/2016 |
| WO | WO 2017/040247 A1 | 3/2017 |
| WO | WO-2018083633 A1 | 5/2018 |
| WO | WO-2019229677 A1 | 12/2019 |

OTHER PUBLICATIONS

Tedoldi et al., Journal of Pathology, 2007, 213:429-440 (Year: 2007).*

Awan, F., et al., "Phase 1 Study of TRU-016, an Anti-CD37 SMIP Protein in Naive and Relapsed and/or Refractory CLL Patients," ASH Annual Meeting 642: Abstract #1792 poster, 1 page, United States (Nov. 2011). Accessed at: https://ash.confex.com/ash/2011/webprogram/Paper39421.html on Jul. 20, 2015.

Co, M.S., et al., "Chimeric and Humanized Antibodies With Specificity for the CD33 Antigen," Journal of immunology 148(4):1149-1154., American Association of Immunologists, United States (Feb. 1992).

Colman, P.M., "Effects of Amino Acid Sequence Changes on Antibody-Antigen Interactions," Research in Immunology 145(1):33-36, Elsevier, France (Jan. 1994).

Deckert, J., et al., "IMGN529, a Novel Antibody-Drug Conjugate (ADC) Targeting CD37 Shows Synergistic Activity with Rituximab in Non-Hodgkin Lymphoma (NHL) Models," Blood 126(23):1548, Abstract, 4 pages, American Society of Hematology, United States (Dec. 2015).

Deckert, et al., "Preclinical Mechanistic Studies Investigating Neutrophil and Lymphoid Cell Depletion by IMGN529, a CD37-Targeting Antibody-Drug Conjugate (ADC)," Abstract #3119, 2 pages, 57th ASH Annual Meeting and Exposition, Dec. 6-9, 2014, San Francisco, United States.

Deckert, J., et al., "IMGN529, a Novel Antibody-Drug Conjugate (ADC) Targeting CD37 Shows Synergistic Activity with Rituximab

(56) References Cited

OTHER PUBLICATIONS in Non-Hodgkin Lymphoma (NHL) Models," Blood 126(23):1548, poster, 1 page, American Society of Hematology, United States (Dec. 2015).
Gershoni, J.M., et al., "Epitope Mapping: the First Step in Developing Epitope-based Vaccines," BioDrugs 21(3):145-156, Springer International, New Zealand (2007).
Lai, K.C., et al., "The CD37-targeting ADC IMGN529 Combines the Potent Anti-cancer Activity of K7153A Antibody with Efficient Maytansinoid Delivery," American Association for Cancer Research Hosted by the European Organization for Research and Treatment of Cancer and the National Cancer Institute, Abstract #B209 Poster, 1 page, United States (Nov. 2011).
Paul, W.E., "Immunogenicity and Antigen Structure," in Fundamental Immunology, Third Edition, pp. 242, Raven Press, United States (1993).
Tutt, A., et al., "Trispecific F(ab')$_3$ Derivatives that use Cooperative Signaling via the TCR/CD3 Complex and CD2 to Activate and Redirect Resting Cytotoxic T Cells," The Journal of Immunology 147:60-69, The American Association of Immunologists, United States (Jul. 1991).
Wang, L., et al., "Structural Characterization of the Maytansinoid-Monoclonal Antibody Immunoconjugate, huN901-DM1, by mass spectrometry, " Protein Science, 14(9):2436-2446, Cold Spring Harbor Laboratory Press, United States (Sep. 2005).
Wang, Z., et al., "Universal PCR Amplification of Mouse Immunoglobulin Gene Variable Regions: the Design of Degenerate Primers and an Assessment of the Effect of DNA Polymerase 3' to 5' Exonuclease Activity," Journal of Immunological Methods 233(1-2):167-177, Elsevier, Netherlands (Jan. 2000).
Zenz, T., et al., "Exceptional in Vitro Activity of CD37 Antibodies in CLL," Blood 116(21):1021-1022, 2010 ASH Annual Meeting Abstracts (Abstract 2460), American Society of Hematology, United States (2010), accessed at https://ashconfex.com/ash/2010/webprogram/Paper29401.html, accessed on Apr. 4, 2016.
Zhao, X., et al., "CD37 is a Potential Therapeutic Target for B-Cell Non-Hodgkin Lymphoma," Blood, 116(21), Abstract #3098, p. 1, American Society of Hematology, United States (Nov. 2011); 52nd Annual Meeting of the American Society of Hematology (Ash); United States; Dec. 4-7, 2010 Accessed at https://ash.confex.com/ash/2010/webprogram/Paper28315.html, on Nov. 13, 2015.
Zhao, X., "Targeting CD37 and folate receptor for cancer therapy: strategies based on engineered proteins and liposomes," Ohio Link Electronic Theses & Dissertations Center, document No. osu1174678307, pp. 1-314, The Ohio State University, United States (2007). Accessed at https://etd.ohiolink.edu/ap/10?0::NO: 10:P10 ACCESSION_NUM:osu1174678307 on Oct. 2, 2015.
Heppner, G.H., et al., "Tumor heterogeneity: biological implications and therapeutic consequences," Cancer Metastasis Rev. 2(1):5-23, Martinus Nihoff Publishers, Netherlands (1983).
Jain, R.K., "Barriers to Drug Delivery in Solid Tumors," Scientific American 271(1):58-65, Scientific American Inc, United States (1994).
Angelisová, P., et al., "Association of four antigens of the tetraspans family (CD37, CD53, TAPA-1, and R2/C33) with MHC class II glycoproteins," Immunogenetics 39:249-256, Springer-Verlag, Germany (1994).
Bernstein, I.D., et al., "High Dose Radiolabeled Antibody Therapy of Lymphoma," Cancer Research (Suppl.) 50:1017s-1021s, American Association for Cancer Research, United States (1990).
Braslawsky, G.R., et al., "Antitumor Activity of Adriamycin (Hydrazone-linked) Immunoconjugates Compared with Free Adriamycin and Specificity of Tumor Cell Killing," Cancer Research 50:6608-6614, American Association for Cancer Research, United States (1990).
Deckert, J., et al., "IMGN529: A therapeutic maytansinoid conjugate of an anti-CD37 antibody with multiple mechanisms of action for B-cell lymphoma and leukemia," AACR Poster Abstract #2, Apr. 2-6, 2011.
Deckert, J., et al., "IMGN529: An Anti-CD37 Antibody-Maytansinoid Conjugate with Multiple Mechanisms of Actions for B-Cell Malignancies," Poster #306, Keystone Symphosis—B Cells: New Insights into Normal versus Dysregulated Function, Apr. 12-16, 2011, ImmunoGen, Inc., United States (2011).
Deckert, J., et al., "Potent B-Cell Depletion by IMGN529, a CD 37-Targeting Antibody-Maytansinoid Conjugate for the Treatment of B-Cell Malignancies," ASH Poster Abstract #3726:1-2 (2011).
Dijoseph, J.F., et al. "CD20-specific antibody-targeted chemotherapy of non-Hodgkin's B-cell lymphoma using calicheamicin-conjugated rituximab," Cancer Immunol Immunother 56:1107-1117, Springer-Verlag, Germany (2007).
Greenfield, R.S., et al., "Evaluation in Vitro of Adriamycin Immunoconjugates Synthesized Using an Acid-sensitive Hydrazone Linker," Cancer Research 50:6600-6607, American Association for Cancer Research, United States (1990).
International Search Report with Written Opinion for International Application No. PCT/US11/28172, International Searching Authority, United States, dated Jul. 13, 2011.
Kaminski, M.S., et al. "Imaging, Dosimetry, and Radioimmunotherapy With Iodine 131-Labeled Anti-CD37 Antibody in B-Cell Lymphoma," Journal of Clinical Oncology 10(11) :1696-1711, American Society of Clinical Oncology, United States (1992).
Knobeloch, K-P., et al., "Targeted Inactivation of the Tetraspanin CD37 Impairs T-Cell-Dependent B-Cell Response under Suboptimal Costimulatory Conditions," Molecular and Cellular Biology 20(15):5363-5369, American Society for Microbiology, United States (2000).
Lai, K.C., et al., "The CD37-targeting ADC IMGN529 combines the potent anti-cancer activity of K7153A antibody with efficient maytansinoid delivery," Poster Abstract #B209, AACR-EORTC-NCI 2011, ImmunoGen, Inc., United States (2011).
Lai, K.C., et al., "The CD37-targeting ADC IMGN529 combines the potent anti-cancer activity of K7153A antibody with efficient maytansinoid delivery," Oasis, The Online Abstract Submission System, Abstract 11-A-226-AACR:1-2, United States (2011).
Link, M.P., et al., "A Unique Antigen on Mature B Cells Defined by a Monoclonal Antibody," The Journal of Immunology 137(9):3013-3018, The American Association of Immunologists, United States (1986).
Maecker, H.T., et al., "The tetraspanin superfamily: molecular facilitators," FASEB J. 11:428-442, The Federation, United States (1997).
Meyer-Wentrup, F., et al., "Dectin-1 Interaction with Tetraspanin CD37 Inhibits IL-6 Production," The Journal of Immunology 178:154-162, The American Association of Immunologists, Inc., United States (2007).
Moore, K., et al., "Use of the Monoclonal Antibody WR17, Identifying the CD37 gp40-45 Kd Antigen Complex, in the Diagnosis of B-Lymphoid Malignancy," Journal of Pathology 152:13-21, John Wiley & Sons, Ltd., England (1987).
Park, P.U., et al., "Antibody and linker selection for the anti-CD37 antibody-maytansinoid conjugate IMGN529 for the treatment of B-cell malignancies," Experimental and Molecular Therapeutics session, Abstract #2830:1-24, AACR Annual Meeting 2011, ImmunoGen, Inc. (2011).
Pinkas, J., "Antibody Maytansinoid Conjugates for the Treatment of Cancer," Protein Therapeutics Forum 2012:1-23, ImmunoGen, Inc., United States (2012).
Polson, A.G., et al., "Antibody-Drug Conjugates for the Treatment of Non-Hodgkin's Lymphoma: Target and Linker-Drug Selection," Cancer Res 69(6):2358-2364, American Association for Cancer Research, United States (2009).
Press, O.W., et al., "Endocytosis and Degradation of Monoclonal Antibodies Targeting Human B-Cell Malignancies," Cancer Research 49:4906-4912, American Association for Cancer Research, United States (1989).
Press, O.W., et al., "Radiolabeled-Antibody Therapy of B-Cell Lymphoma with Autologous Bone Marrow Support," N Engl J Med 329(17):1219-1224, Massachusetts Medical Society, United States (1993).
Press, O.W., et al., "Retention of B-Cell-Specific Monoclonal Antibodies by Human Lymphoma Cells," Blood 83(5):1390-1397, The American Society of Hematology (1994).

(56) References Cited

OTHER PUBLICATIONS

Press, O.W., et al., "Treatment of Refractory Non-Hodgkin's Lymphoma With Radiolabeled MB-1 (Anti-CD37) Antibody," *J Clin Oncol* 7(8):1027-1038, American Society of Clinical Oncology, United States (1989).
Rops, A.L., et al., "The Tetraspanin CD37 Protects Against Glomerular IgA Deposition and Renal Pathology," *Am J Pathol* 176:2188-2197, American Society for Investigative Pathology (2010).
Schwartz-Albiez, R., et al., "The B Cell-Associated CD37 Antigen (gp40-52): Structure and Subcellular Expression of an Extensively Glycosylated Glycoprotein," *The Journal of Immunology* 140(3):905-914, The American Association of Immunologists, United States (1988).
Sheng, K-C., et al., "Tetraspanins CD37 and CD151 differentially regulate Ag presentation and T-cell co-stimulation by DC," *Eur. J. Immunol.* 39:50-55, Wiley-VCH Verlag GmbH & Co. KGaA, Germany (2009).
Van Spriel, A.B., et al., "A Regulatory Role for CD37 in T Cell Proliferation," *The Journal of Immunology* 172:2953-2961, The American Association of Immunologists, United States (2004).
Van Spriel, A.B., et al., "The Tetraspanin Protein CD37 Regulates IgA Responses and Anti-Fungal Immunity," *PLoS Pathogens* 5(3) e1000338:1-11, Public Library of Science, United States (2009).
Tedder, T.F., et al., "Structure of the Gene Encoding the Human B Lymphocyte Differentiation Antigen CD20 (Bl)," *The Journal of Immunology* 142(7):2560-2568, The American Association of Immunologists, United States (1989).
Zhao, X., et al., "Targeting CD37-positive lymphoid malignancies with a novel engineered small modular immunopharmaceutical," *Blood* 110(7):2569-2577, The American Society of Hematology, United States (2007).
Awan, F., et al., "Phase 1 Study of TRU-016, an Anti-CD37 SMIP Protein in Naïve and Relapsed and/or Refractory CLL Patients," Poster (2011).
Awan, F.T, et al., "Phase 1 Study of TRU-016, an Anti-CD37 SMIP™ Protein in Naïve and Relapsed and/or Refractory CLL Patients," *Blood (ASH Annual Meeting Abstracts)* 2011 118:Abstract 1792 (2011).
Barrena, S., et al., "Aberrant expression of tetraspanin molecules in B-cell chronic lymphoproliferative disorders and its correlation with normal B-cell maturation," *Leukemia* 19:1376-1383, Nature Publishing Group, England (2005).
Blanc, V., et al., "SAR3419: An Anti-CD19-Maytansinoid Immunoconjugate for the Treatment of B-Cell Malignancies," *Clin Cancer Res* 17(20):6448-6458, American Association for Cancer Research, United States (2011).
Heider, K-H., et al., "A novel Fc-engineered monoclonal antibody to CD37 with enhanced ADCC and high proapoptotic activity for treatment of B-cell malignancies," *Blood* 118(15):4159-4168, The American Society of Hematology, United States (2011).
Lambert, J.M., "Antibody-Maytansinoid Conjugates: A New Strategy for the Treatment of Cancer," *Drugs of the Future* 35(6):471-480, Prous Science, S.A.U., Spain (2010).
Pagel, J.M, et al., "Phase 1 Study of TRU-016, An Anti-CD37 SMIP™ Protein in Relapsed and/or Refractory NHL Patients," *Blood (ASH Annual Meeting Abstracts) 2011* 118(21):Abstract 1636 (2011).
Roguska, M.A., et al., "A comparison of two murine monoclonal antibodies humanized by CDR-grafting and variable domain resurfacing," *Protein Engineering* 9(10):895-904, Oxford University Press, England (1996).
Roguska, M.A., et al., "Humanization of murine monoclonal antibodies through variable domain resurfacing," *Proc. Natl. Acad. Sci. USA* 91:969-973, National Academy of Sciences, United States (1994).
Teicher, B.A. and Chari, R.V.J., "Antibody Conjugate Therapeutics: Challenges and Potential," *Clin Cancer Res* 17(20):6389-6397, American Association for Cancer Research, United States (2011).
Dahle, J., et al., "Evaluating Antigen Targeting and Anti-tumor Activity of a New Anti-CD37 Radioimmunoconjugate Against Non-Hodgkin's Lymphoma," *Anticancer Research* 33:85-96, International Institute of Anticancer Research, Greece (2013).
Lapalombella, R., et al., "Tetraspanin CD37 Directly Mediates Transduction of Survival and Apoptotic Signals," *Cancer Cell* 21:694-708, Elsevier Inc., United States (2012).
Zhao, X.B., et al., "Novel Anti-CD37 Small Modular Immunopharmaceutical (SMP) Induces B-Cell-Specific, Caspase-Independent Apoptosis in Human CLIJ Cells," *Blood 104*, Abstract 2515, ASII Annual Meeting, American Society of Hematology, United States (2004).
International Search Report and Written Opinion for International Patent Appl. No. PCT/US12/31648 dated Sep. 20, 2012, Commissioner for Patents, United States.
Preissuance Submission by Third Party under 37 C.F.R. § 1.290, filed in U.S. Appl. No. 13/045,693, filed Mar. 11, 2011.
Kovtun, Y., et al. "Antibody-Maytansinoid Conjugates Designed to Bypass Multidrug Resistance," *Cancer Research* 70(6):2528-2537, American Association for Cancer Research, United States (Mar. 2010).
Cragg, M.S., et al.," Complement-mediated lysis by anti-CD20 mAb correlates with segregation into lipid rafts," *Blood* 101(3):1045-1052, American Society of Hematology, United States (2003).
Business Wire, "ImmunoGen, Inc. Announces Presentations at the 102$^{nd}$ Annual Meeting of the American Associated for Cancer Research," May 30, 2011, accessed at http://files.shareholder.comjdownloads/ABEA-5VU3S1/0x0x500536/b6f7f6a6-1853-4476-93cf-2f2f895241d7/IMGN News_2011_3_30_General_Releases.pdf, accessed on Dec. 8, 2014.
Beckwith, K.A., et al.,"The CD37-targeted antibody-drug conjugate IMGN529 is highly active against human CLL and in a novel CD37 transgenic murine leukemia model," *Leukemia* 28(7):1501-1510, Nature Publishing Group, England (Jul. 2014).
Yu, B., et al., "Targeted drug delivery and cross-linking induced apoptosis with anti-CD37 based dual-ligand immunoliposomes in B chronic lymphocytic leukemia cells," Biomaterials 34(26):6185-6193, Elsevier Science, Netherlands (2013).
Deckert, J., et al., "A novel anti-CD37 antibody-drug conjugate with multiple anti-tumor mechanisms for the treatment of B-cell malignancies," *Blood* 122(20):3500-3510 American Society of Hematology, United States (2013).
Harris, C.L., et al., "Tumour cell killing using chemically engineered antibody constructs specific for tumour cells and the complement inhibitor CD59," *Clinical & Experimental Immunology* 107(2):364-371, Blackwell Publishing, England (2003).
Altschuler, E.P., et al., "Method for obtaining recombinant antibodies and for improving affinities thereof", *Uspehi biologicheskoi himii 50*: 203-258, Pleiades Publishing Ltd., Russia (Dec. 2010).
Altschuler, E.P., et al., "Generation of Recombinant Antibodies and Means for Increasing Their Affinity," *Biochemistry (Moscow)* 75(13): 1584-1605, Pleiades Publishing, Ltd., Russia (Dec. 2010).
Zhao, X., "Targeting CD37 and folate receptor for cancer therapy: strategies based on engineered proteins and liposomes," Europe PubMed Central, accessed at http://europepmc.org/theses/ETH/6183, accessed on Dec. 9, 2014 (2007) [Thesis 6183].
Preissuance Submission by Third Party under 37 C.F.R. § 1.290, filed in U.S. Appl. No. 13/796,768, filed Mar. 12, 2013.
Preissuance Submission by Third Party under 37 C.F.R. § 1.290, filed in U.S. Appl. No. 13/436,528, filed Mar. 30, 2012.
De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," Journal of Immunology 169(6):3076-3084, The American Association of Immunologists, United States (2002).
International Preliminary Report on Patentability for International Application No. PCT/US2012/031648, The International Bureau of WIPO, Switzerland, dated Oct. 2, 2013, pp. 1-9.
International Search Report and Written Opinion for International Application No. PCT/US2013/034646, Commissioner for Patents, United States, dated Sep. 16, 2013, pp. 1-15.
Maccallum, R.M., et al., "Antibody-Antigen Interactions: Contact Analysis and Binding Site Topography," Journal of Molecular Biology 262(5):732-745, Elsevier, England (1996).

(56) References Cited

OTHER PUBLICATIONS

Supplementary European Search Report for Application No. EP11754195, dated Sep. 10, 2013, pp. 1-7.
Zhao, X.B., et al., "Novel Anti-CD37 Small Modular Immunopharmaceutical (SMIP) Induces B- Cell-Specific, Caspase-Independent Apoptosis in Human CLL Cells," Blood 104, Abstract 2515, p. 1, ASII Annual Meeting, American Society of Hematology, United States (2004). Accessed at http://abstracts.hematologylibrary.org/cgi/content/short/104/11/2515 on Jul. 16, 2015.
Zhao Xiaoxian et al: "CD37 is a Potential Therapeutic Target for B-Cell Non-Hodgkin Lymphoma.", Blood, 116(21), pp. 1277-1278, American Society of Hematology, United States (Nov. 2011); 52nd Annual Meeting of The American-Society-of Hematology(Ash); Orlando, FL, USA; Dec. 4-7, 2010 Accessed at https://ash.confex.com/ash/2010/webprogram/Paper28315.html, on Nov. 13, 2015.
Extended European Search Report and written opinion for EP Application No. 13 77 0074, The Hague, The Netherlands, completed on Oct. 20, 2015, pp. 1-9.
International Search Report and Written Opinion for International Application No. PCT/US15/30371, Commissioner for Patents, United States, dated Nov. 2, 2015, pp. 1-10.
Robak T. et al., "TRU-016, A humanized anti-CD37 IgG fusion protein for the potential treatment of B-cell malignancies", Curr Opin Investig Drugs. 2009. V.10. No. 12, p. 1383-1390, Current Drugs Ltd. England (2009).
Office Action dated Aug. 11, 2015 in Russian Patent Application No. 2012139045/10 (063108), filed Mar. 11, 2011, Applicant: Immunogen, Inc., US.
Morris, G.E., "Epitope Mapping of Protein Antigens by Competition Elisa," *The Protein Protocols Handbook 1*:595-600, Humana Press, United States (1996).
Marken, J., et al., "Membrane Topology of the L6 Antigen and Identification of the Protein Epitope Recognized by the L6 Monoclonal Antibody," *Journal of Biological Chemistry 269*: 7397-401, The American Society for Biochemistry and Molecular Biology, Inc., United States (1994).
International Search Report and Written Opinion for International Application No. PCT/US2016/048887, Commissioner for Patents, United States, dated Nov. 29, 2016, pp. 1-8.
International Search Report and Written Opinion for International Application No. PCT/US16/035558, Commissioner for Patents, United States, dated Sep. 7, 2016, pp. 1-11.
Beers, S.A., et al., "Type II (Tositumomab) Anti-CD20 Monoclonal Antibody Out Performs Type I (Rituximab-Like) Reagents in B-Cell Depletion Regardless of Complement Activation," *Blood 112*(10)4170-4177, American Society of Hematology, United States (2008).
Bissery, M., et al., "Experimental Antitumor Activity of Taxotere (RP 56976, NSC 628503), a Taxol Analogue," *Cancer Research 51*(18):4845-4852, American Association for Cancer Research, United States (1991).
Boross, P. and Leusen, J.H., "Mechanisms of Action of CD20 Antibodies," *American Journal of Cancer Research 2*(6):676-690, e-Century Publishing Corporation, United States (2012).
Cheson, B.D., et al., "Revised Response Criteria for Malignant Lymphoma," *Journal of Clinical Oncology 25*(5):579-586, American Society of Clinical Oncology, United States (2007).
Friedberg, J.W., "Double-Hit Diffuse Large B-cell Lymphoma," *Journal of Clinical Oncology 30*(28):3439-3443, American Society of Clinical Oncology, United States (2012).
Green, T.M., et al., "Immunohistochemical Double-Hit Score is a Strong Predictor of Outcome in Patients with Diffuse Large B-cell Lymphoma Treated with Rituximab Plus Cyclophosphamide, Doxorubicin, Vincristine, and Prednisone," *Journal of Clinical Oncology 30*(28):3460-3467, American Society of Clinical Oncology, United States (2012).
Hu, S., et al., "MYC/BCL2 Protein Coexpression Contributes to the Inferior Survival of Activated B-Cell Subtype of Diffuse Large B-Cell Lymphoma and Demonstrates High-Risk Gene Expression Signatures: a Report from The International DLBCL Rituximab-CHOP Consortium Program," *Blood 121*(20)4021-4031, American Society of Hematology, United States (2013).
Lai, K.C., et al., "Evaluation of Targets for Maytansinoid ADC Therapy Using a Novel Radiochemical Assay," *Pharmaceutical Research 32*(11):3593-3603, Kluwer Academic, United States (Nov. 2015).
Lim, S.H., et al., "Anti-CD20 Monoclonal Antibodies: Historical and Future Perspectives," *Haematologica 95*(1)135-143, Ferrata Storti Foundation, Italy (2010).
Pers, J.O., et al., "Anti-CD20 Antibody-Mediated Apoptosis of B Cells is a Lipid Raft-Dependent Process," *Annals of the Rheumatic Diseases 70*(*Suppl 2*): A73, BMJ Publishing Group Ltd (2011).
Robak, T. and Robak, E., "New Anti-CD20 Monoclonal Antibodies for the Treatment of B-cell Lymphoid Malignancies," *BioDrugs 25*(1):13-25, Springer International, New Zealand (2011).
Tomayko. M.M. and Reynolds, C.P., "Determination of Subcutaneous Tumor Size in Athymic (Nude) Mice," *Cancer Chemotherapy and Pharmacology 24*(3):148-154, Springer Verlag, Germany (1989).
Smith et al., "2006 update of recommendations for the use of white blood cell growth factors: an evidence-based clinical practice guideline," *J. Clin. Oncol.* 24: 3187-3205, American Society of Clinical Oncology, United States (2006).
Romanelli, A., et al., Novel CD37-Targeting Antibody-Drug Conjugate (ADC), IMGN529, Has Synergistic Activity in Combination with Rituximab in Non-Hodgkin Lymphoma (NHL) Models, presented at 13th International Conference on Malignant Lymphoma, Jun. 17-20, 2015, 1 page.
Deckert, et al., IMGN529, a Novel Antibody-Drug Conjugate (ADC) Targeting CD37 Shows Synergistic Activity with Rituximab in Non-Hodgkin Lymphoma (NHL) Models, poster # 1548, 1 page, 57th ASH Annual Meeting and Exposition, Dec. 5, 2015, Orlando, United States.
Angeletti, R.H., "Design of Useful Peptide Antigens," *Journal of Biomolecular Techniques 10*(1):2-10, Association of Biomolecular Resource Facilities, United States (1999).
Daniel, C., et al., "Mapping of Linear Antigenic Sites on the S Glycoprotein of a Neurotropic Murine Coronavirus with Synthetic Peptides: A combination of Nine Prediction Algorithms Fails to Identify Relevant Epitopes and Peptide Immunogenicity is Drastically Influenced by the Nature of the Protein Carrier," *Virology 202*: 540-549, Elsevier, Netherlands (1994).
Greenspan, N.S., et al., "Defining epitopes: It's not as easy as it seems," *Nature Biotechnology* . 17:936-937, Nature America Inc., United States (1999).
Gussow, D., et al., "Humanization of Monoclonal Antibodies," *Methods in Enzymology 203*:99-121, Elsevier, Netherlands (1991).
Lippincott-Schwartz (Current Protocols in Cell Biology) pp. 16.0.1-16.0.2, (2002).
Mariuzza, R.A., et al., "The Structural Basis of Antigen-Antibody Recognition," *Ann. Rev. Biophys. Chem 16*:139-159, Annual Reviews, United States (1987).
Rudikoff, S., et al., "Single Amino Acid Substitution Altering Antigen-Binding Specificity," *Proc. Natl. Acad. Sci. 79*:1979-1983, United States National Academy of Sciences,United States (1982).
Office Action dated Apr. 28, 2017 in U.S. Appl. No. 15/130,667, inventors Deckert, J., et al., filed Apr. 15, 2016, 15 pages.
Office Action dated Oct. 31, 2017 in U.S. Appl. No. 15/130,667, inventors Deckert, J., et al., filed Apr. 15, 2016, 19 pages.
International Search Report with Written Opinion for International Application No. PCT/IB2017/056841, International Searching Authority, Netherlands, dated Feb. 2, 2018, 14 pages.
International Preliminary Report on Patentability for International Application No. PCT/US16/035558, International Search Authority, Switzerland, dated Dec. 12, 2017, 8 pages.
Stathis, A., et al., "Safety, tolerability, and preliminary activity of IMGN529, a CD37-targeted antibody-drug conjugate, in patients with relapsed or refractory B-cell non-Hodgkin lymphoma: a dose-escalation phase I study," *Invest. New Drugs* e-pub Feb. 17, 2018 (https://doi.org/10.1007/s10637-018-0570-4), Springer US, United States (2018).
Smith, S.M., et al., "The Impact of MYC expression in lymphoma biology: Beyond Burkitt lymphoma," Blood Cells, Molecules, and Diseases 45:317-323, Elsevier, Netherlands (2010).

(56) References Cited

OTHER PUBLICATIONS

Tedoldi, S., et al., "Selective Loss of B-cell phenotype in lymphocyte predominant Hodgkin lymphoma," Journal of Pathology 213:429-440, Wiley Interscience, United States (2007).
Office Action dated May 29, 2018, in U.S. Appl. No. 15/171,732, inventors Romanelli, A.., et al., filed Jun. 2, 2016, 29 pages.
Office Action dated Oct. 25, 2017, in U.S. Appl. No. 15/171,732, inventors Romanelli, A.., et al., filed Jun. 2, 2016, 24 pages.
Ackler, S., et al., "The Bcl-2 inhibitor ABT-263 enhances the response of multiple chemotherapeutic regimens in hematologic tumors in vivo," Cancer Chemother Pharmacol 66(5):869-880, Springer Science+Business Media, United States (2010).
Alley, S.C., et al., "Antibody-drug conjugates: targeted drug delivery for cancer." Current Opinion Chem Biol 14:529-537, Elsevier, Netherlands (2010).
Clinical Trials.gov Archive, "NCT01534715; IMGN529 in Treating Patients with Relapsed or Refractory Non-Hodgkin's Lymphoma," accessed at https://clinicaltrails.gov/archive/NCT01534715/2012_02_16, last accessed Sep. 9, 2016, 2 pages.
Deckert, J., et al., "Preclinical Mechanistic Studies Investigating Neutrophil and Lymphoid Cell Depletion by IMGN529, a CD37-Targeting Antibody-Drug Conjugate (ADC)," 56th ASH Annual Meeting and Exposition: Abstract# 3119, pp. 1-2, United States (Dec. 2014) Accessed at https://ash.confex.com/ash/2014/webprogram/Paper70777.html on Aug. 26, 2015.
Deckert, J., et al., "Preclinical Mechanistic Studies Investigating Neutrophil and Lymphoid Cell Depletion by IMGN529, a CD37-Targeting Antibody-Drug Conjugate (ADC)," 56th ASH Annual Meeting and Exposition: Poster, Abstract# 3119, p. 1, United States (Dec. 2014) Accessed at http://www.immunogen.com/documents/Publications/IMGN529%20preclinical%20ASH%2012-2014.pdf on Aug. 26, 2015.
Eugenio, G., et al., Identification of anti-lymphoma biomarkers of response to the anti-cd37 antibody dmg conjugate (ADC) IMGN529, presented at 58$^{th}$ Annual Meeting and Exposition of the American Society of Hematology 128, 1 page. (2016).
Epstein, A.L., et al., "Two New Monoclonal Antibodies, Lym-1 and Lym-2, Reactive With Human B-Lymphocytes and Derived Tumors, with Immunodiagnostic and Immunotherapeutic Potential," Cancer Research 47:830-840, American Association for Cancer Research, United States (1987).
Hicks, S.W., et al., "The Antitumor Activity of IMGN529, a CD37-Targeting Antibody-Drug Conjugate, is Potentiated by Rituximab in Non-Hodgkin Lymphoma Models," Neoplasia 19(9):661 -671, Elsevier, Netherlands (Sep. 2017).
Konig, A., et al., "Basic fibroblast growth factor (bFGF) upregulates the expression of bcl-2 in B cell chronic lymphocytic leukemia cell lines resulting in delaying apoptosis," Leukemia 11:258-265, Nature Publishing Group, United States (1997).
Rudolph,C., et al., "Molecular Cytogenetic Characterization of the Mantle Cell Lymphoma cell line GRANTA-519," Cancer Genetics and Cytogenetics 153:144-150, Elsevier, Netherlands (2004).
Sloss, C.M., et al., "IMGN529, a novel Antibody-Drug Conjugate (ADC) targeting CD37, Shows Synergistic Activity with Rituximab in Non-Hodgkin Lymphoma (NHL) Models," Abstract 1548, presented at American Society of Hematology, Dec. 5, 2015, 1 page.
Stathis, A. et al., "Preliminary Findings from a Phase I, Multicenter, Open-label Study of the anti-CD37 Antibody-Drug Conjugate (ADC), IMGN529, in Adult Patients with Relapsed or Refractory Non-Hodgkin Lymphoma (NHL)," 2014 ASCO Annual Meeting, Poster, Abstract No. 8526, p. 1, United States (May 2014), Accessed at http://www.immunogen.com/documents/Publications/IMGN529%20first%20clin%ASCO%202014.pdf on Aug. 26, 2015.
Stathis, A. et al., "A Phase I Study of IMGN529, an Antibody-Drug Conjugate (ADC) Targeting CD37, in Adult Patients With Relapsed or Refractory Non-Hodgkin Lymphoma (NHL)," 56th ASH Annual Meeting and Exposition: Abstract#1760, pp. 1-2, United States (Dec. 2014), Accessed at https://ash.confex.com/ash/2014/webprogram/Paper70219.html, on Aug. 26, 2015.
Stathis, A. et al., "A Phase I Study of IMGN529, an Antibody-Drug Conjugate (ADC) Targeting CD37, in Adult Patients With Relapsed or Refractory Non-Hodgkin Lymphoma (NHL)," 56th ASH Annual Meeting and Exposition: Poster, Abstract#1760, p. 1, United States (Dec. 2014) accessed at http://www.immunogen.com/documents/Publications/IMGN529_PhI_ASH12-2014.pdf, accessed on Aug. 26, 2015.
Smolewski, P., et al., "Pro-Apoptotic effect of an anti-CD37 scFv-Fc fusion protein, in combination with the anti-CD20 antibody, of atumumab, on tumor cells from B-cell malignancies," European Journal of Cancer 50(15):2677-2684, Elsevier, Netherlands (2014).
Gross, J., "3333:Evaluation of Otlertuzumab (TRU-016), an Anti-CD37 Adaptir™ Therapeutic in Preclinical Combination Studies with Kinase Inhibitors and a Next Geemation Anti-CD20 Mab in Vitro and in Animal Models of Non-Hodgkin's Lymphoma," Blood 124(21):3333, American Society of Hematology, United States (2014).
Gopal, A., et al., "Phase 1b Study of otlertuzumab (TRU-016), an anti-CD37 monospecific Adaptir™ therapeutic protein, in Combination with Rituximab and Bendamustine in Relapsed Indolent Lymphoma patients," Investigational New Drugs Presented at ASH annual meeting, Nov. 2012, 13 pages.
Algate, P., et al., "TRU-016, an Anti-CD37 SMIP (TM) Biologic, in combination with Other Therapeutic Drugs in Models of Non-Hodgkin's Lymphoma," Blood 116(21):1603, Abstract #3931 American Society of Hematology, United States (Nov. 2010), 5 pages.
Deckert, J., et al., "IMGN529, a Novel Antibody-Drug Conjugate (ADC) Targeting CD37 Shows Synergistic Activity with Rituximab in Non-Hodgkin Lymphoma (NHL) Models," Blood 126(23), 5 pages, American Society of Hematology, United States (Dec. 2015).
Chen, R., et al., "A Phase II study of vorinostat and rituximab for treatment of newly diagnosed and relapsed/refractory indolent non-Hodgkin lymphoma," Haematologica 100(3):357-362, Ferrata Storti Foundation, Italy (Mar. 2015).
Oki, Y., et al., "Pegylated liposomal doxorubicin replacing conventional doxorubicin in standard R-CHOP chemotherapy for elderly patients with diffuse large B-cell lymphoma: an open label, single arm, phase II trial," Clinical Lymphoma, Myeloma & Leukemia 15(3):152-158, Elsevier, Netherlands (Mar. 2015).
Ducry, L., et al., "Antibody-Drug Conjugates: Linking Cytotoxic Payloads to Monoclonal Antibodies," Bioconjugate 21:5-13, American Chemical Society, United States (2009).
Written Opinion for Singapore Patent Application No. 10201501803Y, dated Sep. 4, 2018, Intellectual Property Office of Singapore, Singapore, 6 pages.
Goel, M., et al., "Plasticity within the Antigen-Combining Site May Manifest as Molecular Mimicry in the Humoral Immune Response," J. Immunol 173:7358-7367, American Association of immunologists, United States (2004).
Khan, T., et al., "Adjustable Locks and Flexible Keys: Plasticity of Epitope-Paratope Interactions in germline Antibodies," J Immunol. 192:5398-5405, American Association of immunologists, United States (2014).
Poosarla, V., et al., "Computational De Novo Design of Antibodies Binding to a Peptide with High Affinity," Biotechnology and Bioengineering 114(6):1331-1342, Wiley Periodicals, United States (2007).
Office action dated Jul. 2, 2018, U.S. Appl. No. 15/233,423, inventors Deckert, J., et al., filed Aug. 10, 2016, 9 pages.
Epsitein, A.L., et al., "Two New Monoclonal Antibodies (LN-1, LN-2) reactive in B5 formalin-fixed paraffin-embedded tissues with follicular center and mantle zone human B lymphocytes and derived tumors." J. Immunol 133:1028-1036, American Association of Immunologists, United States (1984).
International Preliminary Report on Patentability for International Application No. PCT/US2016/048887, International Searching Authority, United States, dated Nov. 29, 2016, 5 pages.
Barthelemy P.A., et al., "Comprehensive Analysis of the Factors Contributing to the Stability and Solubility of Autonomous Human VH Domains," The Journal of Biological Chemistry 283, 3639-3654, American Society for Biochemistry and Molecular Biology (Feb. 2008).

(56) References Cited

OTHER PUBLICATIONS

Beiboer, S.H., et al., "Guided Selection of a Pan Carcinoma Specific Antibody Reveals Similar Binding Characteristics yet Structural Divergence between the Original Murine Antibody and its Human Equivalent," Journal of Molecular Biology 296(3):833-849, Elsevier, England (Feb. 2000).

Choi Y, and Deane C.M., "Predicting Antibody Complementarity Determining Region Structures Without Classification," Molecular BioSystems 7:3327-3334, The Royal Society of Chemistry (Sep. 2011).

De Genst, E., et al., "Antibody Repertoire Development in Camelids," Developmental and Comparative Immunology 30(1-2):187-198, Elsevier Science, United States (2006).

Griffiths, A.D., et al., "Human Anti-Self Antibodies with High Specificity from Phage Display Libraries," The EMBO Journal 12(2):725-734, Wiley Blackwell, England (Feb. 1993).

International Search Report and Written Opinion dated Aug. 21, 2019, in International Application No. PCT/IB2019/054457, EPO, Netherlands, 11 pages.

Klimka, A., et al., "Human Anti-CD30 Recombinant Antibodies by Guided Phage Antibody Selection Using Cell Panning," British Journal of Cancer 83(2):252-260, Nature Publishing Group, England (Jul. 2000).

Levy, M.Y., et al., "Safety and efficacy of CD37-Targeting Naratuximab Emtansine plus Rituximab in Diffuse Large B-cell Lymphoma and Other Non-Hodgkin's B-cell Lymphomas—a Phase 2 Study," Poster #244, presented at the 16th International Conference on Malignant Lymphoma (Virtual Edition), Debiopharm International S.A., Switzerland, accessed at URL:[https://www.debiopharm.com/drug-development/publications/safety-and-efficacy-of-cd37-targeting-naratuximab-emtansine-plus-rituximab-in-diffuse-large-b-cell-lymphoma-and-other-non-hodgkins-b-cell-lymphomas-a-phase-2-study/] on Jul. 16, 2021, 1 page (Jun. 2021).

Malia, T.J., et al., "Epitope Mapping and Structural Basis for the Recognition of Phosphorylated Tau by the Anti-tau Antibody AT8," Proteins 84(4):427-434, Wiley-Liss, United States (Apr. 2016).

Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).

Prescribing Information, "Rituxan," retrieved from: https://www.gene.com/download/pdf/rituxan_prescribing.pdf, 53 pages. Initial U.S. Approval: 1997. Last updated Jun. 2021.

Office action dated Aug. 3, 2021, in U.S. Appl. No. 16/221,747, inventors Deckert, et al., filed Dec. 17, 2018, 13 pages.

Office action dated May 16, 2018, in U.S. Appl. No. 15/130,667, inventors Deckert, et al., filed Apr. 15, 2016, 6 pages.

Office action dated Sep. 3, 2015, in U.S. Appl. No. 13/796,768, inventors Deckert, et al., filed Mar. 12, 2013, 11 pages.

Office action dated Dec. 11, 2015, in U.S. Appl. No. 13/796,768, inventors Deckert, et al., filed Mar. 12, 2013, 8 pages.

\* cited by examiner

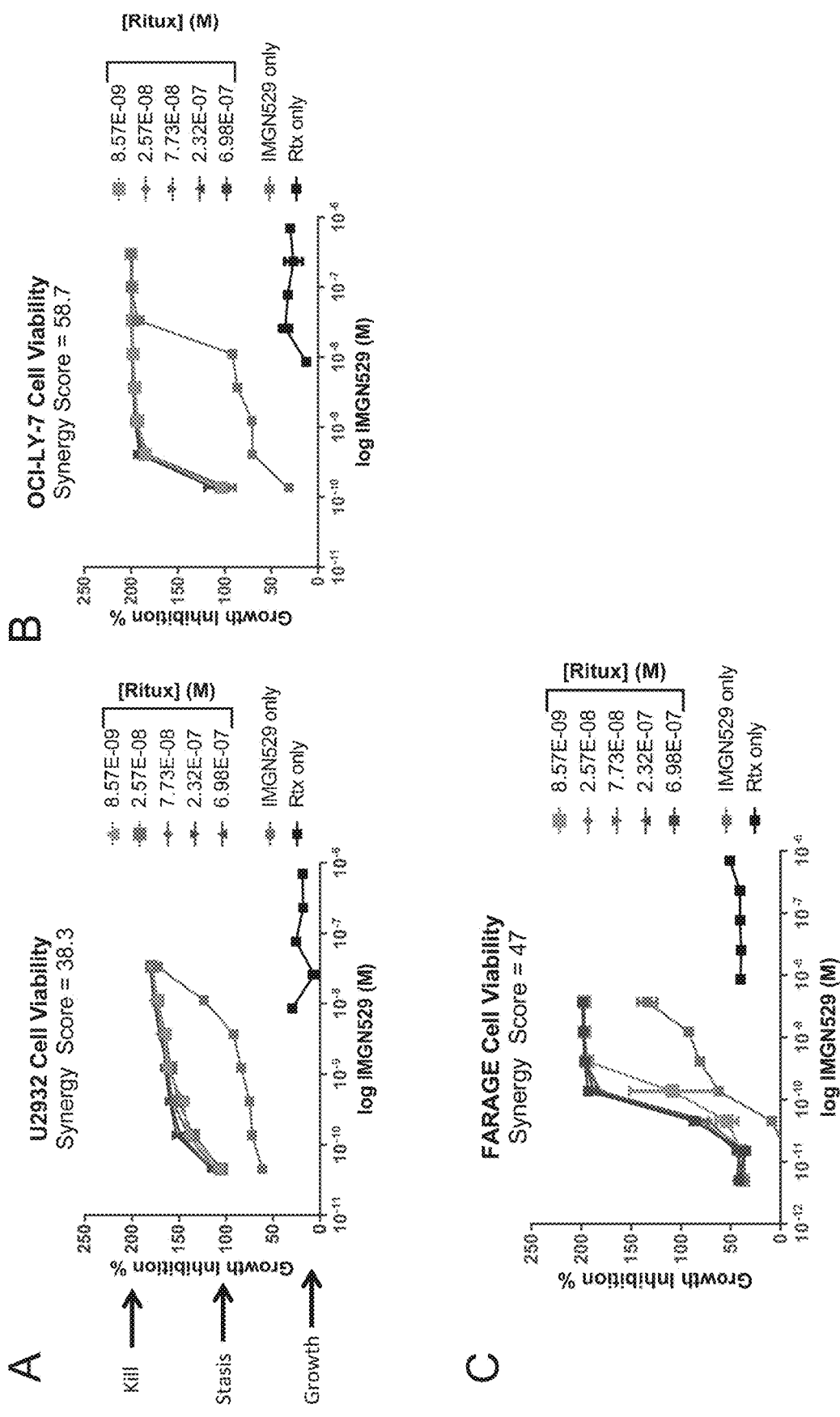

SEQUENCE LISTING

```
<160> NUMBER OF SEQ ID NOS: 37

<210> SEQ ID NO 1
<211> LENGTH: 280
<212> TYPE: PRT
<213> ORGANISM: homo sapiens

<400> SEQUENCE: 1

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110
```

Ala Gln Leu Glu Arg Ser Leu Arg Asp Val Val Glu Lys Thr Ile Gln
            115                 120                 125

Lys Tyr Gly Thr Asn Pro Glu Glu Thr Ala Ala Glu Glu Ser Trp Asp
        130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Tyr Arg
        275                 280

<210> SEQ ID NO 2
<211> LENGTH: 281
<212> TYPE: PRT
<213> ORGANISM: Macaca mulatta

<400> SEQUENCE: 2

Met Ser Ala Gln Glu Ser Cys Leu Ser Leu Ile Lys Tyr Phe Leu Phe
1               5                   10                  15

Val Phe Asn Leu Phe Phe Phe Val Ile Leu Gly Ser Leu Ile Phe Cys
            20                  25                  30

Phe Gly Ile Trp Ile Leu Ile Asp Lys Thr Ser Phe Val Ser Phe Val
        35                  40                  45

Gly Leu Ala Phe Val Pro Leu Gln Ile Trp Ser Lys Val Leu Ala Ile
    50                  55                  60

Ser Gly Val Phe Thr Met Gly Leu Ala Leu Leu Gly Cys Val Gly Ala
65                  70                  75                  80

Leu Lys Glu Leu Arg Cys Leu Leu Gly Leu Tyr Phe Gly Met Leu Leu
                85                  90                  95

Leu Leu Phe Ala Thr Gln Ile Thr Leu Gly Ile Leu Ile Ser Thr Gln
            100                 105                 110

Arg Ala Gln Leu Glu Arg Ser Leu Gln Asp Ile Val Glu Lys Thr Ile
        115                 120                 125

Gln Arg Tyr His Thr Asn Pro Glu Glu Thr Ala Ala Glu Glu Ser Trp
    130                 135                 140

Asp Tyr Val Gln Phe Gln Leu Arg Cys Cys Gly Trp His Ser Pro Gln
145                 150                 155                 160

Asp Trp Phe Gln Val Leu Thr Leu Arg Gly Asn Gly Ser Glu Ala His
                165                 170                 175

Arg Val Pro Cys Ser Cys Tyr Asn Leu Ser Ala Thr Asn Asp Ser Thr
            180                 185                 190

Ile Leu Asp Lys Val Ile Leu Pro Gln Leu Ser Arg Leu Gly Gln Leu
        195                 200                 205

```
Ala Arg Ser Arg His Ser Thr Asp Ile Cys Ala Val Pro Ala Asn Ser
    210                 215                 220

His Ile Tyr Arg Glu Gly Cys Ala Arg Ser Leu Gln Lys Trp Leu His
225                 230                 235                 240

Asn Asn Leu Ile Ser Ile Val Gly Ile Cys Leu Gly Val Gly Leu Leu
                245                 250                 255

Glu Leu Gly Phe Met Thr Leu Ser Ile Phe Leu Cys Arg Asn Leu Asp
                260                 265                 270

His Val Tyr Asn Arg Leu Arg Tyr Arg
                275                 280

<210> SEQ ID NO 3
<211> LENGTH: 281
<212> TYPE: PRT
<213> ORGANISM: Mus musculus

<400> SEQUENCE: 3

Met Ser Ala Gln Glu Ser Cys Leu Ser Leu Ile Lys Tyr Phe Leu Phe
1               5                   10                  15

Val Phe Asn Leu Phe Phe Phe Val Leu Gly Leu Ile Phe Cys Phe
            20                  25                  30

Gly Thr Trp Ile Leu Ile Asp Lys Thr Ser Phe Val Ser Phe Val Gly
                35                  40                  45

Leu Ser Phe Val Pro Leu Gln Thr Trp Ser Lys Val Leu Ala Val Ser
    50                  55                  60

Gly Val Leu Thr Met Ala Leu Ala Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
                100                 105                 110

Val Arg Leu Glu Arg Arg Val Gln Glu Leu Val Leu Arg Thr Ile Gln
            115                 120                 125

Ser Tyr Arg Thr Asn Pro Asp Glu Thr Ala Ala Glu Glu Ser Trp Asp
    130                 135                 140

Tyr Ala Gln Phe Gln Leu Arg Cys Cys Gly Trp Gln Ser Pro Arg Asp
145                 150                 155                 160

Trp Asn Lys Ala Gln Met Leu Lys Ala Asn Glu Ser Glu Glu Pro Phe
                165                 170                 175

Val Pro Cys Ser Cys Tyr Asn Ser Thr Ala Thr Asn Asp Ser Thr Val
            180                 185                 190

Phe Asp Lys Leu Phe Phe Ser Gln Leu Ser Arg Leu Gly Pro Arg Ala
    195                 200                 205

Lys Leu Arg Gln Thr Ala Asp Ile Cys Ala Leu Pro Ala Lys Ala His
    210                 215                 220

Ile Tyr Arg Glu Gly Cys Ala Gln Ser Leu Gln Lys Trp Leu His Asn
225                 230                 235                 240

Asn Ile Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
                260                 265                 270

Val Tyr Asp Arg Leu Ala Arg Tyr Arg
                275                 280
```

```
<210> SEQ ID NO 4
<211> LENGTH: 5
<212> TYPE: PRT
<213> ORGANISM: artificial sequence
<220> FEATURE:
<223> OTHER INFORMATION: CD37-3 VL-CDR1

<400> SEQUENCE: 4

Thr Ser Gly Val Ser
1               5

<210> SEQ ID NO 5
<211> LENGTH: 9
<212> TYPE: PRT
<213> ORGANISM: artificial sequence
<220> FEATURE:
<223> OTHER INFORMATION: CD37-3 VL-CDR2

<400> SEQUENCE: 5

Val Ile Trp Gly Asp Gly Ser Thr Asn
1               5

<210> SEQ ID NO 6
<211> LENGTH: 7
<212> TYPE: PRT
<213> ORGANISM: artificial sequence
<220> FEATURE:
<223> OTHER INFORMATION: CD37-3 VH-CDR3

<400> SEQUENCE: 6

Gly Gly Tyr Ser Leu Ala His
1               5

<210> SEQ ID NO 7
<211> LENGTH: 11
<212> TYPE: PRT
<213> ORGANISM: artificial sequence
<220> FEATURE:
<223> OTHER INFORMATION: CD37-3 VL-CDR1

<400> SEQUENCE: 7

Arg Ala Ser Glu Asn Ile Arg Ser Asn Leu Ala
1               5                   10

<210> SEQ ID NO 8
<211> LENGTH: 7
<212> TYPE: PRT
<213> ORGANISM: artificial sequence
<220> FEATURE:
<223> OTHER INFORMATION: CD37-3 VL-CDR2

<400> SEQUENCE: 8

Val Ala Thr Asn Leu Ala Asp
1               5

<210> SEQ ID NO 9
<211> LENGTH: 9
<212> TYPE: PRT
<213> ORGANISM: artificial sequence
<220> FEATURE:
<223> OTHER INFORMATION: CD37-3 VL-CDR3

<400> SEQUENCE: 9

Gln His Tyr Trp Gly Thr Thr Trp Thr
1               5

<210> SEQ ID NO 10
```

<211> LENGTH: 115
<212> TYPE: PRT
<213> ORGANISM: artificial sequence
<220> FEATURE:
<223> OTHER INFORMATION: VH muCD37-3

<400> SEQUENCE: 10

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
    115

<210> SEQ ID NO 11
<211> LENGTH: 115
<212> TYPE: PRT
<213> ORGANISM: artificial sequence
<220> FEATURE:
<223> OTHER INFORMATION: VH chCD37-3

<400> SEQUENCE: 11

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
    115

<210> SEQ ID NO 12
<211> LENGTH: 115
<212> TYPE: PRT
<213> ORGANISM: artificial sequence
<220> FEATURE:
<223> OTHER INFORMATION: VH huCD37-3 -version 1.0

<400> SEQUENCE: 12

Gln Val Gln Val Gln Glu Ser Gly Pro Gly Leu Val Ala Pro Ser Gln
1               5                   10                  15

```
Thr Leu Ser Ile Thr Cys Thr Val Ser Gly Phe Ser Leu Thr Thr Ser
            20                  25                  30

Gly Val Ser Trp Val Arg Gln Pro Gly Lys Gly Leu Glu Trp Leu
        35                  40                  45

Gly Val Ile Trp Gly Asp Gly Ser Thr Asn Tyr His Pro Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser
        115

<210> SEQ ID NO 13
<211> LENGTH: 108
<212> TYPE: PRT
<213> ORGANISM: artificial sequence
<220> FEATURE:
<223> OTHER INFORMATION: VL muCD37-3

<400> SEQUENCE: 13

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg
            100                 105

<210> SEQ ID NO 14
<211> LENGTH: 108
<212> TYPE: PRT
<213> ORGANISM: artificial sequence
<220> FEATURE:
<223> OTHER INFORMATION: VL chCD37-3

<400> SEQUENCE: 14

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95
```

Thr Phe Gly Gly Gly Thr Lys Leu Glu Ile Lys Arg
            100                 105

<210> SEQ ID NO 15
<211> LENGTH: 108
<212> TYPE: PRT
<213> ORGANISM: artificial sequence
<220> FEATURE:
<223> OTHER INFORMATION: VL huCD37-3- v1.0 and v1.1

<400> SEQUENCE: 15

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg
            100                 105

<210> SEQ ID NO 16
<211> LENGTH: 445
<212> TYPE: PRT
<213> ORGANISM: artificial sequence
<220> FEATURE:
<223> OTHER INFORMATION: heavy chain muCD37-3

<400> SEQUENCE: 16

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser

```
                    180                 185                 190
Gln Ser Ile Thr Cys Asn Val Ala His Pro Ala Ser Thr Lys Val
            195                 200                 205
Asp Lys Lys Ile Glu Pro Arg Gly Pro Thr Ile Lys Pro Cys Pro
        210                 215                 220
Cys Lys Cys Pro Ala Pro Asn Leu Leu Gly Gly Pro Ser Val Phe Ile
225                 230                 235                 240
Phe Pro Pro Lys Ile Lys Asp Val Leu Met Ile Ser Leu Ser Pro Ile
                245                 250                 255
Val Thr Cys Val Val Val Asp Val Ser Glu Asp Pro Asp Val Gln
        260                 265                 270
Ile Ser Trp Phe Val Asn Asn Val Glu Val His Thr Ala Gln Thr Gln
        275                 280                 285
Thr His Arg Glu Asp Tyr Asn Ser Thr Leu Arg Val Val Ser Ala Leu
        290                 295                 300
Pro Ile Gln His Gln Asp Trp Met Ser Gly Lys Glu Phe Lys Cys Lys
305                 310                 315                 320
Val Asn Asn Lys Asp Leu Pro Ala Pro Ile Glu Arg Thr Ile Ser Lys
                325                 330                 335
Pro Lys Gly Ser Val Arg Ala Pro Gln Val Tyr Val Leu Pro Pro Pro
                340                 345                 350
Glu Glu Glu Met Thr Lys Lys Gln Val Thr Leu Thr Cys Met Val Thr
            355                 360                 365
Asp Phe Met Pro Glu Asp Ile Tyr Val Glu Trp Thr Asn Asn Gly Lys
        370                 375                 380
Thr Glu Leu Asn Tyr Lys Asn Thr Glu Pro Val Leu Asp Ser Asp Gly
385                 390                 395                 400
Ser Tyr Phe Met Tyr Ser Lys Leu Arg Val Glu Lys Lys Asn Trp Val
                405                 410                 415
Glu Arg Asn Ser Tyr Ser Cys Ser Val Val His Glu Gly Leu His Asn
            420                 425                 430
His His Thr Thr Lys Ser Phe Ser Arg Thr Pro Gly Lys
            435                 440                 445

<210> SEQ ID NO 17
<211> LENGTH: 445
<212> TYPE: PRT
<213> ORGANISM: artificial sequence
<220> FEATURE:
<223> OTHER INFORMATION: heavy chain chCD37-3

<400> SEQUENCE: 17

Gln Val Gln Val Lys Glu Ser Gly Pro Gly Leu Val Ala Pro Ser Gln
1               5                   10                  15
Ser Leu Ser Ile Thr Cys Thr Val Ser Gly Phe Ser Leu Thr Thr Ser
            20                  25                  30
Gly Val Ser Trp Val Arg Gln Pro Pro Gly Lys Gly Leu Glu Trp Leu
        35                  40                  45
Gly Val Ile Trp Gly Asp Gly Ser Thr Asn Tyr His Ser Ala Leu Lys
    50                  55                  60
Ser Arg Leu Ser Ile Lys Lys Asp His Ser Lys Ser Gln Val Phe Leu
65                  70                  75                  80
Lys Leu Asn Ser Leu Gln Thr Asp Asp Thr Ala Thr Tyr Tyr Cys Ala
                85                  90                  95
Lys Gly Gly Tyr Ser Leu Ala His Trp Gly Gln Gly Thr Leu Val Thr
```

```
                100             105             110
Val Ser Ala Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 18
<211> LENGTH: 444
<212> TYPE: PRT
<213> ORGANISM: artificial sequence
<220> FEATURE:
<223> OTHER INFORMATION: heavy chain huCD37-3 v1.0

<400> SEQUENCE: 18

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
```

-continued

```
             20                  25                  30
Gly Val Ser Trp Val Arg Gln Pro Gly Lys Gly Leu Glu Trp Leu
             35                  40                  45
Gly Val Ile Trp Gly Asp Gly Ser Thr Asn Tyr His Pro Ser Leu Lys
 50                  55                  60
Ser Arg Leu Ser Ile Lys Lys Asp His Ser Lys Ser Gln Val Phe Leu
 65                  70                  75                  80
Lys Leu Asn Ser Leu Thr Ala Ala Asp Thr Ala Thr Tyr Tyr Cys Ala
                 85                  90                  95
Lys Gly Gly Tyr Ser Leu Ala His Trp Gly Gln Gly Thr Leu Val Thr
                100                 105                 110
Val Ser Ser Ala Ser Thr Lys Gly Pro Ser Val Phe Pro Leu Ala Pro
                115                 120                 125
Ser Ser Lys Ser Thr Ser Gly Gly Thr Ala Ala Leu Gly Cys Leu Val
                130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
                195                 200                 205
Val Asp Lys Lys Val Glu Pro Lys Ser Cys Asp Lys Thr His Thr Cys
                210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
                260                 265                 270
Phe Asn Trp Tyr Val Asp Gly Val Glu Val His Asn Ala Lys Thr Lys
                275                 280                 285
Pro Arg Glu Glu Gln Tyr Asn Ser Thr Tyr Arg Val Val Ser Val Leu
                290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Arg Asp Glu Leu Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
                370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
His Tyr Thr Gln Lys Ser Leu Ser Leu Ser Pro Gly
                435                 440
```

<210> SEQ ID NO 19
<211> LENGTH: 214
<212> TYPE: PRT
<213> ORGANISM: artificial sequence
<220> FEATURE:
<223> OTHER INFORMATION: light chain muCD37-3

<400> SEQUENCE: 19

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 20
<211> LENGTH: 214
<212> TYPE: PRT
<213> ORGANISM: artificial sequence
<220> FEATURE:
<223> OTHER INFORMATION: light chain chCD37-3

<400> SEQUENCE: 20

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp

```
                85                  90                  95
Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 21
<211> LENGTH: 214
<212> TYPE: PRT
<213> ORGANISM: artificial sequence
<220> FEATURE:
<223> OTHER INFORMATION: light chain huCD37-3- v1.0 and v1.1

<400> SEQUENCE: 21

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
                20                  25                  30

Leu Ala Trp Tyr Gln Gln Lys Pro Gly Lys Ser Pro Lys Leu Leu Val
            35                  40                  45

Asn Val Ala Thr Asn Leu Ala Asp Gly Val Pro Ser Arg Phe Ser Gly
        50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210
```

```
<210> SEQ ID NO 22
<211> LENGTH: 115
<212> TYPE: PRT
<213> ORGANISM: artificial sequence
<220> FEATURE:
<223> OTHER INFORMATION: VH huCD37-3- version 1.1

<400> SEQUENCE: 22

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser
        115

<210> SEQ ID NO 23
<211> LENGTH: 122
<212> TYPE: PRT
<213> ORGANISM: artificial sequence
<220> FEATURE:
<223> OTHER INFORMATION: VH Veltuzumab

<400> SEQUENCE: 23

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Lys Gln Ala Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95

Ala Arg Ser Thr Tyr Tyr Gly Gly Asp Trp Tyr Phe Asp Val Trp Gly
            100                 105                 110

Gln Gly Thr Thr Val Thr Val Ser Ser Ala
        115                 120

<210> SEQ ID NO 24
<211> LENGTH: 121
<212> TYPE: PRT
<213> ORGANISM: artificial sequence
<220> FEATURE:
<223> OTHER INFORMATION: VH Rituximab

<400> SEQUENCE: 24

Gln Val Gln Leu Gln Gln Pro Gly Ala Glu Leu Val Lys Pro Gly Ala
1               5                   10                  15
```

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
            115                 120

<210> SEQ ID NO 25
<211> LENGTH: 122
<212> TYPE: PRT
<213> ORGANISM: artificial sequence
<220> FEATURE:
<223> OTHER INFORMATION: VH Ofatumumab

<400> SEQUENCE: 25

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
            35                  40                  45

Ser Thr Ile Ser Trp Asn Ser Gly Ser Ile Gly Tyr Ala Asp Ser Val
50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
            115                 120

<210> SEQ ID NO 26
<211> LENGTH: 119
<212> TYPE: PRT
<213> ORGANISM: artificial sequence
<220> FEATURE:
<223> OTHER INFORMATION: VH Obinutuzumab

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
50                  55                  60

Lys Gly Arg Val Thr Ile Thr Ala Asp Lys Ser Thr Ser Thr Ala Tyr

```
                 65                  70                  75                  80
Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
               100                 105                 110

Thr Leu Val Thr Val Ser Ser
        115

<210> SEQ ID NO 27
<211> LENGTH: 119
<212> TYPE: PRT
<213> ORGANISM: artificial sequence
<220> FEATURE:
<223> OTHER INFORMATION: VH huCD20-4

<400> SEQUENCE: 27

Glu Val Gln Val Glu Glu Ser Gly Gly Gly Leu Val Gln Pro Gly Gly
1               5                  10                  15

Ser Met Arg Leu Ser Cys Val Ala Ser Gly Phe Ser Phe Asn Asn Tyr
                20                  25                  30

Trp Met Asn Trp Val Arg Gln Ser Pro Gly Lys Gly Leu Glu Trp Val
            35                  40                  45

Ala Glu Ile Arg Leu Lys Ser Asn Asn Tyr Ala Thr His Tyr Val Asp
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Trp Asp Asp Tyr Ala Met Asp His Trp Gly Gln Gly
               100                 105                 110

Ile Ser Val Thr Val Ser Ser
        115

<210> SEQ ID NO 28
<211> LENGTH: 121
<212> TYPE: PRT
<213> ORGANISM: artificial sequence
<220> FEATURE:
<223> OTHER INFORMATION: VH huCD20-7 v1.0

<400> SEQUENCE: 28

Glu Leu Gln Leu Val Gln Ser Gly Gly Glu Leu Lys Lys Pro Gly Glu
1               5                  10                  15

Thr Val Arg Ile Ser Cys Ala Ala Ser Gly Tyr Ser Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Ser Tyr Ala Ala Pro Phe
        50                  55                  60

Lys Gly Arg Phe Ala Phe Ser Leu Glu Thr Ser Ala Ser Thr Ala Tyr
65                  70                  75                  80

Leu Gln Ile Ser Ser Leu Lys Thr Glu Asp Thr Ala Thr Tyr Phe Cys
                85                  90                  95

Ala Arg Gly Ala Tyr Tyr Arg Tyr Asp Leu Gly Met Asp Tyr Trp Gly
               100                 105                 110

Gln Gly Thr Ser Val Thr Val Ser Ser
        115                 120
```

```
<210> SEQ ID NO 29
<211> LENGTH: 121
<212> TYPE: PRT
<213> ORGANISM: artificial sequence
<220> FEATURE:
<223> OTHER INFORMATION: VH huCD20-7 v. 1.1

<400> SEQUENCE: 29

Glu Leu Gln Leu Val Gln Ser Gly Gly Glu Leu Lys Lys Pro Gly Glu
1               5                   10                  15

Thr Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Ser Tyr Ala Ala Pro Phe
    50                  55                  60

Lys Gly Arg Phe Ala Phe Ser Leu Glu Thr Ser Ala Ser Thr Ala Tyr
65                  70                  75                  80

Leu Gln Ile Ser Ser Leu Lys Thr Glu Asp Thr Ala Thr Tyr Phe Cys
                85                  90                  95

Ala Arg Gly Ala Tyr Tyr Arg Tyr Asp Leu Gly Met Asp Tyr Trp Gly
            100                 105                 110

Gln Gly Thr Ser Val Thr Val Ser Ser
        115                 120

<210> SEQ ID NO 30
<211> LENGTH: 106
<212> TYPE: PRT
<213> ORGANISM: artificial sequence
<220> FEATURE:
<223> OTHER INFORMATION: VL Veltuzumab

<400> SEQUENCE: 30

Asp Ile Gln Leu Thr Gln Ser Pro Ser Ser Leu Ser Ala Ser Val Gly
1               5                   10                  15

Asp Arg Val Thr Met Thr Cys Arg Ala Ser Ser Ser Val Ser Tyr Ile
            20                  25                  30

His Trp Phe Gln Gln Lys Pro Gly Lys Ala Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 31
<211> LENGTH: 106
<212> TYPE: PRT
<213> ORGANISM: artificial sequence
<220> FEATURE:
<223> OTHER INFORMATION: VL Rituximab

<400> SEQUENCE: 31

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
```

```
                    20                  25                  30
His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 32
<211> LENGTH: 107
<212> TYPE: PRT
<213> ORGANISM: artificial sequence
<220> FEATURE:
<223> OTHER INFORMATION: VL Ofatumumab

<400> SEQUENCE: 32

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 33
<211> LENGTH: 112
<212> TYPE: PRT
<213> ORGANISM: artificial sequence
<220> FEATURE:
<223> OTHER INFORMATION: VL Obinutuzumab

<400> SEQUENCE: 33

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110
```

<210> SEQ ID NO 34
<211> LENGTH: 108
<212> TYPE: PRT
<213> ORGANISM: artificial sequence
<220> FEATURE:
<223> OTHER INFORMATION: VL huCD20-4

<400> SEQUENCE: 34

```
Asp Ile Gln Met Thr Gln Ser Pro Ser Thr Met Ser Thr Ser Val Gly
1               5                   10                  15

Asp Arg Val Ser Val Asn Cys Lys Ala Ser Gln Asn Val Gly Thr Asn
            20                  25                  30

Val Ala Trp Tyr Gln Gln Lys Pro Gly Lys Ser Pro Lys Gly Leu Ile
        35                  40                  45

Tyr Ser Ala Ser Phe Arg Tyr Ser Gly Val Pro Ser Arg Phe Thr Gly
    50                  55                  60

Ser Gly Ser Gly Thr Asp Phe Thr Leu Thr Ile Phe Asn Val Gln Pro
65                  70                  75                  80

Asp Asp Leu Ala Glu Tyr Phe Cys Gln Gln Tyr Asn Asn Tyr Pro Leu
                85                  90                  95

Thr Phe Gly Gly Gly Thr Lys Leu Glu Ile Lys Arg
            100                 105
```

<210> SEQ ID NO 35
<211> LENGTH: 112
<212> TYPE: PRT
<213> ORGANISM: artificial sequence
<220> FEATURE:
<223> OTHER INFORMATION: VL huCD20-7

<400> SEQUENCE: 35

```
Asp Ile Val Leu Thr Gln Ser Pro Ala Ser Leu Ala Val Ser Pro Gly
1               5                   10                  15

Gln Arg Ala Thr Ile Ser Cys Arg Ala Ser Gly Ser Val Asp Ser Phe
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Gly Ser Arg Thr Asp Phe Thr Leu Thr Ile Asn
65                  70                  75                  80

Pro Val Glu Ala Asn Asp Ile Ala Thr Tyr Phe Cys Gln Gln Ser Tyr
                85                  90                  95

Glu Asp Pro Phe Thr Phe Gly Gln Gly Thr Lys Leu Glu Leu Lys Arg
            100                 105                 110
```

<210> SEQ ID NO 36
<211> LENGTH: 297
<212> TYPE: PRT
<213> ORGANISM: Homo sapiens

<400> SEQUENCE: 36

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45
```

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 37
<211> LENGTH: 444
<212> TYPE: PRT
<213> ORGANISM: artificial sequence
<220> FEATURE:
<223> OTHER INFORMATION: heavy chain huCD37-3 v1.1

<400> SEQUENCE: 37

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

-continued

| | | | | | | | | | | | |
|---|---|---|---|---|---|---|---|---|---|---|---|
|Val|Ser|Ser|Ala|Ser|Thr|Lys|Gly|Pro|Ser|Val|Phe|Pro|Leu|Ala|Pro
| | |115| | | |120| | | |125| |

Ser Ser Lys Ser Thr Ser Gly Gly Thr Ala Ala Leu Gly Cys Leu Val
        130              135              140

Lys Asp Tyr Phe Pro Glu Pro Val Thr Val Ser Trp Asn Ser Gly Ala
145              150              155              160

Leu Thr Ser Gly Val His Thr Phe Pro Ala Val Leu Gln Ser Ser Gly
                165              170              175

Leu Tyr Ser Leu Ser Ser Val Val Thr Val Pro Ser Ser Ser Leu Gly
                180              185              190

Thr Gln Thr Tyr Ile Cys Asn Val Asn His Lys Pro Ser Asn Thr Lys
            195              200              205

Val Asp Lys Lys Val Glu Pro Lys Ser Cys Asp Lys Thr His Thr Cys
    210              215              220

Pro Pro Cys Pro Ala Pro Glu Leu Leu Gly Gly Pro Ser Val Phe Leu
225              230              235              240

Phe Pro Pro Lys Pro Lys Asp Thr Leu Met Ile Ser Arg Thr Pro Glu
                245              250              255

Val Thr Cys Val Val Val Asp Val Ser His Glu Asp Pro Glu Val Lys
                260              265              270

Phe Asn Trp Tyr Val Asp Gly Val Glu Val His Asn Ala Lys Thr Lys
            275              280              285

Pro Arg Glu Glu Gln Tyr Asn Ser Thr Tyr Arg Val Val Ser Val Leu
        290              295              300

Thr Val Leu His Gln Asp Trp Leu Asn Gly Lys Glu Tyr Lys Cys Lys
305              310              315              320

Val Ser Asn Lys Ala Leu Pro Ala Pro Ile Glu Lys Thr Ile Ser Lys
                325              330              335

Ala Lys Gly Gln Pro Arg Glu Pro Gln Val Tyr Thr Leu Pro Pro Ser
            340              345              350

Arg Asp Glu Leu Thr Lys Asn Gln Val Ser Leu Thr Cys Leu Val Lys
        355              360              365

Gly Phe Tyr Pro Ser Asp Ile Ala Val Glu Trp Glu Ser Asn Gly Gln
370              375              380

Pro Glu Asn Asn Tyr Lys Thr Thr Pro Pro Val Leu Asp Ser Asp Gly
385              390              395              400

Ser Phe Phe Leu Tyr Ser Lys Leu Thr Val Asp Lys Ser Arg Trp Gln
                405              410              415

Gln Gly Asn Val Phe Ser Cys Ser Val Met His Glu Ala Leu His Asn
            420              425              430

His Tyr Thr Gln Lys Ser Leu Ser Leu Ser Pro Gly
        435              440

ANTI-CD37 IMMUNOCONJUGATE AND ANTI-CD20 ANTIBODY COMBINATIONS

REFERENCE TO EARLIER FILED APPLICATIONS

This application is a continuation of U.S. application Ser. No. 15/171,732, filed Jun. 2, 2016, which claims the benefit of U.S. Provisional Application No. 62/263,449, filed Dec. 4, 2015, and U.S. Provisional Application No. 62/172,672, filed Jun. 8, 2015, all of which are incorporated herein by reference in their entireties.

REFERENCE TO SEQUENCE LISTING SUBMITTED ELECTRONICALLY VIA EFS-WEB

The content of the electronically submitted sequence listing (Name: 4018_0040003_SL_ST25.txt, Size: 54,498 bytes; and Date of Creation: Oct. 22, 2018) is incorporated herein by reference in its entirety.

FIELD OF THE INVENTION

The field of the invention generally relates to synergistic combinations of an anti-CD37 immunoconjugate (e.g., IMGN529) and an anti-CD20 antibody and their use in the treatment of cancer.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime.

Leukocyte antigen CD37 ("CD37"), also known as GP52-40, tetraspanin-26, or TSPAN26, is expressed on B cells during the pre-B to peripheral mature B-cell stages, but is absent on terminal differentiation to plasma cells. (Link et al., 1987, J Pathol. 152:12-21). The CD37 antigen is only weakly expressed on T-cells, myeloid cells and granulocytes (Schwartz-Albiez et al. 1988, J. Immunol., 140(3)905-914). However, CD37 is also expressed on malignant B-cells such as those found in non-Hodgkin's lymphoma (NHL) and chronic lymphoid leukemia (CLL) (Moore et al. 1986, J Immunol. 137(9):3013-8). This expression profile suggests that CD37 represents a promising therapeutic target for B-cell malignancies.

CD20, also known as membrane-spanning 4-domains, subfamily A, member 1 (MS4A1), B-lymphocyte surface antigen B1, and Leukocyte surface antigen Leu-16, is also expressed on B cells. Several anti-CD20 antibodies, including rituximab, obinutuzumab, and ofatumumab, are indicated for the treatment of certain B-cell cancers. However, many B-cell cancers in many patients do not respond to these treatments, and even cancers that initially respond frequently relapse or do not respond to subsequent therapy. For example, cancers that overexpress the transcription factor MYC and the anti-apoptotic protein BCL2 are associated with a poor prognosis.

Given that the prognosis for many patients with B cell cancers remains poor, there is a clear unmet medical need for more effective therapeutics for B-cell malignancies.

BRIEF SUMMARY OF THE INVENTION

Combinations of an anti-CD37 immunoconjugate (e.g. IMGN529) and an anti-CD20 antibody or antigen-binding fragment thereof are provided herein. Also provided herein are methods of treating a patient with cancer using such a combination. As described in more detail below, use of an anti-CD37 immunoconjugate (e.g. IMGN529) in combination with an anti-CD20 antibody or antigen-binding fragment thereof can result in synergistic efficacy against tumors. The anti-CD20 antibody or antigen-binding fragment thereof can potentiate the efficacy of the anti-CD37 immunoconjugate (e.g. IMGN529) and/or the anti-CD37 immunoconjugate (e.g. IMGN529) can potentiate the efficacy of the anti-CD20 antibody. By using the combination of an anti-CD37 immunoconjugate (e.g. IMGN529) and an anti-CD20 antibody or antigen-binding fragment thereof, the sum of their efficacy can be achieved even while using smaller and/or less frequent doses of the an anti-CD37 immunoconjugate (e.g. IMGN529) and/or anti-CD20 antibody or antigen-binding fragment thereof. Moreover, the combination can produce no more toxicity than the anti-CD20 antibody or antigen-binding fragment thereof alone, the anti-CD37 immunoconjugate (e.g. IMGN529) alone, and/or either the anti-CD20 antibody or antigen-binding fragment thereof or the anti-CD37 immunoconjugate (e.g. IMGN529).

In one instance, a method for treating a patient having a B-cell cancer comprises administering to said patient in need thereof an immunoconjugate that binds to CD37 comprising an antibody comprising VH CDR1, VH CDR2, VH CDR3, VL CDR1, VL CDR2, and VL CDR3 sequences as set forth in SEQ ID NOs: 4-9, respectively; and an anti-CD20 antibody.

In one instance, the immunoconjugate that binds to CD37 comprises an antibody that competitively inhibits the binding of an antibody with the sequences of SEQ ID NOs:12 and 15 to CD37. In one instance, the immunoconjugate that binds to CD37 comprises the variable heavy chain sequence set forth in SEQ ID NO:12 and the variable light chain sequence set forth in SEQ ID NO:15. In one instance, the immunoconjugate that binds to CD37 comprises the variable heavy chain sequence set forth in SEQ ID NO:22 and the variable light chain sequence set forth in SEQ ID NO:15. In one instance, the antibody is huCD37-3.

In one instance, the immunoconjugate comprises a maytansinoid. In one instance, the maytansinoid is DM1.

In one instance, the immunoconjugate comprises a non-cleavable linker. In one instance, the linker is SMCC.

In one instance, the immunoconjugate is IMGN529.

In one instance, the antibody or antigen-binding fragment thereof that binds to CD20 is selected from the group consisting of rituximab, ofatumumab, obinutuzumab, and vetuzuamb.

In one instance, the antibody or antigen-binding fragment thereof that binds to CD20 is vetuzuamb.

In one instance, the antibody or antigen-binding fragment thereof that binds to CD20 is selected from the group consisting of rituximab, ofatumumab, and obinutuzumab.

In one instance, the antibody or antigen-binding fragment thereof that binds to CD20 is obinutuzumab.

In one instance, the antibody or antigen-binding fragment thereof that binds to CD20 is selected from the group consisting of rituximab and ofatumumab. In one instance, the antibody or antigen-binding fragment thereof that binds to CD20 is rituximab. In one instance, the antibody or antigen-binding fragment thereof that binds to CD20 is ofatumumab.

In one instance, the antibody or antigen-binding fragment thereof that binds to CD20 is a type I antibody or antigen-binding fragment thereof.

In one instance, the antibody or antigen-binding fragment thereof that binds to CD20 is not rituximab. In some embodiments, the anti-CD20 antibody does not bind to the same epitope as rituximab. In one instance, the antibody or antigen-binding fragment thereof that binds to CD20 is not ofatumumab. In one instance, the antibody or antigen-binding fragment thereof that binds to CD20 is a type II antibody or antigen binding fragment thereof.

In one instance, the immunoconjugate that binds to CD37 (e.g., IMGN529) and the antibody or antigen-binding fragment thereof that binds to CD20 produce a synergistic effect. In one instance, the immunoconjugate that binds to CD37 (e.g., IMGN529) and the antibody or antigen-binding fragment thereof that binds to CD20 produce a Synergy Score of at least 4 in vitro. In one instance, the Synergy Score is at least 10. In one instance, the Synergy Score is at least 20. In one instance, the Synergy Score is at least 30. In one instance, the Synergy Score is at least 40.

In one instance, the immunoconjugate that binds to CD37 (e.g., IMGN529) and the antibody or antigen-binding fragment thereof that binds to CD20 have a combination index value of less than 0.5.

In one instance, administration of the immunoconjugate that binds CD37 (e.g., IMGN529) and the antibody or antigen-binding fragment thereof that binds to CD20 does not produce more toxicity than administration of the immunoconjugate that binds CD37 (e.g., IMGN529) alone. In one instance, administration of the immunoconjugate that binds CD37 (e.g., IMGN529) and the antibody or antigen-binding fragment thereof that binds to CD20 does not produce more toxicity than administration of the antibody that binds to CD20 alone. In one instance, administration of the immunoconjugate that binds CD37 (e.g., IMGN529) and the antibody or antigen-binding fragment thereof that binds to CD20 does not produce more toxicity than administration of R-CHOP. In one instance, administration of the immunoconjugate that binds CD37 (e.g., IMGN529) and the antibody or antigen-binding fragment thereof that binds to CD20 produces less toxicity than administration of R-CHOP.

In one instance, the cancer is a B cell malignancy. In one instance, the cancer is leukemia or lymphoma. In one instance, the cancer is selected from the group consisting of B-cell lymphomas including NHL, precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma, plasmacytoma, plasma cell myeloma, post-transplant lymphoproliferative disorder, Waldenstrom's macroglobulinemia, acute lymphoblastic leukemia (ALL), and anaplastic large-cell lymphoma (ALCL). In one instance, the cancer is NHL. In one instance, the NHL is relapsed or refractory NHL. In one instance, the NHL is diffuse large B-cell lymphoma (DLBCL). In one instance, the DLBCL is GCB DLBCL. In one instance, the DLBCL is ABC DLBCL. In one instance, the NHL is mantle cell lymphoma (MCL). In one instance, the NHL is chronic lymphocytic leukemia (CLL). In one instance, the NHL is follicular lymphoma.

In one instance, the cancer overexpresses MYC. In one instance, the cancer overexpresses BCL2. In one instance, the cancer overexpresses MYC and BCL2.

In one instance, the immunoconjugate that binds to CD37 (e.g., IMGN529) and the antibody or antigen-binding fragment thereof that binds to CD20 are administered simultaneously. In one instance, the immunoconjugate that binds to CD37 (e.g., IMGN529) and the antibody or antigen-binding fragment thereof that binds to CD20 are administered in separate pharmaceutical compositions. In one instance, the immunoconjugate that binds to CD37 (e.g., IMGN529) and the antibody or antigen-binding fragment thereof that binds to CD20 are administered in the same pharmaceutical composition. In one instance, the immunoconjugate that binds to CD37 (e.g., IMGN529) and the antibody or antigen-binding fragment thereof that binds to CD20 are administered sequentially.

In one instance, the immunoconjugate (e.g., IMGN529) is administered at a dose of from about 0.1 mg/kg to about 2.8 mg/kg. In one instance, the immunoconjugate (e.g., IMGN529) is administered at a dose of from about 0.4 mg/kg to about 2.8 mg/kg. In one instance, the immunoconjugate (e.g., IMGN529) is administered at a dose of from about 0.4 mg/kg to about 2.0 mg/kg. In one instance, the immunoconjugate (e.g., IMGN529) is administered at a dose of from about 0.4 mg/kg to about 1.4 mg/kg. In one instance, the immunoconjugate (e.g., IMGN529) is administered at a dose of from about 0.7 mg/kg to about 1.8 mg/kg. In one instance, the immunoconjugate (e.g., IMGN529) is administered at a dose of from about 1.4 mg/kg to about 2.8 mg/kg. In one instance, the immunoconjugate (e.g., IMGN529) is administered at a dose of from about 1.4 mg/kg to about 2.0 mg/kg. In one instance, the immunoconjugate (e.g., IMGN529) is administered at a dose of from about 2.0 mg/kg to about 2.8 mg/kg. In one instance, the immunoconjugate (e.g., IMGN529) is administered at a dose of about 0.7 mg/kg. In one instance, the immunoconjugate (e.g., IMGN529) is administered at a dose of about 1.0 mg/kg. In one instance, the immunoconjugate (e.g., IMGN529) is administered at a dose of about 1.4 mg/kg. In one instance, the immunoconjugate (e.g., IMGN529) is administered at a dose of about 1.6 mg/kg. In one instance, the immunoconjugate (e.g., IMGN529) is administered at a dose of about 1.8 mg/kg. In one instance, the immunoconjugate (e.g., IMGN529) is administered at a dose of about 2.0 mg/kg. In one instance, the immunoconjugate (e.g., IMGN529) is administered at a dose of about 2.2 mg/kg. In one instance, the immunoconjugate (e.g., IMGN529) is administered at a dose of about 2.4 mg/kg. In one instance, the immunoconjugate (e.g., IMGN529) is administered at a dose of about 2.8 mg/kg. In one instance, the immunoconjugate (e.g., IMGN529) is administered at a dose of about 3.0 mg/kg.

In one instance, the immunoconjugate (e.g., IMGN529) is administered once every three weeks. In one instance, the immunoconjugate (e.g., IMGN529) is administered on day 1 of a 21-day cycle.

In one instance, the antibody or antigen-binding fragment thereof that binds to CD20 is administered at a dose of about 375 mg/m$^2$. In one instance, the antibody or antigen-binding fragment thereof that binds to CD20 is administered once every week. In one instance, the antibody or antigen-binding fragment thereof that binds to CD20 is administered on week 1, day 1 of a 3 week schedule. In one instance, the antibody or antigen-binding fragment thereof that binds to CD20 is administered at a dose of about 500 mg/m$^2$. In one instance, the antibody or antigen-binding fragment thereof that binds to CD20 is administered once every 28 days.

In one instance, the immunoconjugate that binds to CD37 (e.g., IMGN529) and the antibody or antigen-binding fragment thereof that binds to CD20 are administered intravenously.

In one instance, the method further comprising administering a corticosteroid to the patient. In one instance, the corticosteroid is administered prior to the administration of the immunoconjugate (e.g., IMGN529). In one instance, the corticosteroid is administered from about 30 to about 60 minutes prior to administration of the immunoconjugate (e.g., IMGN529). In one instance, the corticosteroid is administered peri-infusionally. In one instance, the corticosteroid is administered during the administration of the immunoconjugate (e.g., IMGN529). In one instance, the corticosteroid is administered at least one additional time from about one day to about four days after administration of the immunoconjugate (e.g., IMGN529). In one instance, the corticosteroid is administered at least one additional time from about one day to about three days after administration of the immunoconjugate (e.g., IMGN529). In one instance, the corticosteroid is administered at least two additional times. In one instance, the corticosteroid is further administered on day two and day three after administration of the immunoconjugate (e.g., IMGN529). In one instance, the corticosteroid is administered after the administration of the immunoconjugate (e.g., IMGN529). In one instance, the corticosteroid is selected from the group consisting of prednisone, prednisolone, methylprednisolone, beclamethasone, betamethasone, dexamethasone, fludrocortisone, hydrocortisone, and triamcinolone. In one instance, the corticosteroid is dexamethasone.

In one instance, the further comprises administering a growth factor to the patient. In one instance, the growth factor is selected from the group consisting of granulocyte colony-stimulating factor (G-CSF), granulocyte-macrophage colony-stimulating factor (GM-CSF), macrophage colony-stimulating factor (M-CSF), filgrastim, and pegfilgrastim. In one instance, the growth factor is G-CSF. In one instance, the growth factor is administered early to mid-cycle. In one instance, the growth factor is administered at least once from day one to day twelve after administration of the immunoconjugate (e.g., IMGN529).

In one instance, the cancer expresses CD37. In one instance, the cancer expresses CD20. In one instance, the cancer expresses CD37 and CD20.

In one instance, the immunoconjugate is IMGN529, the immunoconjugate is administered at a dose of about 0.7 mg/kg once every three weeks, the antibody or antigen-binding fragment thereof that binds to CD20 is rituximab, and the antibody or antigen-binding fragment thereof that binds to CD20 is administered at a dose of about 375 mg/m$^2$ on week 1, day 1 of a three week schedule.

In one instance, a kit comprises a pharmaceutical composition comprising an immunoconjugate that binds to CD37 comprising an antibody comprising VH CDR1, VH CDR2, VH CDR3, VL CDR1, VL CDR2, and VL CDR3 sequences as set forth in SEQ ID NOs: 4-9, respectively; and instructions to administer the immunoconjugate and an anti-CD20 antibody or antigen-binding fragment thereof. In one instance, a kit comprises a pharmaceutical composition comprising an anti-CD20 antibody or an antigen-binding fragment thereof; and instructions to administer the anti-CD20 antibody or antigen-binding fragment thereof and an immunoconjugate that binds to CD37 comprising an antibody comprising VH CDR1, VH CDR2, VH CDR3, VL CDR1, VL CDR2, and VL CDR3 sequences as set forth in SEQ ID NOs: 4-9, respectively. In one instance, the immunoconjugate is IMGN529. In one instance, the antibody or antigen-binding fragment thereof that binds to CD20 is selected from the group consisting of rituximab, ofatumumab, obinutuzumab, and vetuzuamb. In one instance, the antibody or antigen-binding fragment thereof that binds to CD20 is selected from the group consisting of rituximab, ofatumumab, and obinutuzumab. In one instance, the antibody or antigen-binding fragment thereof that binds to CD20 is selected from the group consisting of rituximab and ofatumumab. In one instance, the antibody or antigen-binding fragment thereof that binds to CD20 is rituximab. In one instance, the antibody or antigen-binding fragment thereof that binds to CD20 is a type I antibody or antigen-binding fragment thereof. In one instance, the antibody or antigen-binding fragment thereof that binds to CD20 is a type II antibody or antigen-binding fragment thereof.

In one instance, a method of instructing a human subject with cancer comprises providing instructions to receive cancer treatment with an immunoconjugate that binds to CD37 (e.g., IMGN529) and an antibody or antigen-binding fragment thereof that binds to CD20. In one instance, the immunoconjugate is IMGN529. In one instance, the antibody or antigen-binding fragment thereof that binds to CD20 is selected from the group consisting of rituximab, ofatumumab, obinutuzumab, and vetuzuamb. In one instance, the antibody or antigen-binding fragment thereof that binds to CD20 is selected from the group consisting of rituximab, ofatumumab, and obinutuzumab. In one instance, the antibody or antigen-binding fragment thereof that binds to CD20 is selected from the group consisting of rituximab and ofatumumab. In one instance, the antibody or antigen-binding fragment thereof that binds to CD20 is rituximab. In one instance, the antibody or antigen-binding fragment thereof that binds to CD20 is a type I antibody or antigen-binding fragment thereof. In one instance, the antibody or antigen-binding fragment thereof that binds to CD20 is a type II antibody or antigen-binding fragment thereof.

In one instance, use of the combination of an immunoconjugate that binds to CD37 (e.g., IMGN529) and an antibody or antigen-binding fragment thereof that binds to CD20 achieves the efficacy, synergy, and/or reduction in toxicity as demonstrated in Examples 1-11 and FIGS. 1-17.

BRIEF DESCRIPTION OF THE DRAWINGS/FIGURES

FIG. 1, panels A-F, provide the percent growth inhibition that results from IMGN529 and rituximab in DOHH2 (panel A), SUDHL4 (panel B), U2932 (panel C), GRANTA-519 (panel D), JVM2 (panel E), and Ramos (panel F) cells.

FIG. 2, panels A-F, provide isobolograms obtained using IMGN529 and rituximab in DOHH2 (panel A), SUDHL4 (panel B), U2932 (panel C), GRANTA-519 (panel D), JVM2 (panel E), and Ramos (panel F) cells. The dashed line indicates additivity, and the solid line indicates growth inhibition (%).

FIG. 3, panels A and B, provide percent growth inhibition and an isobologram, respectively, obtained using IMGN529 and rituximab in OCI-Ly18 cells. In FIG. 3, panel B, the dashed line indicates additivity, and the solid line indicates growth inhibition (%).

FIG. 4 shows the synergy scores obtained using rituximab in combination with IMGN529 (black bars), huCD37-3 (gray bars), or DM1-Me (white bars) on various cell lines.

FIG. 5 shows the efficacy of the combination of IMGN529 and rituximab in the Farage survival model. Mice were treated with (i) 5 mg/kg IMGN529 on day 7 (ii) 2.5 mg/kg dose IMGN529 on day 7 (iii) 10 mg/kg rituximab on days 7 and 21 (iv) 5 mg/kg IMGN529 on day 7 and 10 mg/kg rituximab on days 7, 14, and 21, (v) 2.5 mg/kg IMGN529 on day 7 and 10 mg/kg rituximab on days 7, 14, and 21 or (vi) vehicle (negative control).

FIG. 6 shows the results of treating mice bearing SU-DHL-4 DLBCL lymphoma xenografts with vehicle (PBS), IMGN529, rituximab, a combination of IMGN529 and rituximab (R+IMGN529), or R-CHOP. T/C % represents tumor growth inhibition. CR indicates complete response. TFS indicates tumor free survival, and BWL indicates body weight loss.

FIG. 7 shows the results of treating mice bearing DoHH2 FL xenografts with vehicle (PBS), IMGN529, rituximab, a combination of IMGN529 and rituximab (R-IMGN529), or R-CHOP. T/C % represents tumor growth inhibition. PR indicates partial response. CR indicates complete response. TFS indicates tumor free survival. LCK indicates log cell killing, and BWL indicates body weight loss.

FIG. 8, panels A-E, show the Caspase 3/7 activity in cells treated with rituximab, the huCD37-3 antibody, IMGN529, a combination of the huCD37-3 antibody and rituximab, a combination of IMGN529 and rituximab, or staurosporine (positive control) as compared to the activity in cells treated with an huIgG1 isotype control antibody (negative control). The cells tested were DOHH2 (panel A), SU-DHL-4 (panel B), U2932 (panel C), OCI-Ly7 (panel D), and Farage (panel E) cells.

FIG. 9 shows a graph of cell growth inhibition and synergy score for the combination of IMGN529 plus rituximab (black bar) in a panel of NHL cell lines compared to activity of the single agents (IMGN529 alone in white bar and rituximab alone in gray bar).

FIG. 10, panels A-E, show percent growth inhibition in cell lines treated with the combination of IMGN529 plus rituximab at various concentrations of rituximab and IMGN529. The cells tested were U2932 (panel A), OCI-Ly-7 (panel B), Farage (panel C), DOHH2 (panel D), OCI-Ly-10 (panel E).

FIG. 11, panels A-H, show Caspase 3/7 activation (panels A-D) and PARP activation (panels E-H) in cells treated with IMGN529 alone, rituximab alone, or combinations of IMGN529 and rituximab at varying concentrations. The cells tested were U2932 (panels A and E), OCI-Ly7 (panels B and F), SU-DHL-4 (panels C and G), DOHH-2 (panels D and H).

FIG. 12 shows the results of treating mice bearing U2932 ABC DLBCL xenografts with vehicle (PBS, negative control), IMGN529 (at 10 mg/kg or 5 mg/kg), rituximab (at 10 mg/kg), combinations of IMGN529 and rituximab (at either 10 mg/kg IMGN529 or 5 mg/kg IMGN529), or R-CHOP. T/C % represents tumor growth inhibition. PR indicates partial response. CR indicates complete response.

FIG. 13, panels A-B, show the expression of anti-apoptotic proteins (panel A) and proteins associated with the PI3K/AKT axis (panel B) in DOHH2 and U2932 cells treated with 1 nM IMGN529 and 20 µg/mL rituximab, alone or in combination.

Figure 17:
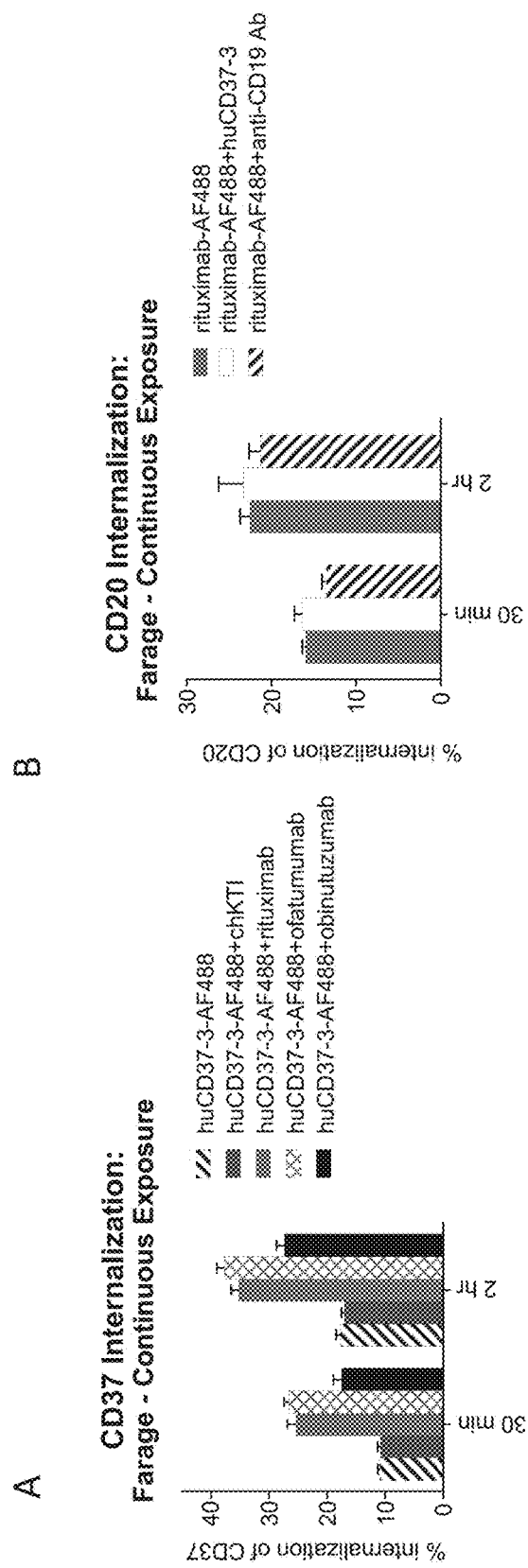

FIG. 17, panels A-B, show the results of internalization of the anti-CD37 antibody huCD37-3 when treated with rituximab and other anti-CD20 antibodies (ofatumumab and obinutuzumab) and rituximab when treated with huCD37-3 antibody and an anti-CD19 antibody.

DETAILED DESCRIPTION OF THE INVENTION

The present invention provides CD37 binding immunoconjugate and CD20 binding antibody combinations and uses thereof.

I. Definitions

To facilitate an understanding of the present invention, a number of terms and phrases are defined below.

The term "CD37" as used herein, refers to any native CD37 polypeptide, unless otherwise indicated. CD37 is also referred to as GP52-40, leukocyte antigen CD37, and Tetraspanin-26. The term "CD37" encompasses "full-length," unprocessed CD37 polypeptide as well as any form or isoform of CD37 polypeptide that results from processing in the cell. The term also encompasses naturally occurring variants of CD37 polypeptide, e.g., those encoded by splice variants and allelic variants. The CD37 polypeptides described herein can be isolated from a variety of sources, such as from human tissue types or from another source, or prepared by recombinant or synthetic methods. Where specifically indicated, "CD37" can be used to refer to a nucleic acid that encodes a CD37 polypeptide.

The term "CD20" as used herein, refers to any native CD20 polypeptide, unless otherwise indicated. CD20 is also referred to as membrane-spanning 4-domains, subfamily A, member 1 (MS4A1), B-lymphocyte surface antigen B1, and Leukocyte surface antigen Leu-16. The term "CD20" encompasses "full-length," unprocessed CD20 polypeptide as well as any form or isoform of CD20 polypeptide that results from processing in the cell. The term also encompasses naturally occurring variants of CD20 polypeptide, e.g., those encoded by splice variants and allelic variants. The CD20 polypeptides described herein can be isolated from a variety of sources, such as from human tissue types or from another source, or prepared by recombinant or synthetic methods. Where specifically indicated, "CD20" can be used to refer to a nucleic acid that encodes a CD20 protein.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, multispecific antibodies such as bispecific antibodies generated from at least two intact antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies.

A "blocking" antibody or an "antagonist" antibody is one which inhibits or reduces biological activity of the antigen it binds, such as CD37 or CD20. In some embodiments, blocking antibodies or antagonist antibodies substantially or completely inhibit the biological activity of the antigen. The biological activity can be reduced by 10%, 20%, 30%, 50%, 70%, 80%, 90%, 95%, or even 100%.

The term "anti-CD37 antibody" or "an antibody that binds to CD37" refers to an antibody that is capable of binding CD37 with sufficient affinity such that the antibody is useful as a diagnostic and/or therapeutic agent in targeting CD37. The extent of binding of an anti-CD37 antibody to an unrelated, non-CD37 protein can be less than about 10% of the binding of the antibody to CD37 as measured, e.g., by a radioimmunoassay (RIA). In certain embodiments, an antibody that binds to CD37 has a dissociation constant (Kd) of ≤1 µM, ≤100 nM, ≤10 nM, ≤1 nM, or ≤0.1 nM. Similarly, the term "anti-CD20 antibody" or "an antibody that binds to CD20" refers to an antibody that is capable of binding CD20 with sufficient affinity such that the antibody is useful as a diagnostic and/or therapeutic agent in targeting CD20. The extent of binding of an anti-CD20 antibody to an unrelated, non-CD20 protein can be less than about 10% of the binding of the antibody to CD20 as measured, e.g., by a radioimmunoassay (RIA). In certain embodiments, an antibody that binds to CD20 has a dissociation constant (Kd) of ≤1 µM, ≤100 nM, ≤10 nM, ≤1 nM, or ≤0.1 nM.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., 1986, *Nature*, 321:522-525; Riechmann et al., 1988, *Nature*, 332:323-327; Verhoeyen et al., 1988, *Science*, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539, Roguska et al., Proc. Natl. Acad. Sci., USA, 91(3):969-973 (1994), and Roguska et al., Protein Eng. 9(10):895-904 (1996). In some embodiments, a "humanized antibody" is a resurfaced antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. *Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
|    |         |         | (Kabat Numbering) |
| H1 | H31-H35 | H26-H35 | H26-H32 |
|    |         |         | (Chothia Numbering) |
| H2 | H50-H65 | H50-H58 | H52-H56 |
| H3 | H95-H102 | H95-H102 | H95-H102 |

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd) Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-CD37 antibody or fragment thereof) and is defined by a generic formula: C-L-A, wherein C=cytotoxin, L=linker, and A=anti-CD37 antibody or antibody fragment. Immunoconjugates can also be defined by the generic formula in reverse order: A-L-C.

The term "IMGN529" refers to the immunoconjugate described herein containing the huCD37-3 antibody (comprising the CDRs represented by SEQ ID NOs:4-9, the VH of SEQ ID NO:12 and the VL of SEQ ID NO:15), the SMCC linker, and the DM1 maytansinoid.

A "linker" is any chemical moiety that is capable of linking a compound, usually a drug, such as a maytansinoid, to a cell-binding agent such as an anti CD37 antibody or a fragment thereof in a stable, covalent manner. Linkers can be susceptible to or be substantially resistant to, e.g., disulfide bond cleavage, at conditions under which the compound or the antibody remains active. Suitable linkers are well known in the art and include, for example, disulfide groups and thioether groups.

The terms "cancer" and "cancerous" refer to or describe the physiological condition in mammals in which a population of cells is characterized by unregulated cell growth. Examples of cancer include, but are not limited to, carcinoma, lymphoma, blastoma, sarcoma, and leukemia. The term "B-cell cancer" refers to or describes the physiological condition in mammals in which a population of B-cells is characterized by unregulated cell growth. "Tumor" and "neoplasm" refer to one or more cells that result from excessive cell growth or proliferation, either benign (non-cancerous) or malignant (cancerous) including pre-cancerous lesions. Examples of "cancer" or "tumorigenic" diseases which can be treated and/or prevented include B-cell lymphomas including NHL, precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma, plasmacytoma, plasma cell myeloma, post-transplant lymphoproliferative disorder, Waldenstrom's macroglobulinemia, acute lymphoblastic leukemia (ALL), and anaplastic large-cell lymphoma (ALCL).

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered serially, by alternation, or in parallel as separate formulations; or (3) by some other regimen. When delivered in alternation therapy, a synergistic effect can be attained when the compounds are administered or delivered sequentially, e.g., by different injections in separate syringes. A "Synergy Score" can be calculated using the formula Synergy Score=$\log f_x \log f_Y \Sigma_{max} (O,I_{data}) (I_{data}-I_{Loewe})$, which is described in more detail below in Example 1.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody or immunoconjugate as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size or burden; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP) or any combination thereof. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

A "chemotherapeutic agent" is a chemical compound useful in the treatment of cancer, regardless of mechanism of action. Chemotherapeutic agents include, for example, cyclophosphamide, doxorubicin, vincristine, prednisone, fludarabine, etoposide, methotrexate, lenalidomide, chlorambucil, bendamustine and/or modified versions of such chemotherapeutics.

The term "respond favorably" generally refers to causing a beneficial state in a subject. With respect to cancer treatment, the term refers to providing a therapeutic effect on the subject. Positive therapeutic effects in cancer can be measured in a number of ways (See, W. A. Weber, J. Nucl. Med. 50:1S-10S (2009)). For example, tumor growth inhibition, molecular marker expression, serum marker expression, and molecular imaging techniques can all be used to assess therapeutic efficacy of an anti-cancer therapeutic. With respect to tumor growth inhibition, according to NCI standards, a T/C ≤42% is the minimum level of anti-tumor activity. A T/C <10% is considered a high anti-tumor activity level, with T/C (%)=Median tumor volume of the treated/Median tumor volume of the control×100. A favorable response can be assessed, for example, by increased progression-free survival (PFS), disease-free survival (DFS), or overall survival (OS), complete response (CR), partial response (PR), or, in some cases, stable disease (SD), a decrease in progressive disease (PD), a reduced time to progression (TTP) or any combination thereof.

PFS, DFS, and OS can be measured by standards set by the National Cancer Institute and the U.S. Food and Drug Administration for the approval of new drugs. See Johnson et al, (2003) J. Clin. Oncol. 21(7):1404-1411.

"Progression free survival" (PFS) refers to the time from enrollment to disease progression or death. PFS is generally measured using the Kaplan-Meier method and Response Evaluation Criteria in Solid Tumors (RECIST) 1.1 standards. Generally, progression free survival refers to the situation wherein a patient remains alive, without the cancer getting worse.

"Time to Tumor Progression" (TTP) is defined as the time from enrollment to disease progression. TTP is generally measured using the RECIST 1.1 criteria.

A "complete response" or "complete remission" or "CR" indicates the disappearance of all signs of tumor or cancer in response to treatment. This does not always mean the cancer has been cured.

A "partial response" or "PR" refers to a decrease in the size or volume of one or more tumors or lesions, or in the extent of cancer in the body, in response to treatment.

"Stable disease" refers to disease without progression or relapse. In stable disease there is neither sufficient tumor shrinkage to qualify for partial response nor sufficient tumor increase to qualify as progressive disease.

"Progressive disease" refers to the appearance of one more new lesions or tumors and/or the unequivocal progression of existing non-target lesions. Progressive disease can also refer to a tumor growth of more than 20 percent since treatment began, either due to an increases in mass or in spread of the tumor.

"Disease free survival" (DFS) refers to the length of time during and after treatment that the patient remains free of disease.

"Overall Survival" (OS) refers to the time from patient enrollment to death or censored at the date last known alive. OS includes a prolongation in life expectancy as compared to naive or untreated individuals or patients. Overall survival refers to the situation wherein a patient remains alive for a defined period of time, such as one year, five years, etc., e.g., from the time of diagnosis or treatment.

The term "overexpression" of CD37 or CD20 in a particular tumor, tissue, or cell sample refers to CD37 or CD20 (a CD37 or CD20 polypeptide or a nucleic acid encoding such a polypeptide) that is present at a level higher than that which is present in non-diseased tissue or cells of the same type or origin. Such overexpression can be caused, for example, by mutation, gene amplification, increased transcription, or increased translation.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor burden; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

Prophylactic or preventative measures refer to measures that prevent and/or slow the development of a targeted pathological condition or disorder. Thus, those in need of prophylactic or preventative measures include those prone to have the disorder and those in whom the disorder is to be prevented.

The term "instructing" means providing directions for applicable therapy, medication, treatment, treatment regimens, and the like, by any means, for example, in writing, such as in the form of package inserts or other written promotional material.

The terms "pre-treat" and "pre-treatment" refer to therapeutic measures that occur prior to the administration of an anti-CD37 therapeutic and/or an anti-CD20 therapeutic. For example, as described in more detail herein, a prophylactic such as a steroid (e.g., corticosteroid) can be administered within about a week, about five days, about three days, about two days, or about one day or 24 hours prior to the administration of the anti-CD37 therapeutic and/or an anti-CD20 therapeutic. The prophylactic can also be administered prior to the anti-CD37 therapeutic and/or anti-CD20 therapeutic on the same day as the anti-CD37 therapeutic and/or an anti-CD20 therapeutic.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, *Proc. Natl. Acad. Sci.,* 87:2264-2268, as modified in Karlin et al., 1993, *Proc. Natl. Acad. Sci.,* 90:5873-5877, and incorporated into the NBLAST and XBLAST programs (Altschul et al., 1991, *Nucleic Acids Res.,* 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology,* 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgap-dna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the invention do not abrogate the binding of the polypeptide or antibody containing the amino acid sequence, to the antigen(s), i.e., the CD37 or CD20 to which the polypeptide or antibody binds. Methods of identifying nucleotide and amino acid conservative substitutions which do not eliminate antigen binding are well-known in the art (see, e.g., Brummell et al., *Biochem.* 32: 1180-1 187 (1993); Kobayashi et al. *Protein Eng.* 12(10):879-884 (1999); and Burks et al. *Proc. Natl. Acad. Sci. USA* 94:412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II Anti-CD37 Immunoconjugates

The methods described herein provide methods of administering immunoconjugates that specifically bind CD37 (e.g., IMGN529). These agents are referred to herein as "CD37-immunoconjugates or anti-CD37 immunoconjugates." The full-length amino acid sequences for human, macaque, and murine CD37 are known in the art and also provided herein as represented by SEQ ID NOs:1-3, respectively.

```
Human CD37:
                                          (SEQ ID NO: 1)
MSAQESCLSLIKYFLFVFNLFFFVLGSLIFCFGIWILIDKTSFVSFVGLA

FVPLQIWSKVLAISGIFTMGIALLGCVGALKELRCLLGLYFGMLLLLFAT

QITLGILISTQRAQLERSLRDVVEKTIQKYGTNPEETAAEESWDYVQFQL

RCCGWHYPQDWFQVLILRGNGSEAHRVPCSCYNLSATNDSTILDKVILPQ

LSRLGHLARSRHSADICAVPAESHIYREGCAQGLQKWLHNNLISIVGICL

GVGLLELGFMTLSIFLCRNLDHVYNRLAYR

Macaque CD37:
                                          (SEQ ID NO: 2)
MSAQESCLSLIKYFLFVFNLFFFVILGSLIFCFGIWILIDKTSFVSFVGL

AFVPLQIWSKVLAISGVFTMGLALLGCVGALKELRCLLGLYFGMLLLLFA

TQITLGILISTQRAQLERSLQDIVEKTIQRYHTNPEETAAEESWDYVQFQ

LRCCGWHSPQDWFQVLTLRGNGSEAHRVPCSCYNLSATNDSTILDKVILP

QLSRLGQLARSRHSTDICAVPANSHIYREGCARSLQKWLHNNLISIVGIC

LGVGLLELGFMTLSIFLCRNLDHVYNRLRYR

Murine CD37 (NP_031671):
                                          (SEQ ID NO: 3)
MSAQESCLSLIKYFLFVFNLFFFVLGGLIFCFGTWILIDKTSFVSFVGLS

FVPLQTWSKVLAVSGVLTMALALLGCVGALKELRCLLGLYFGMLLLLFAT

QITLGILISTQRVRLERRVQELVLRTIQSYRTNPDETAAEESWDYAQFQL
```

```
-continued
RCCGWQSPRDWNKAQMLKANESEEPFVPCSCYNSTATNDSTVFDKLFFSQ

LSRLGPRAKLRQTADICALPAKAHIYREGCAQSLQKWLHNNIISIVGICL

GVGLLELGFMTLSIFLCRNLDHVYDRLARYR
```

In certain embodiments, an anti-CD37 immunoconjugate (e.g., IMGN529) contains a CD37-binding agent that is an antibody, e.g., a humanized antibody.

In certain embodiments, the CD37-binding agents (e.g., IMGN529) have one or more of the following effects: inhibit proliferation of tumor cells, reduce the tumorigenicity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells.

In certain embodiments, immunoconjugates or other agents that specifically bind human CD37 trigger (e.g., IMGN529) cell death via a cytotoxic agent. For example, in certain embodiments, an antibody to a human CD37 antibody is conjugated to a maytansinoid that is activated in tumor cells expressing the CD37 by protein internalization. In certain alternative embodiments, the agent or antibody is not conjugated.

In certain embodiments, the CD37-binding agents (e.g., IMGN529) are capable of inhibiting tumor growth. In certain embodiments, the CD37-binding agents are capable of inhibiting tumor growth in vivo (e.g., in a xenograft mouse model and/or in a human having cancer).

The CD37-binding agents include the antibody huCD37-3 and fragments, variants and derivatives thereof, as described previously in U.S. Publication No. 2011/0256153, which is herein incorporated by reference in its entirety. The CD37-binding agents also include CD37-binding agents that specifically bind to the same CD37 epitope as huCD37-3. The CD37-binding agents also include CD37-binding agents that competitively inhibit huCD37-3.

The CD37-binding agents also include CD37-binding agents that comprise the heavy and light chain CDR sequences of huCD37-3. The CDR sequences of huCD37-3 are described in Tables 1 and 2 below.

TABLE 1

Variable heavy chain CDR amino acid sequences

| Antibody | VH-CDR1 | VH-CDR2 | VH-CDR3 |
|---|---|---|---|
| CD37-3 | TSGVS (SEQ ID NO: 4) | VIWGDGSTN (SEQ ID NO: 5) | GGYSLAH (SEQ ID NO: 6) |

TABLE 2

Variable light chain CDR amino acid sequences

| Antibody | VL-CDR1 | VL-CDR2 | VL-CDR3 |
|---|---|---|---|
| CD37-3 | RASENIRSNLA (SEQ ID NO: 7) | VATNLAD (SEQ ID NO: 8) | QHYWGTTWT (SEQ ID NO: 9) |

The CD37 binding molecules can be antibodies or antigen binding fragments that specifically bind to CD37 that comprise the CDRs of murine, chimeric, or humanized CD37-3 with up to four (i.e. 0, 1, 2, 3, or 4) conservative amino acid substitutions per CDR. In some embodiments, the CD37-binding agents comprise variable heavy chain CDR1, CDR2, and CDR3 sequences comprising SEQ ID NOs: 4, 5, and 6 and variable light chain CDR1, CDR2, and CDR3 sequences comprising SEQ ID NOs: 7, 8, and 9.

Polypeptides can comprise the variable light chains or variable heavy chains described herein. Antibodies and polypeptides can also comprise both a variable light chain and a variable heavy chain. The variable light chain and variable heavy chain sequences of murine, chimeric, and humanized CD37-3 antibodies are provided in Tables 3 and 4 below.

ments, the antibody or antigen-binding fragment thereof comprises (a) a VH polypeptide having at least about 95% sequence identity to one of SEQ ID NOs:10-12 and 22, and (b) a VL polypeptide having at least about 95% sequence identity to one of SEQ ID NOs:13-15. In certain embodiments, the antibody or antigen-binding fragment comprises (a) a VH polypeptide having the amino acid sequence of one of SEQ ID NOs:10-12 and 22; and (b) a VL polypeptide having the amino acid sequence of one of SEQ ID NOs:13-15. In certain embodiments, the antibody or antigen-binding fragment specifically binds CD37. In certain embodiments, the antibody or antigen-binding fragment is a murine, chimeric, or humanized antibody that specifically binds CD37. In certain embodiments, the antibody or antigen-binding fragment is a human antibody that specifically binds CD37. In certain embodiments, the antibody or antigen-binding

TABLE 3

Anti-CD37 Variable heavy chain amino acid sequences

| CD37 Antibody | VH Amino Acid Sequence (SEQ ID NO) |
|---|---|
| muCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSA (SEQ ID NO: 10) |
| chCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSA (SEQ ID NO: 11) |
| huCD37-3 (version 1.0) | QVQVQESGPGLVAPSQTLSITCTVSGFSLTTSGVSWVRQPPGKGLEWLGVIW GDGSTNYHPSLKSRLSIKKDHSKSQVFLKLNSLTAADTATYYCAKGGYSLA HWGQGTLVTVSS (SEQ ID NO: 12) |
| huCD37-3 (version 1.1) | QVQVQESGPGLVAPSQTLSITCTVSGFSLTTSGVSWVRQPPGKGLEWLGVIW GDGSTNYHSSLKSRLSIKKDHSKSQVFLKLNSLTAADTATYYCAKGGYSLA HWGQGTLVTVSS (SEQ ID NO: 22) |

TABLE 4

Anti-CD37 Variable light chain amino acid sequences

| CD37 Antibody | VL Amino Acid Sequence (SEQ ID NO) |
|---|---|
| muCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKR (SEQ ID NO: 13) |
| chCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKR (SEQ ID NO: 14) |
| huCD37-3 (v1.0 and v1.1) | DIQMTQSPSSLSVSVGERVTITCRASENIRSNLAWYQQKPGKSPKLLVNVAT NLADGVPSRFSGSGSGTDYSLKINSLQPEDFGTYYCQHYWGTTWTFGQGTK LEIKR (SEQ ID NO: 15) |

Also provided are antibodies and antigen-binding fragments thereof that comprise: (a) a VH polypeptide having at least about 90% sequence identity to one of SEQ ID NOs: 10-12 and 22; and/or (b) a VL polypeptide having at least about 90% sequence identity to one of SEQ ID NOs:13-15. In certain embodiments, the antibody or antigen-binding fragment thereof comprises (a) a VH polypeptide having at least about 95%, at least about 96%, at least about 97%, at least about 98%, or at least about 99% sequence identity to one of SEQ ID NOs:10-12 and 22 and (b) a VL polypeptide having at least about 95%, at least about 96%, at least about 97%, at least about 98%, or at least about 99% sequence identity to one of SEQ ID NOs:13-15. In certain embodifragment containing polypeptides having a certain percentage of sequence identity to SEQ ID NOs:10-12 and 22 and 13-15 differs from SEQ ID NOs:10-12 and 13-15 by conservative amino acid substitutions only.

Antibodies and antigen-binding fragments thereof can also comprise both a light chain and a heavy chain. The light chain and variable chain sequences of murine, chimeric, and humanized CD37-3 antibodies are provided in Tables 5 and 6 below.

TABLE 5

Full-length heavy chain amino acid sequences

| Antibody | Full-Length Heavy Chain Amino Acid Sequence (SEQ ID NO) |
| --- | --- |
| muCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSAAKTTAPSVYPLAPVCGDTTGSSVTLGCLVKGYFPEPVTL TWNSGSLSSGVHTFPAVLQSDLYTLSSSVTVTSSTWPSQSITCNVAHPASSTK VDKKIEPRGPTIKPCPPCKCPAPNLLGGPSVFIFPPKIKDVLMISLSPIVTCVVV DVSEDDPDVQISWFVNNVEVHTAQTQTHREDYNSTLRVVSALPIQHQDWM SGKEFKCKVNNKDLPAPIERTISKPKGSVRAPQVYVLPPPEEEMTKKQVTLT CMVTDFMPEDIYVEWTNNGKTELNYKNTEPVLDSDGSYFMYSKLRVEKKN WVERNSYSCSVVHEGLHNHEITTKSFSRTPGK (SEQ ID NO: 16) |
| chCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSAASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPGK (SEQ ID NO: 17) |
| huCD37-3 v1.0 | QVQVQESGPGLVAPSQTLSITCTVSGFSLTTSGVSWVRQPPGKGLEWLGVIW GDGSTNYHPSLKSRLSIKKDHSKSQVFLKLNSLTAADTATYYCAKGGYSLA HWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPG (SEQ ID NO: 18) |
| huCD37-3 v1.1 | QVQVQESGPGLVAPSQTLSITCTVSGFSLTTSGVSWVRQPPGKGLEWLGVIW GDGSTNYHSSLKSRLSIKKDHSKSQVFLKLNSLTAADTATYYCAKGGYSLA HWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPG (SEQ ID NO: 37) |

TABLE 6

Full-length light chain amino acid sequences

| Antibody | Full-length Light Chain Amino Acid Sequence (SEQ ID NO) |
| --- | --- |
| muCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKRADAAPTVSIFPPSSEQLTSGGASVVCFLNNFYPKDINVKWKIDGSERQ NGVLNSWTDQDSKDSTYSMSSTLTLTKDEYERHNSYTCEATHKTSTSPIVKS FNRNEC (SEQ ID NO: 19) |
| chCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGEC (SEQ ID NO: 20) |
| huCD37-3 (v1.0 and v1.1) | DIQMTQSPSSLSVSVGERVTITCRASENIRSNLAWYQQKPGKSPKLLVNVAT NLADGVPSRFSGSGSGTDYSLKINSLQPEDFGTYYCQHYWGTTWTFGQGTK LEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGEC (SEQ ID NO: 21) |

Also provided are antibodies and antigen-binding fragments thereof that comprise: (a) a polypeptide having at least about 90% sequence identity to one of SEQ ID NOs: 16-18 and 37; and (b) a polypeptide having at least about 90% sequence identity to one of SEQ ID NOs:19-21. In certain embodiments, the antibody or antigen-binding fragment thereof comprises a polypeptide having at least about 95%, at least about 96%, at least about 97%, at least about 98%, or at least about 99% sequence identity to one of SEQ ID NOs:16-18 and 37 and a polypeptide having at least about 95%, at least about 96%, at least about 97%, at least about 98%, or at least about 99% sequence identity to one of SEQ ID NOs:19-21. Thus, in certain embodiments, the antibody or antigen-binding fragment comprises (a) a polypeptide having at least about 95% sequence identity to one of SEQ ID NOs:16-18 and 37, and/or (b) a polypeptide having at least about 95% sequence identity to one of SEQ ID NOs:19-21. In certain embodiments, the antibody or antigen-binding fragment comprises (a) a polypeptide having the amino acid sequence of one of SEQ ID NOs:16-18 and 37; and/or (b) a polypeptide having the amino acid sequence of one of SEQ ID NOs:19-21. In certain embodiments, the antibody or antigen-binding fragment thereof is a murine, chimeric, or humanized antibody or fragment that specifically binds CD37. In certain embodiments, the antibody or antigen-binding fragment thereof comprises polypeptides differing from SEQ ID NOs:16-18 and 37 and 19-21 by conservative amino acid substitutions only.

In certain embodiments, the CD37 antibody can be the antibody produced from a hybridoma selected from the group consisting of ATCC Deposit Designation PTA-10664, deposited with the American Type Culture Collection (ATCC), located at 10801 University Boulevard, Manassas, Va. 20110, on Feb. 18, 2010. In certain embodiments, the antibody comprises the VH-CDRs and the VL-CDRS of the antibody produced from a hybridoma selected from the group consisting of PTA-10664.

In certain embodiments, the CD37 antibody can comprise a light chain encoded by the recombinant plasmid DNA phuCD37-3LC (ATCC Deposit Designation PTA-10722, deposited with the ATCC on Mar. 18, 2010). In certain embodiments, the CD37 antibody can comprise a heavy chain encoded by the recombinant plasmid DNA phuCD37-3HCv.1.0 (ATCC Deposit Designation PTA-10723, deposited with the ATCC on Mar. 18, 2010). In certain embodiments, the CD37 antibody can comprise a light chain encoded by the recombinant plasmid DNA phuCD37-3LC (PTA-10722) and a heavy chain encoded by the recombinant plasmid DNA phuCD37-3HCv.1.0 (PTA-10723). In certain embodiments, the CD37 antibody can comprise the VL-CDRs encoded by the recombinant plasmid DNA phuCD37-3LC (PTA-10722) and the VH-CDRs encoded by the recombinant plasmid DNA phuCD37-3HCv.1.0 (PTA-10723).

Methods known in the art for purifying antibodies and other proteins also include, for example, those described in U.S. Patent Publication No. 2008/0312425, 2008/0177048, and 2009/0187005, each of which is hereby incorporated by reference herein in its entirety.

Conjugates comprising the anti-CD37 antibodies, antibody fragments, and their functional equivalents as disclosed herein, linked or conjugated to a drug or prodrug (also referred to herein as immunoconjugates) are also described herein. Suitable drugs or prodrugs are known in the art. The drugs or prodrugs can be cytotoxic agents. The cytotoxic agent used in the cytotoxic conjugate of the present invention can be any compound that results in the death of a cell, or induces cell death, or in some manner decreases cell viability, and includes, for example, maytansinoids and maytansinoid analogs. Such conjugates can be prepared by using a linking group in order to link a drug or prodrug to the antibody or functional equivalent. Suitable linking groups are well known in the art and include, for example, disulfide groups and thioether groups.

The drug or prodrug can, for example, be linked to the anti-CD37 antibody or fragment thereof through a disulfide bond. The linker molecule or crosslinking agent comprises a reactive chemical group that can react with the anti-CD37 antibody or fragment thereof. The reactive chemical groups for reaction with the cell-binding agent can be N-succinimidyl esters and N-sulfosuccinimidyl esters. Additionally the linker molecule comprises a reactive chemical group, which can be a dithiopyridyl group that can react with the drug to form a disulfide bond. Linker molecules include, for example, N-succinimidyl 3-(2-pyridyldithio) propionate (SPDP) (see, e.g., Carlsson et al., *Biochem. J.*, 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)2-sulfobutanoate (sulfo-SPDB) (see US Publication No. 20090274713), N-succinimidyl 4-(2-pyridyldithio) pentanoate (SPP) (see, e.g., CAS Registry number 341498-08-6), 2-iminothiolane, or acetylsuccinic anhydride. For example, the antibody or cell binding agent can be modified with crosslinking reagents and the antibody or cell binding agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration.

Antibody-maytansinoid conjugates with non-cleavable linkers can also be prepared. Such crosslinkers are described in the art (see US Publication No. 2005/0169933) and include but are not limited to, N-succinimidyl 4-(maleimidomethyl) cyclohexanecarboxylate (SMCC). In some embodiments, the antibody is modified with crosslinking reagents such as succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)). The modified antibody is then reacted with the thiol-containing maytansinoid derivative to produce a conjugate. The conjugate can be purified by gel filtration through a Sephadex G25 column or by dialysis or tangential flow filtration. The modified antibodies are treated with the thiol-containing maytansinoid (1 to 2 molar equivalent/maleimido group) and antibody-maytansinoid conjugates are purified by gel filtration through a Sephadex G-25 column, chromatography on a ceramic hydroxyapatite column, dialysis or tangential flow filtration or a combination of methods thereof. Typically, an average of 1-10 maytansinoids per antibody are linked. One method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result. Maytansinoid conjugates of antibodies, antibody fragments, and other proteins are made in the same way.

In some embodiments, the linker is a linker containing at least one charged group as described, for example, in U.S. Patent Publication No. 2012/0282282, the contents of which are entirely incorporated herein by reference. In some embodiments, the charged or pro-charged cross-linkers are those containing sulfonate, phosphate, carboxyl or quaternary amine substituents that significantly increase the solubility of the modified cell-binding agent and the cell-binding agent-drug conjugates, especially for monoclonal antibody-drug conjugates with 2 to 20 drugs/antibody linked. Conjugates prepared from linkers containing a pro-charged moiety would produce one or more charged moieties after the conjugate is metabolized in a cell. In some embodiments, the linker is selected from the group consisting of: N-succinimidyl 4-(2-pyridyldithio)-2-sulfopentanoate (sulfo-SPP) and N-succinimidyl 4-(2-pyridyldithio)-2-sulfobutanoate (sulfo-SPDB).

Many of the linkers disclosed herein are described in detail in U.S. Patent Publication Nos. 2005/0169933, 2009/0274713, and 2012/0282282, and in WO2009/134977; the contents of which are entirely incorporated herein by reference.

The present invention includes aspects wherein about 2 to about 8 drug molecules ("drug load"), for example, maytansinoid, are linked to an anti-CD37 antibody or fragment thereof, the anti-tumor effect of the conjugate is much more efficacious as compared to a drug load of a lesser or higher number of drugs linked to the same cell binding agent. "Drug load", as used herein, refers to the number of drug molecules (e.g., a maytansinoid) that can be attached to a cell binding agent (e.g., an anti-CD37 antibody or fragment thereof). In one aspect the number of drug molecules that can be attached to a cell binding agent can average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). $N^{2'}$-deacetyl-$N^{2'}$-(3-mercapto-1-oxopropyl)-maytansine (DM1) can be used.

The anti-CD37 antibody or fragment thereof can be modified by reacting a bifunctional crosslinking reagent with the anti-CD37 antibody or fragment thereof, thereby resulting in the covalent attachment of a linker molecule to the anti-CD37 antibody or fragment thereof. As used herein, a "bifunctional crosslinking reagent" is any chemical moiety that covalently links a cell-binding agent to a drug, such as the drugs described herein. In another method, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

Thus, in one aspect, an immunoconjugate comprises 1 maytansinoid per antibody. In another aspect, an immunoconjugate comprises 2 maytansinoids per antibody. In another aspect, an immunoconjugate comprises 3 maytansinoids per antibody. In another aspect, an immunoconjugate comprises 4 maytansinoids per antibody. In another aspect, an immunoconjugate comprises 5 maytansinoids per antibody. In another aspect, an immunoconjugate comprises 6 maytansinoids per antibody. In another aspect, an immunoconjugate comprises 7 maytansinoids per antibody. In another aspect, an immunoconjugate comprises 8 maytansinoids per antibody.

In one aspect, an immunoconjugate comprises about 1 to about 8 maytansinoids per antibody. In another aspect, an immunoconjugate comprises about 2 to about 7 maytansinoids per antibody. In another aspect, an immunoconjugate comprises about 2 to about 6 maytansinoids per antibody. In another aspect, an immunoconjugate comprises about 2 to about 5 maytansinoids per antibody. In another aspect, an immunoconjugate comprises about 3 to about 5 maytansinoids per antibody. In another aspect, an immunoconjugate comprises about 3 to about 4 maytansinoids per antibody.

In one aspect, a composition comprising immunoconjugates has an average of about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1) drug molecules (e.g., maytansinoids) attached per antibody. In one aspect, a composition comprising immunoconjugates has an average of about 1 to about 8 drug molecules (e.g., maytansinoids) per antibody. In one aspect, a composition comprising immunoconjugates has an average of about 2 to about 7 drug molecules (e.g., maytansinoids) per antibody. In one aspect, a composition comprising immunoconjugates has an average of about 2 to about 6 drug molecules (e.g., maytansinoids) per antibody. In one aspect, a composition comprising immunoconjugates has an average of about 2 to about 5 drug molecules (e.g., maytansinoids) per antibody. In one aspect, a composition comprising immunoconjugates has an average of about 3 to about 5 drug molecules (e.g., maytansinoids) per antibody. In one aspect, a composition comprising immunoconjugates has an average of about 3 to about 4 drug molecules (e.g., maytansinoids) per antibody.

In one aspect, a composition comprising immunoconjugates has an average of about 2±0.5, about 3±0.5, about 4±0.5, about 5±0.5, about 6±0.5, about 7±0.5, or about 8±0.5 drug molecules (e.g., maytansinoids) attached per antibody. In one aspect, a composition comprising immunoconjugates has an average of about 3.5±0.5 drug molecules (e.g., maytansinoids) per antibody.

The drug molecules can also be linked to the antibody molecules through an intermediary carrier molecule such as serum albumin.

As used herein, the expression "linked to a cell-binding agent" or "linked to an anti-CD37 antibody or fragment" refers to the conjugate molecule comprising at least one drug derivative bound to a cell-binding agent anti-CD37 antibody or fragment via a suitable linking group, or a precursor thereof. One linking group is SMCC.

In certain embodiments, cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

In a certain embodiment, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (I):

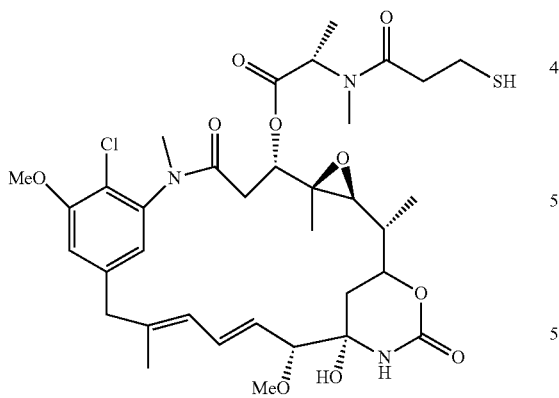

(I)

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula (II):

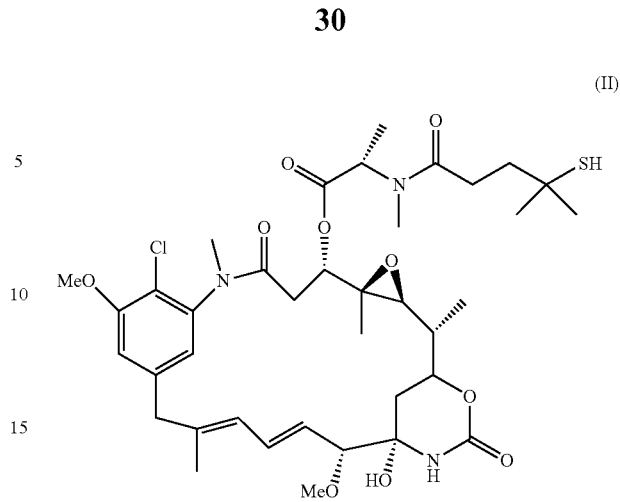

(II)

Another maytansinoid comprising a side chain that contains a sterically hindered thiol bond is $N^{2'}$-deacetyl-N-$^{2'}$(4-mercapto-1-oxopentyl)-maytansine (termed DM3), represented by the following structural formula (III):

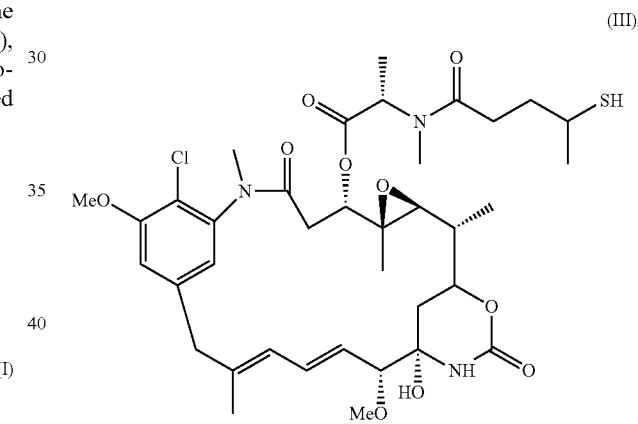

(III)

Each of the maytansinoids taught in U.S. Pat. Nos. 5,208,020 and 7,276,497, can also be used in the conjugate of the present invention. In this regard, the entire disclosure of U.S. Pat. Nos. 5,208,020 and 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety.

Structural representations of some conjugates are shown below:

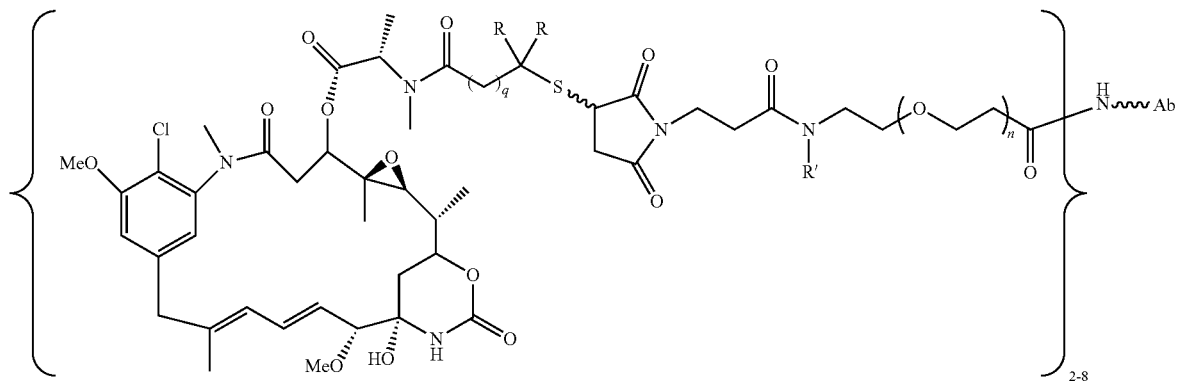
Ab-PEG-Mal-DM1/DM4
DM1: R = H, q = 1
DM4: R = CH₃, q = 2
n = 1-24
Ab = Antibody
R' = H or Me
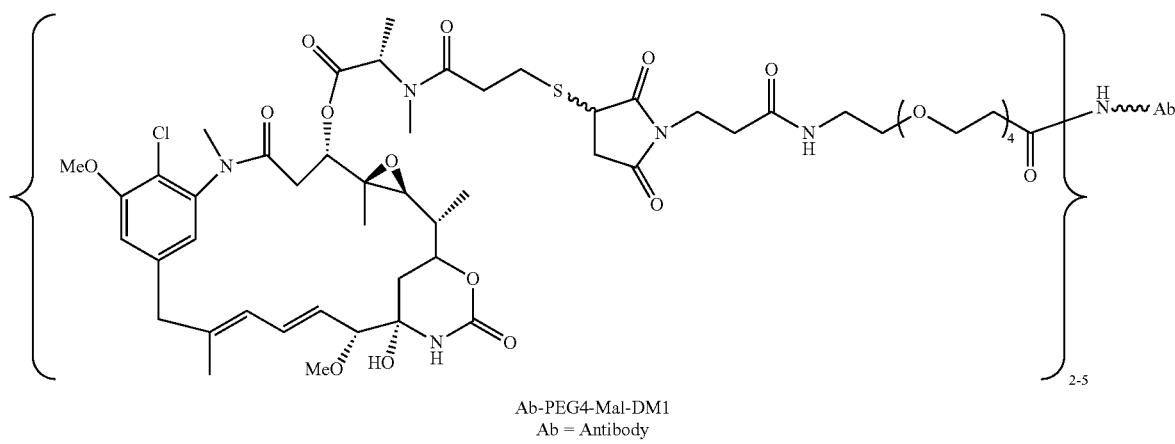
Ab-PEG4-Mal-DM1
Ab = Antibody
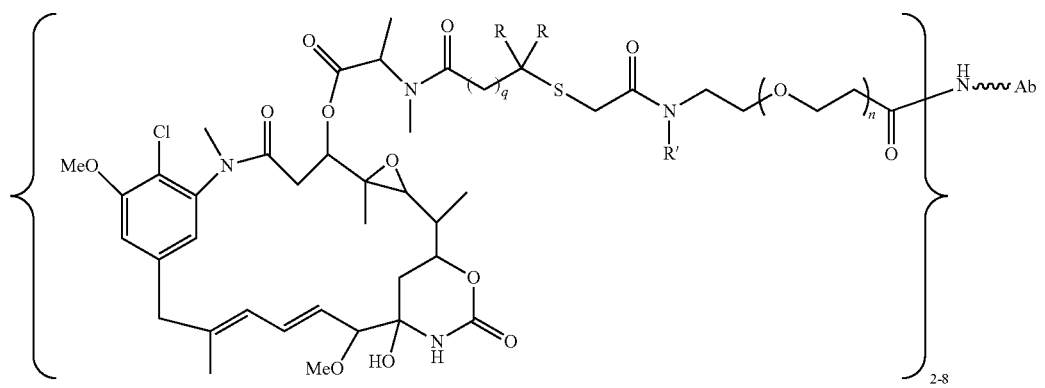
Ab-PEG-SIA-DM1/DM4
DM1: R = H, q = 1
DM4: R = CH₃, q = 2
n = 1-24
Ab = Antibody
R' = H or Me

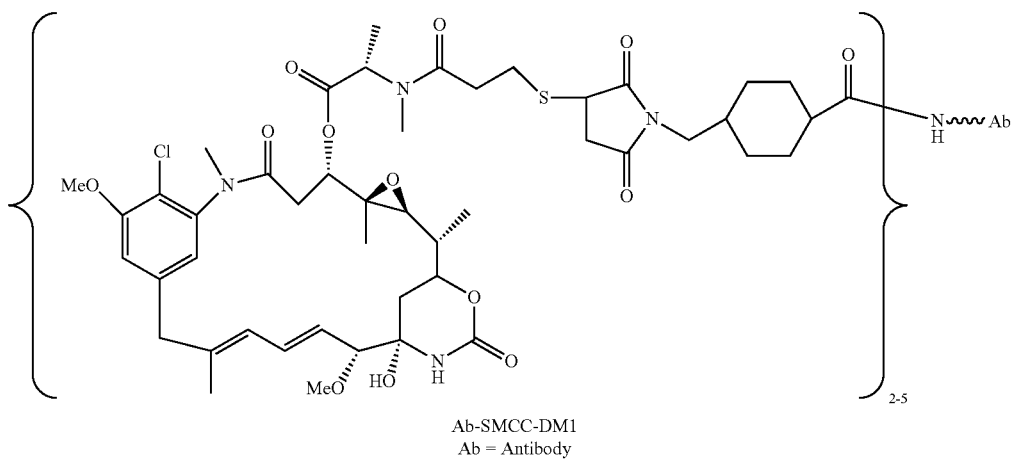
Ab-SMCC-DM1
Ab = Antibody
(VII)
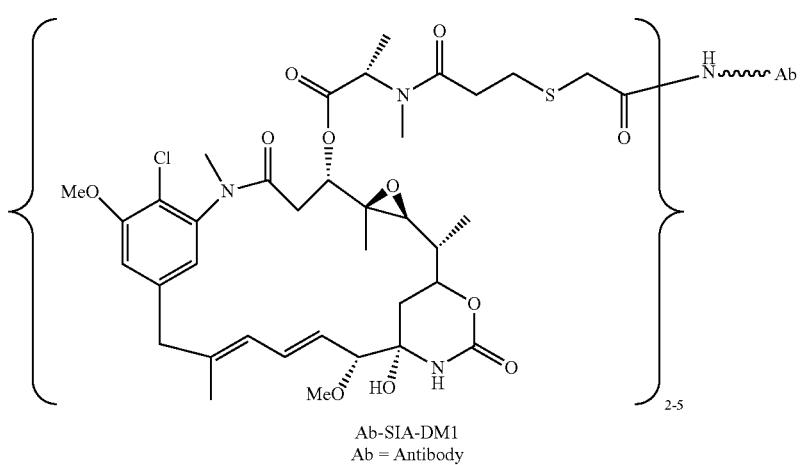
Ab-SIA-DM1
Ab = Antibody
(VIII)
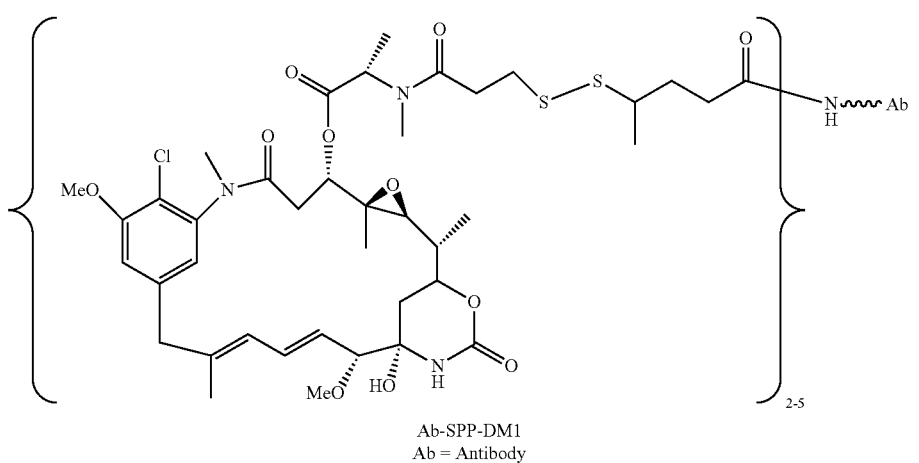
Ab-SPP-DM1
Ab = Antibody
(IX)

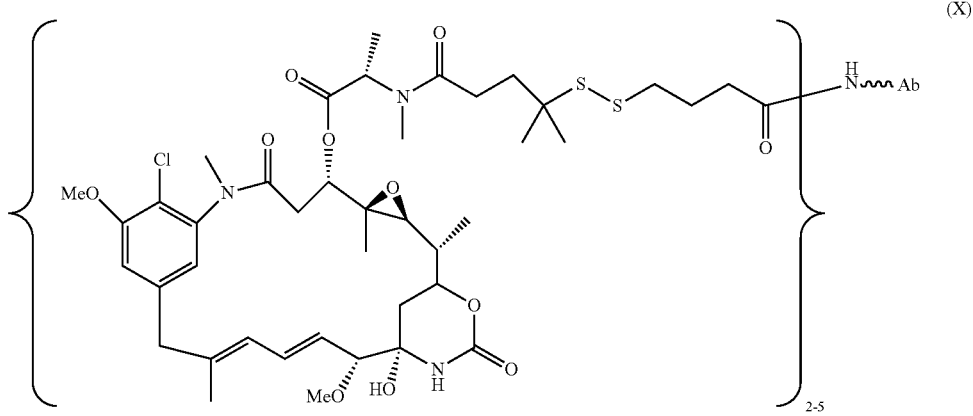

Ab-SPDB-DM4
Ab = Antibody

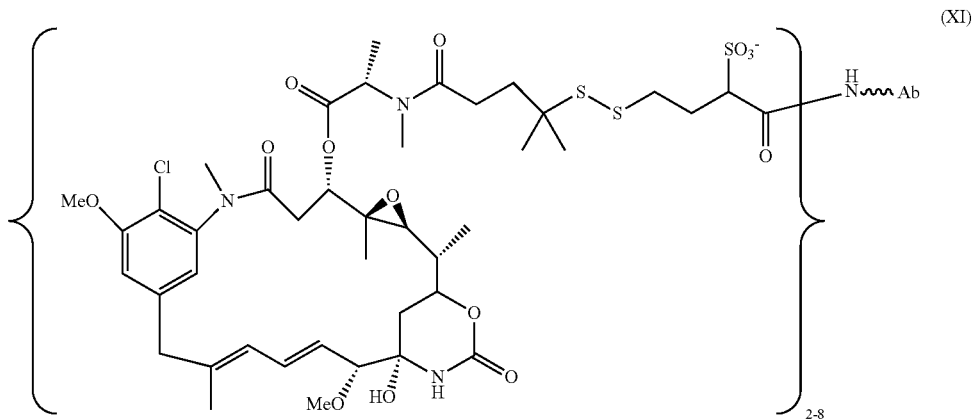

Ab-sulfo-SPDB-DM4
Ab = Antibody

Also included in the present invention are any stereoisomers and mixtures thereof for any compounds or conjugates depicted by any structures above.

Several descriptions for producing such antibody-maytansinoid conjugates are provided in U.S. Pat. Nos. 6,333,410, 6,441,163, 6,716,821, and 7,368,565, each of which is incorporated herein in its entirety.

In general, a solution of an antibody in aqueous buffer can be incubated with a molar excess of maytansinoids having a disulfide moiety that bears a reactive group. The reaction mixture can be quenched by addition of excess amine (such as ethanolamine, taurine, etc.). The maytansinoid-antibody conjugate can then be purified by gel filtration.

The number of maytansinoid molecules bound per antibody molecule can be determined by measuring spectrophotometrically the ratio of the absorbance at 252 nm and 280 nm. The average number of maytansinoid molecules/antibody can be, for example, 1-10 or 2-5. The average number of maytansinoid molecules/antibody can be, for example about 3 to about 4. The average number of maytansinoid molecules/antibody can be about 3.5.

Conjugates of antibodies with maytansinoid or other drugs can be evaluated for their ability to suppress proliferation of various unwanted cell lines in vitro. For example, cell lines such as the human lymphoma cell line Daudi and the human lymphoma cell line Ramos, can easily be used for the assessment of cytotoxicity of these compounds. Cells to be evaluated can be exposed to the compounds for 4 to 5 days and the surviving fractions of cells measured in direct assays by known methods. $IC_{50}$ values can then be calculated from the results of the assays.

The immunoconjugates can, according to some embodiments described herein, be internalized into cells. The immunoconjugate, therefore, can exert a therapeutic effect when it is taken up by, or internalized, by a CD37-expressing cell. In some particular embodiments, the immunoconjugate comprises an antibody, antibody fragment, or polypeptide, linked to a cytotoxic agent by a cleavable linker, and the cytotoxic agent is cleaved from the antibody, antibody fragment, or polypeptide, wherein it is internalized by a CD37-expressing cell.

II. CD20-Binding Agents

The methods described herein provide methods of administering agents that specifically bind CD20. These agents are referred to herein as "CD20-binding agents." A full-length amino acid sequences for human CD20 is provided herein as SEQ ID NO:36:

```
                                            (SEQ ID NO: 36)
MTTPRNSVNGTFPAEPMKGPIAMQSGPKPLFRRMSSLVGPTQSFFMRESK

TLGAVQIMNGLFHIALGGLLMIPAGIYAPICVTVWYPLWGGIMYIISGSL
```

-continued
LAATEKNSRKCLVKGKMIMNSLSLFAAISGMILSIMDILNIKISHFLKME

SLNFIRAHTPYINIYNCEPANPSEKNSPSTQYCYSIQSLFLGILSVMLIF

AFFQELVIAGIVENEWKRTCSRPKSNIVLLSAEEKKEQTIEIKEEVVGLT

ETSSQPKNEEDIEIIPIQEEEEEETETNFPEPPQDQESSPIENDSSP.

In certain embodiments, the CD20-binding agents have one or more of the following effects: inhibit proliferation of tumor cells, reduce the tumorigenicity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells.

In certain embodiments, the CD20-binding agents are capable of inhibiting tumor growth. In certain embodiments, the CD20-binding agents are capable of inhibiting tumor growth in vivo (e.g., in a xenograft mouse model and/or in a human having cancer).

Anti-CD20 antibodies and antigen-binding fragments thereof can comprise polypeptides comprising the variable light chains or variable heavy chains described herein. Anti-CD20 antibodies and polypeptides can also comprise both a variable light chain and a variable heavy chain. The variable light chain and variable heavy chain sequences of anti-CD20 antibodies are provided in Tables 7 and 8 below.

TABLE 7

Anti-CD20 Variable heavy chain amino acid sequences

| CD20 Antibody | VH Amino Acid Sequence (SEQ ID NO) |
|---|---|
| Veltuzumab | QVQLQQSGAEVKKPGSSVKVSCKASGYTFTSYNMEIWVKQAPGQGLEWIG AIYPGNGDTSYNQKFKGKATLTADESTNTAYMELSSLRSEDTAFYYCARST YYGGDWYFDVWGQGTTVTVSSA (SEQ ID NO: 23) |
| Rituximab | QVQLQQPGAELVKPGASVKMSCKASGYTFTSYNMEIWVKQTPGRGLEWIG AIYPGNGDTSYNQKFKGKATLTADKSSSTAYMQLSSLTSEDSAVYYCARST YYGGDWYFNVWGAGTTVTVSA (SEQ ID NO: 24) |
| Ofatumumab | EVQLVESGGGLVQPGRSLRLSCAASGFTFNDYAMEIWVRQAPGKGLEWVST ISWNSGSIGYADSVKGRFTISRDNAKKSLYLQMNSLRAEDTALYYCAKDIQ YGNYYYGMDVWGQGTTVTVSS (SEQ ID NO: 25) |
| Obinutuzumab | QVQLVQSGAEVKKPGSSVKVSCKASGYAFSYSWINWVRQAPGQGLEWMG RIFPGDGDTDYNGKFKGRVTITADKSTSTAYMELSSLRSEDTAVYYCARNV FDGYWLVYWGQGTLVTVSS (SEQ ID NO: 26) |
| huCD20-4 | EVQVEESGGGLVQPGGSMRLSCVASGFSFNNYWMNWVRQSPGKGLEWVA EIRLKSNNYATHYVDSVKGRFTISRDDSKSSVYLQMNNLRAEDTGIYYCTG WDDYAMDHWGQGISVTVSS (SEQ ID NO: 27) |
| huCD20-7 v1.0 | ELQLVQSGGELKKPGETVRISCAASGYSFTNYGMNWVKQAPGKGLKWMG WINTYTGEPSYAAPFKGRFAFSLETSASTAYLQISSLKTEDTATYFCARGAY YRYDLGMDYWGQGTSVTVSS (SEQ ID NO: 28) |
| huCD20-7 v.1.1 | ELQLVQSGGELKKPGETVRISCAASGYTFTNYGMNWVKQAPGKGLKWMG WINTYTGEPSYAAPFKGRFAFSLETSASTAYLQISSLKTEDTATYFCARGAY YRYDLGMDYWGQGTSVTVSS (SEQ ID NO: 29) |

TABLE 8

Anti-CD20 Variable light chain amino acid sequences

| CD20 Antibody | VL Amino Acid Sequence (SEQ ID NO) |
|---|---|
| Veltuzumab | DIQLTQSPSSLSASVGDRVTMTCRASSSVSYIHWFQQKPGKAPKPWIYATSN LASGVPVRFSGSGSGTDYTFTISSLQPEDIATYYCQQWTSNPPTFGGGTKLEI K (SEQ ID NO: 30) |
| Rituximab | QIVLSQSPAILSASPGEKVTMTCRASSSVSYIHWFQQKPGSSPKPWIYATSNL ASGVPVRFSGSGSGTSYSLTISRVEAEDAATYYCQQWTSNPPTFGGGTKLEI K (SEQ ID NO: 31) |
| Ofatumumab | EIVLTQSPATLSLSPGERATLSCRASQSVSSYLAWYQQKPGQAPRLLIYDASN RATGIPARFSGSGSGTDFTLTISSLEPEDFAVYYCQQRSNWPITFGQGTRLEIK (SEQ ID NO: 32) |
| Obinutuzumab | DIVMTQTPLSLPVTPGEPASISCRSSKSLLHSNGITYLYWYLQKPGQSPQLLIY QMSNLVSGVPDRFSGSGSGTDFTLKISRVEAEDVGVYYCAQNLELPYTFGG GTKVEIK (SEQ ID NO: 33) |
| huCD20-4 | DIQMTQSPSTMSTSVGDRVSVNCKASQNVGTNVAWYQQKPGKSPKGLIYS ASFRYSGVPSRFTGSGSGTDFTLTIFNVQPDDLAEYFCQQYNNYPLTFGG GTKLEIKR (SEQ ID NO: 34) |

TABLE 8-continued

Anti-CD20 Variable light chain amino acid sequences

| CD20 Antibody | VL Amino Acid Sequence (SEQ ID NO) |
|---|---|
| huCD20-7 | DIVLTQSPASLAVSPGQRATISCRASGSVDSFGNSFMHWYQQKPGQPPKL LIYRASNLESGVPARFSGGGSRTDFTLTINPVEANDIATYFCQQSYEDPF TFGQGTKLELKR (SEQ ID NO: 35) |

Provided herein are anti-CD20 antibodies and antigen-binding fragments thereof that comprise: (a) a VH polypeptide having at least about 90% sequence identity to one of SEQ ID NOs:23-29; and/or (b) a VL polypeptide having at least about 90% sequence identity to one of SEQ ID NOs: 30-35. In certain embodiments, the antibody or antigen-binding fragment thereof comprises (a) a VH polypeptide having at least about 95%, at least about 96%, at least about 97%, at least about 98%, or at least about 99% sequence identity to one of SEQ ID NOs:23-29 and (b) a VL polypeptide having at least about 95%, at least about 96%, at least about 97%, at least about 98%, or at least about 99% sequence identity to one of SEQ ID NOs: 30-35. In certain embodiments, the antibody or antigen-binding fragment thereof comprises (a) a VH polypeptide having at least about 95% sequence identity to one of SEQ ID NOs:23-29, and (b) a VL polypeptide having at least about 95% sequence identity to one of SEQ ID NOs: 30-35. In certain embodiments, the antibody or antigen-binding fragment comprises (a) a VH polypeptide having the amino acid sequence of one of SEQ ID NOs:23-29; and (b) a VL polypeptide having the amino acid sequence of one of SEQ ID NOs: 30-35. In certain embodiments, the antibody or antigen-binding fragment specifically binds CD20. In certain embodiments, the antibody or antigen-binding fragment is a murine, chimeric, or humanized antibody that specifically binds CD20. In certain embodiments, the antibody or antigen-binding fragment is a human antibody that specifically binds CD20. In certain embodiments, the antibody or antigen-binding fragment containing polypeptides having a certain percentage of sequence identity to SEQ ID NOs:23-29 and 30-35 differs from SEQ ID NOs:23-29 and 30-35 by conservative amino acid substitutions only.

Anti-CD20 antibodies that can be used in combination with an anti-CD37 immunoconjugate (e.g., IMGN529) are provided, for example, in Boross et al., *Am J Cancer Res* 2: 676-690 (2012), Robak et al., *BioDrugs* 25:13-25 (2011), and Lim et al., *Haematologica* 95: 135-143 (2010), all of which are herein incorporated by reference in its entirety. In some embodiments, the anti-CD20 antibody used in combination with an anti-CD37 immunoconjugate is an anti-CD20 antibody described in WO2011/100398 or WO2011/100403, both of which are herein incorporated by reference in their entities. In some embodiments, the anti-CD20 antibody used in combination with an anti-CD37 immunoconjugate is selected from the group consisting of ocrelizumab, TRU-015, veltuzumab (IMMU-106), rituximab, ofatumumab, obinutuzumab (GA101; R05072759), ibritumomab tiuxetan, tositumomab, AME-133v (LY2469298), ocrelizumab, huCD20-4 (as described in WO2011/100398), huCD20-7 (as described in WO2011/100403), and Pro131921.

Anti-CD20 antibodies that can be used in combination with an anti-CD37 immunoconjugate (e.g., IMGN529) can be, e.g., type I antibodies or type II antibodies. (See e.g., Beers et al., *Blood* 112: 4170-4177 (2008) and Pers et al., *Ann. Rheum. Dis.* 70: A73 (2011).) In some embodiments, an anti-CD37 immunoconjugate (e.g., IMGN529) is used in combination with a type I anti-CD20 antibody. In some embodiments, an anti-CD37 immunoconjugate (e.g., IMGN529) is used in combination with a type I anti-CD20 antibody. In some embodiments, an anti-CD37 immunoconjugate (e.g., IMGN529) is used in combination with an anti-CD20 antibody that is not a type I antibody. Thus, in some embodiments, the anti-CD20 antibody is not rituximab. In some embodiments, the anti-CD20 antibody does not bind to the same epitope as rituximab. In some embodiments, the anti-CD20 antibody is not ofatumumab. In some embodiments, an anti-CD37 immunoconjugate (e.g., IMGN529) is used in combination with a type II anti-CD20 antibody.

In some embodiments, the anti-CD20 antibody used in combination with an anti-CD37 immunoconjugate (e.g., IMGN529) is selected from the group consisting of veltuzumab, rituximab, ofatumumab, and obinutuzumab. In some embodiments, the anti-CD20 antibody used in combination with an anti-CD37 immunoconjugate (e.g., IMGN529) is selected from the group consisting of rituximab, ofatumumab, and obinutuzumab.

In some embodiments, the anti-CD20 antibody used in combination with an anti-CD37 immunoconjugate (e.g., IMGN529) is veltuzumab. In some embodiments, the anti-CD20 antibody used in combination with an anti-CD37 immunoconjugate (e.g., IMGN529) is rituximab. In some embodiments, the anti-CD20 antibody used in combination with an anti-CD37 immunoconjugate (e.g., IMGN529) is ofatumumab. In some embodiments, the anti-CD20 antibody used in combination with an anti-CD37 immunoconjugate (e.g., IMGN529) is obinutuzumab.

IV. Methods of Use and Pharmaceutical Compositions

As provided herein, anti-CD37 immunoconjugates (e.g., IMGN529) and anti-CD20 antibodies can be used in combination to deplete cancerous cells. The cancerous cells can be B-cells (B-cell malignancies). In some embodiments, the B-cells express CD37. In some embodiments, the B-cells overexpress CD37.

As provided herein, anti-CD37 immunoconjugates (e.g., IMGN529) and anti-CD20 antibodies can be used in combination to treat cancer. The cancer can be a B-cell cancer. The cancer can be a leukemia or lymphoma. In some embodiments, the cancer expresses CD37. In some embodiments, the cancer overexpresses CD37.

In certain embodiments, the combination of the anti-CD37 immunoconjugate (e.g., IMGN529) and the anti-CD20 antibody is useful for inhibiting tumor growth. In certain embodiments, the combination of the anti-CD37 immunoconjugate (e.g., IMGN529) and the anti-CD20 antibody is useful for inducing differentiation of tumor cells. In certain embodiments, the combination of the anti-CD37 immunoconjugate (e.g., IMGN529) and the anti-CD20 antibody is useful for reducing tumor volume. In certain embodiments, the combination of the anti-CD37 immunoconjugate (e.g., IMGN529) and the anti-CD20 antibody is useful for reducing the tumorigenicity of a tumor. The methods of use can be in vivo methods.

In certain embodiments, the combination of the anti-CD37 immunoconjugate (e.g., IMGN529) and the anti-CD20 antibody produces greater efficacy than the sum of the efficacy of the anti-CD37 immunoconjugate (e.g., IMGN529) alone and the anti-CD20 antibody alone. In certain embodiments, the combination of the anti-CD37 immunoconjugate (e.g., IMGN529) and the anti-CD20 antibody produces the efficacy of the sum of the efficacy of the anti-CD37 immunoconjugate (e.g., IMGN529) alone and the anti-CD20 antibody alone using smaller and/or less frequent doses of the anti-CD37 immunoconjugate (e.g., IMGN529) and/or the anti-CD20 antibody. In certain embodiments, the combination of the anti-CD37 immunoconjugate (e.g., IMGN529) and the anti-CD20 antibody produces less toxicity than the sum of the toxicity of the anti-CD37 immunoconjugate (e.g., IMGN529) alone and the anti-CD20 antibody alone. In certain embodiments, the anti-CD37 immunoconjugate (e.g., IMGN529) potentiates the efficacy of the anti-CD20 antibody. In certain embodiments, the anti-CD20 antibody potentiates the efficacy of the anti-CD37 immunoconjugate (e.g., IMGN529).

In certain embodiments, the combination of the anti-CD37 immunoconjugate (e.g., IMGN529) and rituximab contains an amount of the anti-CD37 immunoconjugate (e.g., IMGN529) that is sufficient to potentiate the efficacy of the rituximab. In certain embodiments, the combination of the anti-CD37 immunoconjugate (e.g., IMGN529) and rituximab contains an amount of rituximab that is sufficient to potentiate the efficacy of the anti-CD37 immunoconjugate (e.g., IMGN529). In certain embodiments, the combination of the anti-CD37 immunoconjugate (e.g., IMGN529) and rituximab contains an amount of rituximab that is sufficient to reduce the amount of anti-CD37 immunoconjugate (e.g., IMGN529) needed for efficacy, and therefore reduce toxicity associated with the anti-CD37 immunoconjugate (e.g., IMGN529).

In certain embodiments, the combination of the anti-CD37 immunoconjugate (e.g., IMGN529) and the anti-CD20 antibody produces a synergistic effect. In some embodiments, a Synergy Score for the combination is calculated, for example based on the effect of the combination on cell viability. In some embodiments, the Synergy Score is at least 4. In some embodiments, the Synergy Score is at least 5. In some embodiments, the Synergy Score is at least 10. In some embodiments, the Synergy Score is at least 15. In some embodiments, the Synergy Score is at least 20. In some embodiments, the Synergy Score is at least 25. In some embodiments, the Synergy Score is at least 30. In some embodiments, the Synergy Score is at least 35. In some embodiments, the Synergy Score is at least 40. In some embodiments, the Synergy Score is at least 45. In some embodiments, the Synergy Score is at least 50. In some embodiments, the Synergy Score is at least 55. In some embodiments, the Synergy Score is at least 60. In some embodiments, the Synergy Score is from 4 to 100. In some embodiments, the Synergy Score is from 4 to 80. In some embodiments, the Synergy Score is from 4 to 65. In some embodiments, the Synergy Score is from 10 to 100. In some embodiments, the Synergy Score is from 10 to 80. In some embodiments, the Synergy Score is from 10 to 65. In some embodiments, the Synergy Score is from 20 to 100. In some embodiments, the Synergy Score is from 20 to 80. In some embodiments, the Synergy Score is from 20 to 65.

In certain embodiments, the combination of the anti-CD37 immunoconjugate (e.g., IMGN529) and the anti-CD20 antibody produces a combination index of less than 1. In some embodiments, the combination index is less than 0.4. In some embodiments, the combination index is less than 0.3. In some embodiments, the combination index is less than 0.2. In some embodiments, the combination index is from 0.2 to 0.4. In some embodiments, the combination index is from 0.2 to 0.3.

In certain embodiments, administration of the anti-CD37 immunoconjugate (e.g., IMGN529) and the anti-CD20 antibody does not produce more toxicity than administration of the antibody that binds to CD20. In some embodiments, administration of the anti-CD37 immunoconjugate (e.g., IMGN529) and the anti-CD20 antibody does not produce more toxicity than administration of the anti-CD37 immunoconjugate (e.g., IMGN529). In some embodiments, the anti-CD37 immunoconjugate (e.g., IMGN529) and the anti-CD20 antibody does not produce more toxicity than administration of either the anti-CD37 immunoconjugate (e.g., IMGN529) or the anti-CD20 antibody.

In certain embodiments, administration of the anti-CD37 immunoconjugate (e.g., IMGN529) and the anti-CD20 antibody does not produce more toxicity than administration of R-CHOP (rituximab, cyclophosphamide, doxorubicin, vincristine, and prednisone). In certain embodiments, administration of the anti-CD37 immunoconjugate (e.g., IMGN529) and the anti-CD20 antibody results in less toxicity than administration of R-CHOP.

In certain embodiments, the dosage of the anti-CD37 immunoconjugate (e.g., IMGN529) is from about 0.1 to 3.0 mg of the CD37-binding agent per kg of body weight (mg/kg). In certain embodiments, the dosage of the immunoconjugate (e.g., IMGN529) is from 0.4 to 0.8 mg per kg of body weight. In certain embodiments, the dosage of the immunoconjugate (e.g., IMGN529) is from 0.7 to 1.8 mg per kg of body weight. In certain embodiments, the dosage of the immunoconjugate (e.g., IMGN529) is from 0.8 to 1.4 mg per kg of body weight. In certain embodiments, the dosage of the immunoconjugate (e.g., IMGN529) is from 0.8 to 1.2 mg per kg of body weight. In certain embodiments, the dosage of the immunoconjugate (e.g., IMGN529) is from 1.0 to 3.0 mg per kg of body weight. In certain embodiments, the dosage of the immunoconjugate (e.g., IMGN529) is from 1.0 to 2.8 mg per kg of body weight. In certain embodiments, the dosage of the immunoconjugate (e.g., IMGN529) is from about 1.0 to about 1.4 mg per kg of body weight. In certain embodiments, the dosage of the immunoconjugate (e.g., IMGN529) is from about 1.4 to about 2.0 mg per kg of body weight. In certain embodiments, the dosage of immunoconjugate (e.g., IMGN529) is from about 1.4 to about 3.0 mg per kg of body weight. In certain embodiments, the dosage of the immunoconjugate (e.g., IMGN529) is from about 1.4 to about 2.8 mg per kg of body weight. In certain embodiments, the dosage of the immunoconjugate (e.g., IMGN529) is from about 2.0 to about 2.8 mg per kg of body weight. In certain embodiments, the dosage of the immunoconjugate (e.g., IMGN529) is from about 2.0 to about 3.0 mg per kg of body weight. In certain embodiments, the dosage of immunoconjugate (e.g., IMGN529) is about 0.1 mg per kg of body weight. In certain embodiments, the immunoconjugate (e.g., IMGN529) is about 0.2 mg per kg of body weight. In certain embodiments, the dosage of the immunoconjugate (e.g., IMGN529) is about 0.3 mg per kg of body weight. In certain embodiments, the dosage of immunoconjugate (e.g., IMGN529) is about 0.4 mg per kg of body weight. In certain embodiments, the dosage of the immunoconjugate (e.g., IMGN529) is about 0.5 mg per kg of body weight. In certain embodiments, the dosage of the immunoconjugate (e.g., IMGN529) is about 0.6 mg per kg of body weight. In certain embodiments, the dosage of the immunoconjugate (e.g., IMGN529) is about 0.7 mg per kg of body weight. In certain embodiments, the dosage of the immunoconjugate (e.g., IMGN529) is about 0.8 mg per kg of body weight. In certain embodiments, the dosage of the immunoconjugate (e.g., IMGN529) is about 0.9 mg per kg of body weight. In certain embodiments, the dosage of the immunoconjugate (e.g., IMGN529) is about 1.0 mg per kg of body weight. In certain embodiments, the dosage of the immunoconjugate (e.g., IMGN529) is about 1.1 mg per kg of body weight. In certain embodiments, the dosage of the immunoconjugate (e.g., IMGN529) is about 1.2 mg per kg of body weight. In certain embodiments, the dosage of the immunoconjugate (e.g., IMGN529) is about 1.3 mg per kg of body weight. In certain embodiments, the dosage of the immunoconjugate (e.g., IMGN529) is about 1.4 mg per kg of body weight. In certain embodiments, the dosage of the immunoconjugate (e.g., IMGN529) is about 1.5 mg per kg of body weight. In certain embodiments, the dosage of the immunoconjugate (e.g., IMGN529) is about 1.6 mg per kg of body weight. In certain embodiments, the dosage of the immunoconjugate (e.g., IMGN529) is about 1.7 mg per kg of body weight. In certain embodiments, the dosage of the immunoconjugate (e.g., IMGN529) is about 1.8 mg per kg of body weight. In certain embodiments, the dosage of the immunoconjugate (e.g., IMGN529) is about 1.9 mg per kg of body weight. In certain embodiments, the dosage of the immunoconjugate (e.g., IMGN529) is about 2.0 mg per kg of body weight. In certain embodiments, the dosage of immunoconjugate (e.g., IMGN529) is about 2.1 mg per kg of body weight. In certain embodiments, the dosage of the immunoconjugate (e.g., IMGN529) is about 2.2 mg per kg of body weight. In certain embodiments, the dosage of the immunoconjugate (e.g., IMGN529) is about 2.3 mg per kg of body weight. In certain embodiments, the dosage of the immunoconjugate (e.g., IMGN529) is about 2.4 mg per kg of body weight. In certain embodiments, the dosage of the immunoconjugate (e.g., IMGN529) is about 2.5 mg per kg of body weight. In certain embodiments, the dosage of the immunoconjugate (e.g., IMGN529) is about 2.6 mg per kg of body weight. In certain embodiments, the dosage of the immunoconjugate (e.g., IMGN529) is about 2.7 mg per kg of body weight. In certain embodiments, the dosage of the immunoconjugate (e.g., IMGN529) is about 2.8 mg per kg of body weight. In certain embodiments, the dosage of the immunoconjugate (e.g., IMGN529) is about 2.9 mg per kg of body weight. In certain embodiments, the dosage of the immunoconjugate (e.g., IMGN529) is about 3.0 mg per kg of body weight. In certain embodiments, the dosage of the immunoconjugate (e.g., IMGN529) is sufficient to saturate binding to CD37. In certain embodiments, the dosage of the immunoconjugate (e.g., IMGN529) is sufficient to super saturate binding to CD37.

In certain embodiments, the dosage of the anti-CD20 antibody is about 375 mg/m$^2$ (e.g., for the treatment of NHL). In certain embodiments, the dosage of the anti-CD20 antibody is about 375 mg/m$^2$ in a first cycle and about 500 mg/m$^2$ in cycles 2-6 (every 28 days) (e.g., for the treatment of CLL). In certain embodiments, the dosage of rituximab is about 375 mg/m$^2$ (e.g., for the treatment of NHL). In certain embodiments, the dosage of rituximab is about 375 mg/m$^2$ in a first cycle and about 500 mg/m$^2$ in cycles 2-6 (every 28 days) (e.g., for the treatment of CLL).

In certain embodiments, the dosage of the anti-CD20 antibody is about 100 mg on day 1 of Cycle 1, about 900 mg on day 2 of Cycle 1, about 1000 mg on day 8 and 15 of Cycle 1, and about 1000 mg on day 1 of Cycles 2-6 (28-day cycle). In certain embodiments, the dosage of obinutuzumab is about 100 mg on day 1 or Cycle 1, about 900 mg on day 2 of Cycle 1, about 1000 mg on day 8 and 15 of Cycle 1, and about 1000 mg on day 1 of Cycles 2-6 (28-day cycle).

In certain embodiments, the dosage of the anti-CD20 antibody is about 300 mg. In certain embodiments, the dosage of the anti-CD20 antibody is about 300 mg on day 1 followed by 1,000 mg on day 8 of cycle 1, about 1,000 mg on day 1 of subsequent 28-day cycles for a minimum of 3 cycles until best response or a maximum of 12 cycles (e.g., for the treatment of previously untreated CLL). In certain embodiments, the dosage of the anti-CD20 antibody is about 300 mg initial dose, followed 1 week later by 2,000 mg weekly for 7 doses, followed 4 weeks later by 2,000 mg every 4 weeks for 4 doses (e.g., for refractory CLL). In certain embodiments, the dosage of ofatumumab is about 300 mg. In certain embodiments, the dosage of ofatumumab is about 300 mg on day 1 followed by 1,000 mg on day 8 of cycle 1, about 1,000 mg on day 1 of subsequent 28-day cycles for a minimum of 3 cycles until best response or a maximum of 12 cycles (e.g., for the treatment of previously untreated CLL). In certain embodiments, the dosage of ofatumumab is about 300 mg initial dose, followed 1 week later by 2,000 mg weekly for 7 doses, followed 4 weeks later by 2,000 mg every 4 weeks for 4 doses (e.g., for refractory CLL).

In certain embodiments, the anti-CD37 immunoconjugate (e.g., IMGN529) is administered once every three weeks.

In certain embodiments, the anti-CD20 antibody is administered once every week. In certain embodiments, the anti-CD20 antibody is administered on week 1, day 1 of a three week schedule. In certain embodiments, the anti-CD20 antibody is administered once every week for four to eight doses. In certain embodiments, the anti-CD20 antibody is administered once every week for four doses. In certain embodiments, the anti-CD20 antibody is administered in a cycle with chemotherapy, e.g., on day 1 of each cycle of chemotherapy for up to eight doses. In certain embodiments, the anti-CD20 antibody is administered after chemotherapy, e.g., once weekly for four doses at six month intervals up to a maximum of sixteen doses. In certain embodiments, rituximab is administered once every week. In certain embodiments, rituximab is administered on week 1, day 1 of a three week schedule. In certain embodiments, rituximab is administered once every week for four to eight doses. In certain embodiments, rituximab is administered once every week for four doses. In certain embodiments, rituximab is administered in a cycle with chemotherapy, e.g., on day 1 of each cycle of chemotherapy for up to eight doses. In certain embodiments, rituximab is administered after chemotherapy, e.g., once weekly for four doses at six month intervals up to a maximum of sixteen doses.

In certain embodiments, the anti-CD20 antibody is administered on a 28-day cycle. In certain embodiments, the anti-CD20 antibody is administered on a 28-day cycle on days 1, 2, 8, and 15 of a first cycle, and on day 1 of cycles 2-6. In certain embodiments, obinutuzumab is administered on a 28-day cycle. In certain embodiments, obinutuzumab is administered on a 28-day cycle on days 1, 2, 8, and 15 of a first cycle, and on day 1 of cycles 2-6.

In certain embodiments, the anti-CD20 antibody is administered on a 28-day cycle. In certain embodiments, the anti-CD20 antibody is administered on days 1 and 8 of cycle 1, and on day 1 of subsequent 28-day cycles for a minimum of 3 cycles or a maximum of 12 cycles. In certain embodiments, the anti-CD20 antibody is administered once every week. In certain embodiments, ofatumumab is administered on a 28-day cycle. In certain embodiments, ofatumumab is administered on days 1 and 8 of cycle 1, and on day 1 of subsequent 28-day cycles for a minimum of 3 cycles or a maximum of 12 cycles. In certain embodiments, ofatumumab is administered once every week.

The present invention provides for methods of treating cancer comprising administering a therapeutically effective amount of a CD37-binding agent to a subject (e.g., a subject in need of treatment). In certain embodiments, the cancer is a B-cell malignancy. In certain embodiments, the cancer is leukemia or lymphoma. In certain embodiments, the cancer is selected from the group consisting of B cell lymphomas, NHL, precursor B cell lymphoblastic leukemia/lymphoma and mature B cell neoplasms, B cell chronic lymphocytic leukemia (CLL)/small lymphocytic lymphoma (SLL), small cell lymphoma, B cell prolymphocytic leukemia, lymphoplasmacytic lymphoma, mantle cell lymphoma (MCL), follicular lymphoma (FL), low grade, intermediate-grade and high-grade (FL), cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, acute lymphoblastic leukemia (ALL), and anaplastic large-cell lymphoma (ALCL). In certain embodiments, the cancer is selected from the group consisting of diffuse large B cell lymphoma (DLBCL), follicular lymphoma (FL), unspecified NHL, MALT lymphoma, mantle cell lymphoma (MCL), Burkitt's lymphoma (BL), and chronic lymphocytic leukemia (CLL). In certain embodiments, the cancer is NHL. In certain embodiments, the cancer is relapsed or refractory NHL. In certain embodiments, the cancer is CLL. In certain embodiments, the cancer is refractory CLL. In certain embodiments, the cancer is previously untreated CLL. In certain embodiments, the subject is a human.

In certain embodiments, the cancer overexpresses the transcription factor MYC. In certain embodiments, the cancer that overexpress MYC is a DLBCL. In certain embodiments, the cancer overexpresses the anti-apoptotic protein BCL2. In certain embodiments, the cancer that overexpress BCL2 is a DLBCL. In certain embodiments, the cancer overexpresses MYC and BCL2. In certain embodiments, the cancer that overexpress MYC and BCL2 is a DLBCL. In certain embodiments, the cancer that overexpress MYC and BCL2 is a GCB DLBCL. In certain embodiments, the cancer that overexpress MYC and BCL2 is an ABC DLBCL. MYC and/or BCL-2 overexpression is associated with poor prognosis. Overexpression can be detected by any method used to detect protein levels, including but not limited to, immunohistochemistry (IHC). In some embodiments, MYC and/or BCL-2 overexpression is due to genomic alterations that lead to protein overexpression. In such cases, detection of the genomic alteration, for example, by FISH, can be used. Overexpression of MYC and/or BCL-2 can be determined by those of skill in the art. (See, for example, Green et al., *J. Clin. Oncol.* 30: 3460-3467 (2012); Hu et al., *Blood* 121: 4021-4031 (2013); and Friedberg, *J. Clin. Oncol.* 30:3439-3443 (2012)).

In addition, the invention provides a method of reducing the tumorigenicity of a tumor in a subject, comprising administering a therapeutically effective amount of an anti-CD37 immunoconjugate (e.g., IMGN529) and an anti-CD20 antibody to the subject. In certain embodiments, the tumor comprises cancer stem cells. In certain embodiments, the frequency of cancer stem cells in the tumor is reduced by administration of the agents.

The present invention further provides pharmaceutical compositions comprising one or more of the anti-CD37 immunoconjugates (e.g., IMGN529) described herein to be used in combination with an anti-CD20 antibody. The present invention further provides pharmaceutical compositions comprising one or more of the anti-CD20 antibodies described herein to be used in combination with an anti-CD37 antibody. The present invention further provides pharmaceutical compositions comprising an anti-CD37 immunoconjugate (e.g., IMGN529) and an anti-CD20 antibody. In certain embodiments, the pharmaceutical compositions further comprise a pharmaceutically acceptable vehicle. In certain embodiments, the pharmaceutical compositions further comprise a preservative. These pharmaceutical compositions find use in inhibiting tumor growth and treating cancer in human patients.

The pharmaceutical compositions for use as provided herein can be administered in any number of ways for either local or systemic treatment. Administration can be topical such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration. In some embodiments, the administration is intravenous.

In some embodiments, the anti-CD37 immunoconjugate (e.g., IMGN529) and anti-CD20 antibody can be combined in a pharmaceutical combination formulation, or dosing regimen as combination therapy, with a third, fourth, or additional compounds.

In some embodiments, the methods further comprise administering a corticosteroid to the patient. In some embodiments the corticosteroid can be selected from the group consisting of prednisone, prednisolone, methylprednisolone, beclamethasone, betamethasone, dexamethasone, fludrocortisone, hydrocortisone, and triamcinolone. In some embodiments, the corticosteroid can be dexamethasone. In some embodiments, the corticosteroid can be administered as a pre-treatment, i.e., prior to the administration of the anti-CD37 immunoconjugate (e.g., IMGN529). In some embodiments, the corticosteroid can be administered during the administration of the anti-CD37 immunoconjugate (e.g., IMGN529). In some embodiments, the corticosteroid can be administered during the administration of the anti-CD37 immunoconjugate (e.g., IMGN529) and at least one additional time from about one day after to about five days after the administration of the anti-CD37 immunoconjugate (e.g., IMGN529). In some embodiments, the corticosteroid can be administered during the administration of the anti-CD37 immunoconjugate (e.g., IMGN529) and at least one additional time from about one day after to about four days after the administration of the anti-CD37 immunoconjugate (e.g., IMGN529). In some embodiments, the corticosteroid can be administered during the administration of the anti-CD37 immunoconjugate (e.g., IMGN529) and at least one additional time from about one day after to about three days after the administration of the anti-CD37 immunoconjugate (e.g., IMGN529). In some embodiments, the corticosteroid can be administered during the administration of the anti-CD37 immunoconjugate (e.g., IMGN529) and at least one additional time from about one day after to about two days after the administration of the anti-CD37 immunoconjugate (e.g., IMGN529). In some embodiments, the corticosteroid can be administered during the administration of the anti-CD37 immunoconjugate (e.g., IMGN529) and at least one additional time from about two days after to about five days after the administration of the anti-CD37 immunoconjugate (e.g., IMGN529). In some embodiments, the corticosteroid can be administered during the administration of the anti-CD37 immunoconjugate (e.g., IMGN529) and at least one additional time from about two days after to about four days after the administration of the anti-CD37 immunoconjugate (e.g., IMGN529). In some embodiments, the corticosteroid can be administered during the administration of the anti-CD37 immunoconjugate (e.g., IMGN529) and at least one additional time from about two days after to about three days after the administration of the anti-CD37 immunoconjugate (e.g., IMGN529). In some embodiments, the corticosteroid can be administered during the administration of the anti-CD37 immunoconjugate (e.g., IMGN529) and at about two days after and at about three days after the administration of the anti-CD37 immunoconjugate (e.g., IMGN529). In some embodiments, the corticosteroid can be administered during the administration of the anti-CD37 immunoconjugate (e.g., IMGN529) and at about two days after and at about three days after the administration of the anti-CD37 immunoconjugate (e.g., IMGN529). In some embodiments, the corticosteroid can be administered by pen-infusion. In some embodiments, the corticosteroid is administered 30 to 60 minutes prior to administration of the anti-CD37 immunoconjugate (e.g., IMGN529). In some embodiments, the corticosteroid is administered 30 to 60 minutes prior to administration of the anti-CD37 immunoconjugate (e.g., IMGN529) and on at least one additional time on days 1 to 3 following administration of the anti-CD37 immunoconjugate (e.g., IMGN529). Pre-infusion intravenous steroid administration was found to eliminate cytokine-mediated adverse effects. In some embodiments, the corticosteroid is administered on at least one of days 2 and 3 following infusion. In some embodiments, the corticosteroid is administered by IV 30 to 60 minutes prior to administration of the anti-CD37 immunoconjugate (e.g., IMGN529) and orally on days 2 and 3 following infusion.

In some embodiments the corticosteroid is administered by IV. In some embodiments the steroid is administered orally.

In some embodiments, the corticosteroid is administered intravenously 30 to 60 minutes prior to the administration of the anti-CD37 immunoconjugate (e.g., IMGN529) and the corticosteroid is administered orally on days 2 and 3 of a 3-week anti-CD37 immunoconjugate (e.g., IMGN529) administration cycle.

In some embodiments the corticosteroid to be administered can be dexamethasone. In some embodiments the corticosteroid to be administered can be methylprednisolone. In some embodiments the corticosteroid to be administered can be prednisolone.

In some embodiments, from about 5 mg to about 10 mg dexamethasone is administered. In some embodiments, from about 8 mg to about 10 mg dexamethasone is administered. In some embodiments, about 10 mg dexamethasone is administered. In some embodiments, about 8 mg dexamethasone is administered. In some embodiments about 10 mg dexamethasone is administered by IV 30 to 60 minutes prior to administration of the anti-CD37 immunoconjugate (e.g., IMGN529). In some embodiments about 10 mg dexamethasone is administered by IV at the time of administration of the anti-CD37 immunoconjugate (e.g., IMGN529) and again about 1 to about 5 days after administration of the anti-CD37 immunoconjugate (e.g., IMGN529). In some embodiments, the corticosteroid is administered by IV 30 to 60 minutes prior to administration of the anti-CD37 immunoconjugate (e.g., IMGN529) and one dose of 8 mg of dexamethasone is delivered orally on days 2 and 3 following infusion.

In some embodiments, 10 mg dexamethasone is administered intravenously 30 to 60 minutes prior to the administration of the anti-CD37 immunoconjugate (e.g., IMGN529) and 8 mg dexamethasone is administered orally on days 2 and 3 of a 3-week anti-CD37 immunoconjugate (e.g., IMGN529) administration cycle.

In some embodiments, the methods further comprise administering a growth factor to the patient. Methods of administering white blood cell growth factors are reviewed, for example, in Smith et al., *J. Clin. Oncol.* 24: 3187-3205 (2006), which is herein incorporated by reference in its entirety. Growth factor treatment may decrease the likelihood of neutropenias. In some embodiments, the growth factor can be granulocyte colony-stimulating factor (G-CSF). In some embodiments the growth factor can be granulocyte-macrophage colony-stimulating factor (GM-CSF). In some embodiments the growth factor can be macrophage colony-stimulating factor (M-CSF). In some embodiments, the growth factor can be filgrastim. In some embodiments, the growth factor can be pegylated, e.g., pegylated G-CSF. In some embodiments, the growth factor can be pegfilgrastim, marketed as Neulasta®.

In some embodiments, the growth factor can be administered as a pre-treatment, i.e., prior to the administration of the anti-CD37 immunoconjugate (e.g., IMGN529). In some embodiments, the anti-CD37 immunoconjugate (e.g., IMGN529) is administered on a 3-week (about 21-day) cycle and the growth factor can be administered at any point during the 3-week (about 21-day) cycle. In some embodiments, the anti-CD37 immunoconjugate (e.g., IMGN529) is administered on a 3-week (about 21-day) cycle and the growth factor can be administered early to middle cycle of the 3-week (about 21-day) cycle. In some embodiments, the growth factor can be administered on at least one day from day 1 to about day 21 of the 3-week (about 21-day) cycle. In some embodiments, the growth factor can be administered on at least one day from day 1 to about day 20 of the 3-week (about 21-day) cycle. In some embodiments, the growth factor can be administered on at least one day from day 1 to about day 19 of the 3-week (about 21-day) cycle. In some embodiments, the growth factor can be administered on at least one day from day 1 to about day 18 of the 3-week (about 21-day) cycle. In some embodiments, the growth factor can be administered on at least one day from day 1 to about day 17 of the 3-week (about 21-day) cycle. In some embodiments, the growth factor can be administered on at least one day from day 1 to about day 16 of the 3-week (about 21-day) cycle. In some embodiments, the growth factor can be administered on at least one day from day 1 to about day 14 of the 3-week (about 21-day) cycle. In some embodiments, the growth factor can be administered on at least one day from day 1 to about day 12 of the 3-week (about 21-day) cycle. In some embodiments, the growth factor can be administered on at least one day from day 1 to about day 8 of the 3-week (about 21-day) cycle. In some embodiments, the growth factor can be administered on at least one day from day about 15 to about day 21 of the 3-week (about 21-day) cycle. In some embodiments, the growth factor can be administered on at least one day from about day 3 to about day 10 of the 3-week (about 21-day) cycle. In some embodiments, the growth factor can be administered at least twice from about day 3 to about day 10 of the 3-week (about 21-day) cycle. In some embodiments, the growth factor can be administered at least three times from about day 3 to about day 10 of the 3-week (about 21-day) cycle. In some embodiments, the growth factor can be administered on at least one day from about day 4 to about day 10 of the 3-week (about 21-day) cycle. In some embodiments, the growth factor can be administered on at least one day from day 5 to day 8 of the 3-week (about 21-day) cycle. In some embodiments, the growth factor can be administered on at least one day selected from day 5, day 6, and day 8 of the 3-week (about 21-day) cycle. In some embodiments, the growth factor can be administered on days 5, 6, and 8 of the 3-week (about 21-day) cycle.

In some embodiments, G-CSF is administered at a dose of about 1 µg/kg body weight to about 15 µg/kg body weight, per day that the growth factor is administered. In some embodiments, G-CSF is administered at a dose of about 5 µg/kg/day. In some embodiments, G-CSF is administered at a dose of about 10 µg/kg/day.

In some embodiments, G-CSF is administered at a dose of about 200 µg to about 600 µg per day. In some embodiments, G-CSF is administered at a dose of about 300 µg to about 500 µg per day. In some embodiments, G-CSF is administered at a dose of about 300 µg to about 480 µg per day. In some embodiments, G-CSF is administered at a dose of about 300 µg/day. In some embodiments, G-CSF is administered at a dose of about 400 µg/day. In some embodiments, G-CSF is administered at a dose of about 480 µg/day. In some embodiments, G-CSF is administered at a dose of about 500 µg/day.

In some embodiments, GM-CSF is administered at a dose of about 100 µg/m$^2$ to about 500 µg/m$^2$, per day that the growth factor is administered. In some embodiments, GM-CSF is administered at a dose of about 250 µg/m$^2$/day.

In some embodiments, GM-CSF is administered at a dose of about 200 µg to about 600 µg per day. In some embodiments, GM-CSF is administered at a dose of about 300 µg to about 500 µg per day. In some embodiments, GM-CSF is administered at a dose of about 300 µg to about 480 µg per day. In some embodiments, GM-CSF is administered at a dose of about 300 µg/day. In some embodiments, G-CSF is administered at a dose of about 400 µg/day. In some embodiments, GM-CSF is administered at a dose of about 480 µg/day. In some embodiments, GM-CSF is administered at a dose of about 500 µg/day.

In some embodiments, pegfilgrastim is administered at a dose of about 6 mg per cycle. In some embodiments, pegfilgrastim is administered at a dose of about 10 µg/kg to about 500 µg/kg per cycle. In some embodiments, pegfilgrastim is administered at a dose of about 10 µg/kg to about 400 µg/kg per cycle. In some embodiments, pegfilgrastim is administered at a dose of about 50 µg/kg to about 300 µg/kg per cycle. In some embodiments, pegfilgrastim is administered at a dose of about 50 µg/kg to about 200 µg/kg per cycle. In some embodiments, pegfilgrastim is administered at a dose of about 50 µg/kg to about 150 µg/kg per cycle. In some embodiments, pegfilgrastim is administered at a dose of about 100 µg/kg per cycle.

In some embodiments, administration of corticosteroids and/or G-CSF to the dosing protocol allows a higher dose to be administered. In some embodiments, patients stay on the treatment longer due to the administration of corticosteroids and/or G-CSF. In some embodiments, less neutropenia is observed due to the administration of corticosteroids and/or G-CSF. In some embodiments, more clinical benefits are observed due to the administration of corticosteroids and/or G-CSF.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application

Example 1

IMGN529 Acts Synergistically with Anti-CD20 Antibodies Across a Panel of NHL Cell Lines IMGN529 is a CD37-targeting antibody-drug conjugate (ADC) comprising a CD37-binding antibody conjugated to the maytansinoid anti-mitotic, DM1. IMGN529 is huCD37-3-SMCC-DM1, and the huCD37-3 antibody contains a variable heavy chain with the amino acid sequence of SEQ ID NO:12 and a variable light chain with the amino acid sequence of SEQ ID NO:15.

IMGN529 was combined with 104 compounds (referred to as enhancer compounds) across a panel of 20 Non-Hodgkin's lymphoma (NHL) cell lines using an 8×6 or 8×8 combination dose response matrix over a treatment time of 72 hours. Five NHL subtypes were represented in this study: Germinal center B-cell diffuse large B-cell lymphoma (GCB DLBCL), activated B-cell diffuse large B cell lymphoma (ABC DLBCL), mantle cell lymphoma (MCL), chronic lymphocytic leukemia (CLL) and Burkitt lymphoma. See Table 9 for cell lines representative of each NHL subtype.

TABLE 9

| Non-Hodgkin's Lymphoma Cell Lines | |
|---|---|
| NHL Subtype | Representative Cell Line |
| GCB DLBCL | DOHH-2[1] |
|  | OCI-Ly1 |
|  | OCI-Ly7 |
|  | RL |
|  | SU-DHL-10-epst |
|  | SU-DHL-6-epst |
|  | WSU-NHL |
|  | OCI-Ly18 |
|  | SUDHL4 |
|  | SU-DHL-5 |
|  | Farage |
| ABC DLBCL | HBL-1 |
|  | SU-DHL-2-epst |
|  | U-2932 |
|  | OCI-Ly10 |
|  | TMD8 |

TABLE 9-continued

Non-Hodgkin's Lymphoma Cell Lines

| NHL Subtype | Representative Cell Line |
|---|---|
| MCL | GRANTA-519 |
| | MAVER-1 |
| | Jeko-1 |
| CLL | JVM-13 |
| | JVM-2 |
| Burkitt | Ramos (RA #1) |
| | Namalwa |

[1]DOHH2 is generally described in the literature as a follicular lymphoma model, but genetic characterization to determine the cell of origin showed DOHH2 to be DLBCL.

An anti-proliferation assay was performed to assess the effect of each compound and the combination of IMGN529 with each compound on cell viability. Cells were seeded in the appropriate growth media in 384- or 1536-well tissue culture treated plates at cell densities ranging from 200 to 1500, based on the doubling time of each cell line. Cells were equilibrated in assay plates via centrifugation and placed in incubators attached to the Dosing Modules at 37° C. for 24 hours before treatment. IMGN529 and the enhancer compound were added simultaneously to the cell lines. At the time of treatment, a set of assay plates (which did not receive treatment) was collected and ATP levels were measured by adding ATPLite (Perkin Elmer). These Tzero ($T_0$) plates were read using ultra-sensitive luminescence on Envision Plate Readers. Treated assay plates were incubated with compound for 72 hours. After 72 hours, plates were developed for endpoint analysis using ATPLite. All data points were collected via automated processes, quality controlled, and analyzed using Horizon CombinatoRx proprietary software. Assay plates were accepted if they passed the following quality control standards: relative luciferase values were consistent throughout the entire experiment, Z-factor scores were greater than 0.6, and untreated/vehicle controls behaved consistently on the plate. The calculation for Synergy Score is described below.

Horizon CombinatoRx utilizes Growth Inhibition (GI) as a measure of cell viability. The cell viability of vehicle is measured at the time of dosing ($T_0$) and after 72 hours ($T_{72}$). Horizon CombinatoRx calculates GI by applying the following test and equation $$\text{If } < V_0 : 100 * \left(1 - \frac{T - V_0}{V_0}\right)$$

$$\text{If } \geq V_0 : 100 * \left(1 - \frac{T - V_0}{V - V_0}\right)$$

where T is the signal measure for a test article, V is the vehicle-treated control measure, and $V_0$ is the vehicle control measure at time zero. This formula is derived from the Growth Inhibition calculation used in the National Cancer Institute's NCI-60 high throughput screen. All combination data analyses were performed using this measure of growth inhibition.

A GI reading of 0% represents no growth inhibition, i.e., cells treated with compound and $T_{72}$ vehicle signals are matched. A GI 100% represents complete growth inhibition, i.e., cells treated by compound and $T_0$ vehicle signals are matched. A GI of 100% indicates that cell numbers have not increased during the treatment period in wells and may suggest a cytostatic effect for compounds reaching a plateau at this effect level. A GI 200% represents complete death of all cells in the culture well. Compounds reaching an activity plateau of GI 200% are considered cytotoxic.

Both cytostatic and cytotoxic treatments can yield an Inhibition Percentage of 100%. Inhibition Percentage is calculated as the following:

$$I = 1 - T/U$$

where T is the treated and U is the Untreated.

To measure combination effects in excess of Loewe additivity, Horizon CombinatoRx's Synergy Score calculation, which is a scalar measure to characterize the strength of synergistic interaction, was used. The Synergy score was calculated as:

$$\text{Synergy Score} = \log f_X \; \log f_Y \Sigma \; \max(O, I_{data}) (I_{data} - I_{Loewe})$$

The fractional inhibition for each component agent and combination point in the matrix was calculated relative to the median of all vehicle-treated control wells. The Synergy Score equation integrates the experimentally-observed activity volume at each point in the matrix in excess of a model surface numerically derived from the activity of the component agents using the Loewe model for additivity. Additional terms in the Synergy Score equation (above) were used to normalize for various dilution factors used for individual agents and to allow for comparison of synergy scores across an entire experiment. The inclusion of positive inhibition gating or an $I_{data}$ multiplier removes noise near the zero effect level, and biases results for synergistic interactions at that occur at high activity levels. Combinations with higher maximum GI effects or those which are synergistic at low concentrations will have higher Synergy Scores. Those combinations with Synergy Scores that statistically supersede baseline self-cross values can be considered synergistic. Self-cross values were generated using 25 compounds that were combined with each other in each cell line Potency shifting was evaluated using an isobologram, which demonstrates the reduction in drug when used in combination to achieve a desired effect level, when compared to the single agent doses needed to reach that effect. The isobologram was drawn by identifying the locus of concentrations that correspond to crossing the indicated inhibition level. This was done by finding the crossing point for each single agent concentration in a dose matrix across the concentrations of the other single agent. Practically, each vertical concentration $C_Y$ is held fixed while a bisection algorithm is used to identify the horizontal concentration $C_X$ in combination with that vertical dose that gives the chosen effect level in the response surface $Z(C_X, C_Y)$. These concentrations are then connected by linear interpolation to generate the isobologram display. For synergistic interactions, the isobologram contour fall below the additivity threshold and approaches the origin, and an antagonistic interaction would lie above the additivity threshold. The error bars represent the uncertainty arising from the individual data points used to generate the isobologram. The uncertainty for each crossing point is estimated from the response errors using bisection to find the concentrations where $Z - \sigma_Z(C_X, C_Y)$ and $Z + \sigma_Z(C_X, C_Y)$ cross $I_{cut}$, where $\sigma_Z$ is the standard deviation of the residual error on the effect scale.

A survey of all synergy scores generated with IMGN529 with the 104 enhancer compounds shows that the highest synergy scores were obtained with the anti-CD20 antibodies. The mean synergy score for three anti-CD20 antibodies rituximab, obinutuzumab, and ofatumumab was almost three-fold higher than the mean synergy score obtained for the other enhancer compounds. Synergy was seen across multiple classes of enhancer compounds including other standard-of-care treatments used in NHL but not with all standard-of-care agents. For example, topoisomerase II inhibitors such as Doxorubicin and Etoposide did not show synergy when combined with IMGN529

The synergy scores obtained for the combinations between IMGN529 plus rituximab, IMGN529 plus obinutuzumab, and IMGN529 plus ofatumumab are shown in Table 10. The synergy scores in the underlined boxes represent those that supersede the mean self-cross plus two times the standard deviation ($2\sigma$). Statistically significant synergy scores range from 4.07 to 62.9. All three anti-CD20 antibodies showed significant synergy across 11 cell lines representing all sub-types of NHL. The anti-proliferation assay was repeated for the combinations between IMGN529 plus rituximab, IMGN529 plus obinutuzumab, and IMGN529 plus ofatumumab in a subset of the NHL cell lines. The synergistic effect of IMGN529 plus rituximab on reducing cell viability was recapitulated and the synergy scores were confirmed to be statistically significant. Significant synergy was also observed for ofatumumab and rituximab in three additional cell lines.

ergistic interactions (the isobologram contours fall below the additivity threshold), and the best CI values for each combination are below 0.4.

The combination of IMGN529 and rituximab was also studied in the OCI-Ly18 cell line model that represents a DLBCL patient population that is difficult to treat based on its molecular characteristics. This cell line overexpresses the transcription factor MYC and the anti-apoptotic protein BCL2, and this finding was confirmed internally using IHC (an H-score of 275 for BCL2 and an H score of 230 for MYC). H-scores combine staining intensity scores (e.g., a score of 0 to 3, wherein 0 represents no staining, and 3 represents strong staining) with the percentage of cells that are positive for staining (i.e., uniformity). An H-score can be calculated as follows:

$H$ score=[0*(percentage of cells staining at intensity 0)]+[1*(percentage of cells staining at intensity 1)]+[2*(percentage of cells staining at intensity 2)]+[3*(percentage of cells staining at intensity 3)].

Accordingly, an H-score can range from 0 (no cell staining) to 300 (all cell staining at intensity 3). The overexpression of both MYC and BCL2 has been described in DLBCL patients with poor prognosis. The synergy score obtained for

TABLE 10

IMGN529 and Anti-CD20 Antibody Synergy in Non-Hodgkin's Lymphoma Cell Lines

| IMGN529 x | HBL-1 | OCI-Ly10 | SU-DHL-2 | TMD8 | U-2932 | DOHH-2 | OCI-Ly1 | OCI-Ly7 | RL | SU-DHL-10 |
|---|---|---|---|---|---|---|---|---|---|---|
| Obinutuzumab | 8.88 | 0.092 | 12.8 | 1.03 | 25.1 | 14.5 | 3.58 | 20.4 | 2.18 | 5.02 |
| Ofatumumab | 233 | 0.0278 | 11.3 | 1.56 | 48.9 | 25.1 | 3.41 | 62.9 | 5.45 | 9.91 |
| Rituximab | 19.8 | 0.112 | 7.34 | 6.07 | 41.6 | 14.4 | 5 25 | 50 | 4.02 | 18.2 |

| IMGN529 x | SU-DHL-4 | SU-DHL-6 | WSU-NHL | JVM-13 | GRANTA-519 | Jeko0 | JVM-2 | MAVER-1 | Nama-Iwa | Ramos |
|---|---|---|---|---|---|---|---|---|---|---|
| Obinutuzumab | 10.2 | 0.685 | 1.64 | 7.34 | 6.22 | 2.46 | 4.94 | 5.82 | 0.0837 | 8.6 |
| Ofatumumab | 14.5 | 2.42 | 7.6 | 28.7 | 11.4 | 6.2 | 7.5 | 15.4 | 1.2 | 44 |
| Rituximab | 9.44 | 1.82 | 5.55 | 303 | 16.6 | 4.66 | 8.24 | 17.5 | 2.49 | 33.1 |

Figure 1:
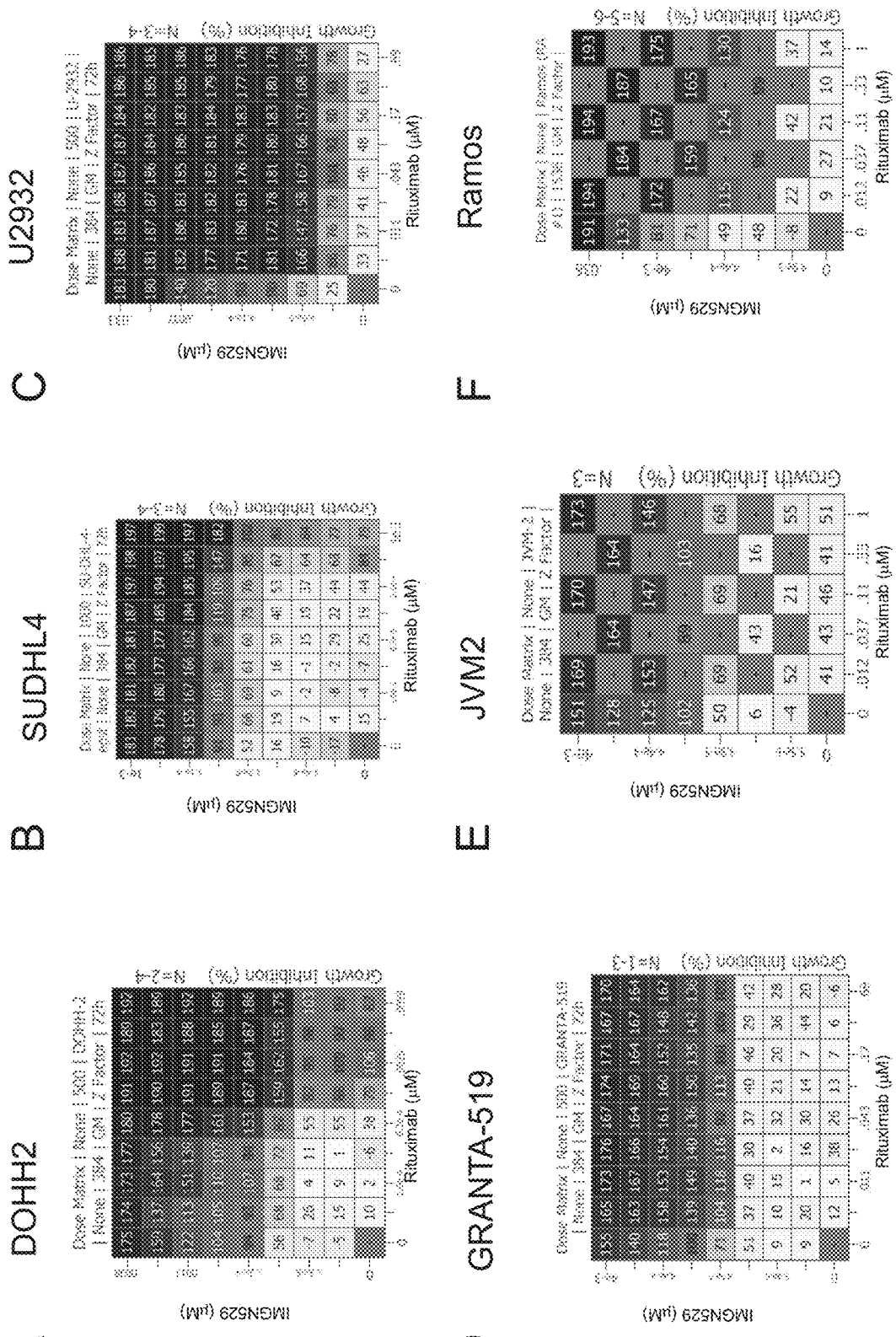
Figure 2:
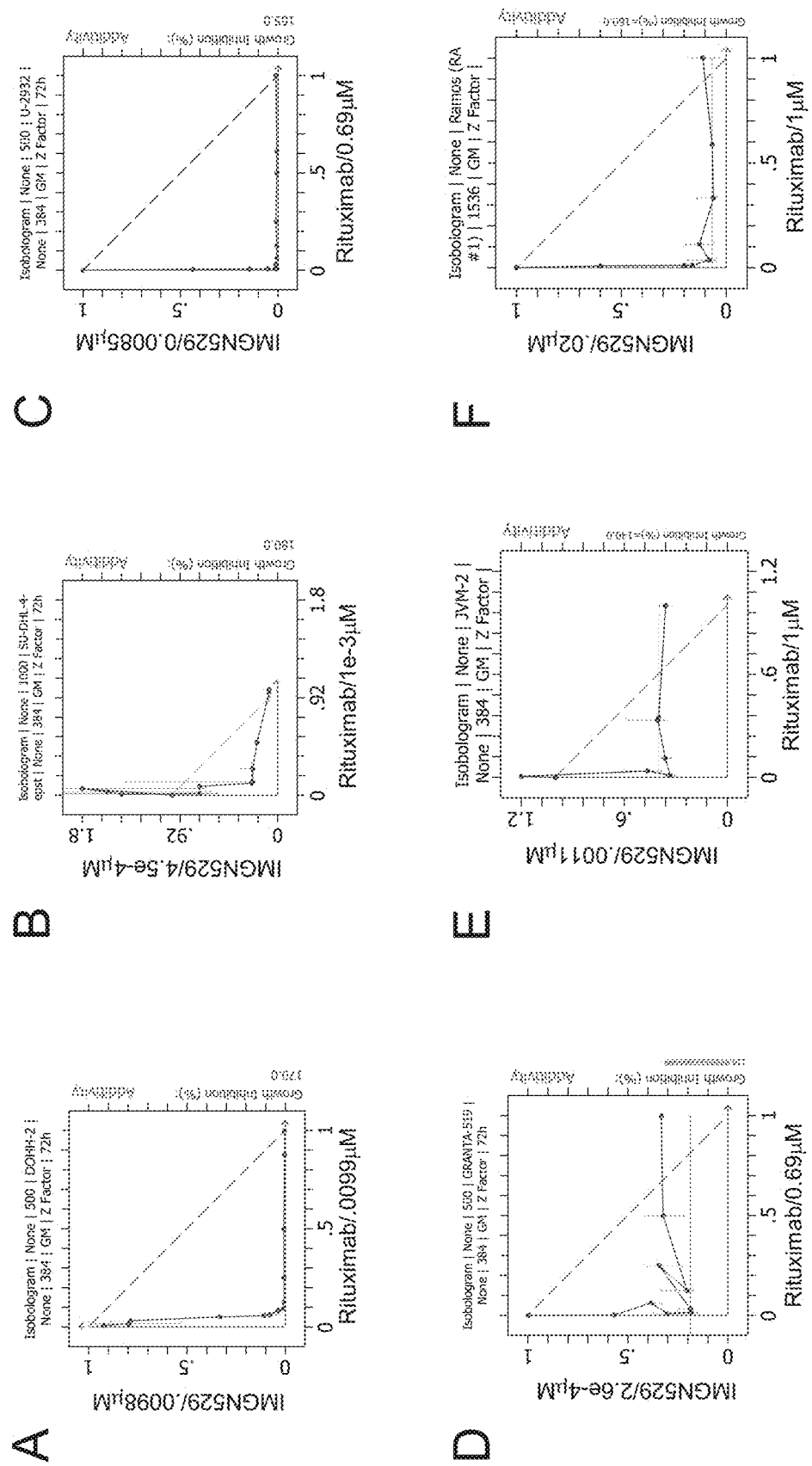

Underlined boxes indicate synergy scores that exceed self - cross X2 standard deviations The combination data for IMGN529 and rituximab are provided for five cell lines representative of each subtype of NHL. The data are presented as percent (%) growth inhibition at each dose of IMGN529 and rituximab (FIG. 1, panels a-f), isobolograms (FIG. 2, panels a-f), and the best combination index (CI) values (Table 11). Maximum growth inhibition that can be achieved under the conditions of this study is 200%.

TABLE 11

IMGN529 and Anti-CD20 Combination Index Scores
IMGN529 + Rituximab

| Cell line | Best CI value |
|---|---|
| SUDHL-4 | 0.36 |
| DOHH2 | 0.11 |
| U2932 | 0.013 |
| GRANTA-519 | 0.22 |
| JVM2 | 0.34 |
| Ramos | 0.17 |

Figure 3:
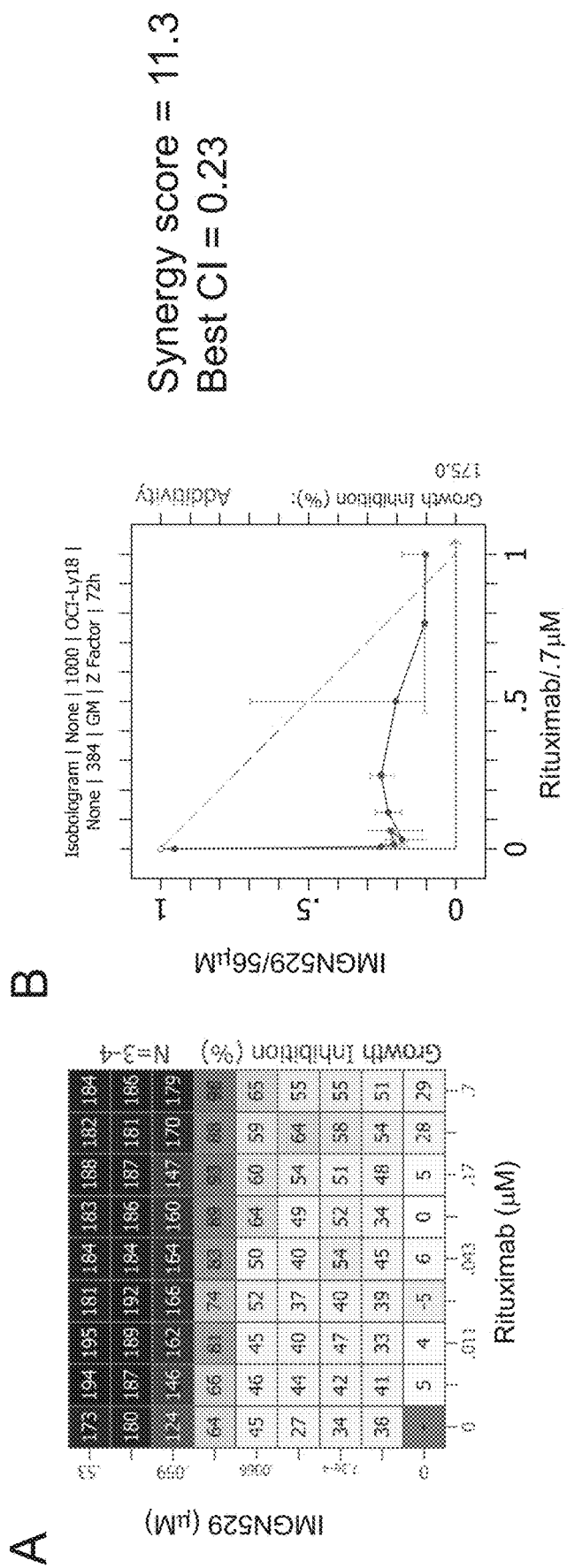

A CI value of less than 1 indicates synergism; CI=1 indicates additivity; and a CI of greater than 1 indicates antagonism. The representative isobolograms all show synthe rituximab+IMGN529 combination in OCI-Ly18 is 11.3 which is statistically significant. The isobologram and percent growth inhibition shown in FIG. 3, panels A and B, illustrate the synergy, and the best CI was determined as 0.23.

Figure 4:
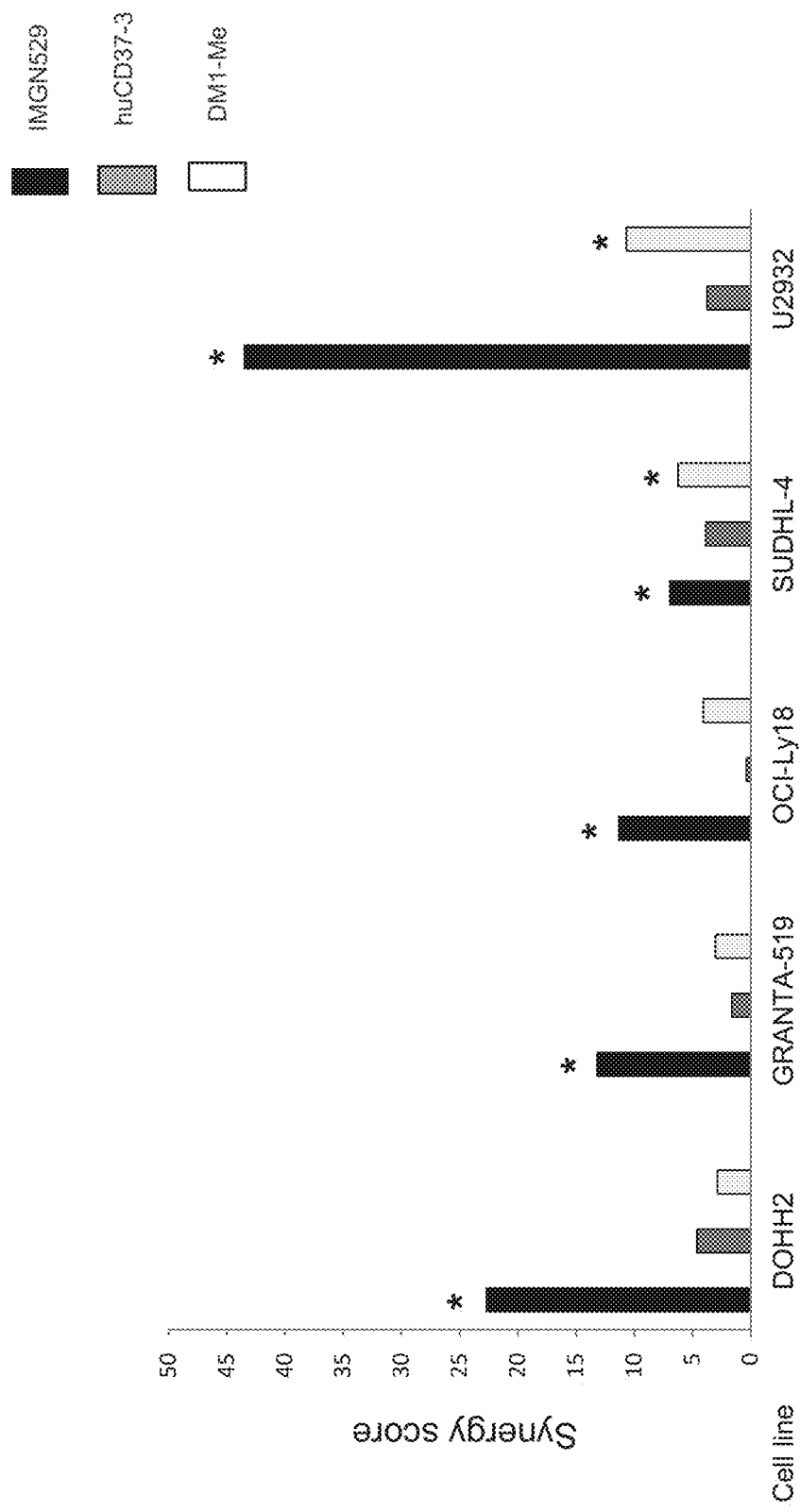

In order to look at the contribution of the individual components of IMGN529, an experiment was conducted to evaluate rituximab in combination with IMGN529, the unconjugated cell permeable DM1-Me, and the huCD37-3 anti-CD37 antibody in the following representative cell lines: DOHH2, GRANTA-51, OCI-Ly18, SUDHL-4 and U2932. The bar graph in FIG. 4 depicts synergy scores obtained. Statistically significant synergy scores are indicated with an asterisk. Rituximab shows synergy with IMGN529 in all five cell lines tested. The huCD37-3 antibody did not show statistically significant synergy in any of the five cell lines tested. The DM1-Me conjugate did show significant synergy in two cell lines: SUDHL-4 and U2932, but to a lesser extent. These data suggest that both the huCD37-3 antibody and the DM1-Me activity in IMGN529 are required for full synergy.

To identify if the synergy of the IMGN529 plus rituximab combination was driven by either single agent activity, the activity of either single agent was compared to the synergy score for the panel of NHL cell lines. The sensitivity of a panel of NHL cell lines was determined using a 72 hour viability assay (ATP lite, Perkin Elmer) by Horizon discovery.

Sensitivity of the cell lines was measured using the area under the curve (AUC) of the response curve. Cells were seeded in growth media in black 384-well tissue culture treated plates at 500 cells per well. At the time of treatment (48 hours after seeding ($T_0$)), a set of assay plates (which do not receive treatment) was collected and ATP levels were measured by adding ATPLite (Perkin Elmer). These Tzero ($T_0$) plates were read using ultra-sensitive luminescence on Envision Plate Readers. Treated assay plates were incubated with compound for 72 hours. After 120 hours, plates were developed for endpoint analysis using ATPLite. All data points were collected via automated processes, quality controlled, and analyzed using Horizon CombinatoRx proprietary software. Assay plates were accepted if they passed the following quality control standards: (1) relative luciferase values consistent throughout the entire experiment, (2) Z-factor scores greater than 0.6, and (3) untreated/vehicle controls consistent on the plate. GI was utilized as a measure of cell viability. The cell viability of vehicle was measured at the time of dosing ($T_0$) and after 120 hours ($T_{72}$).

Figure 9:
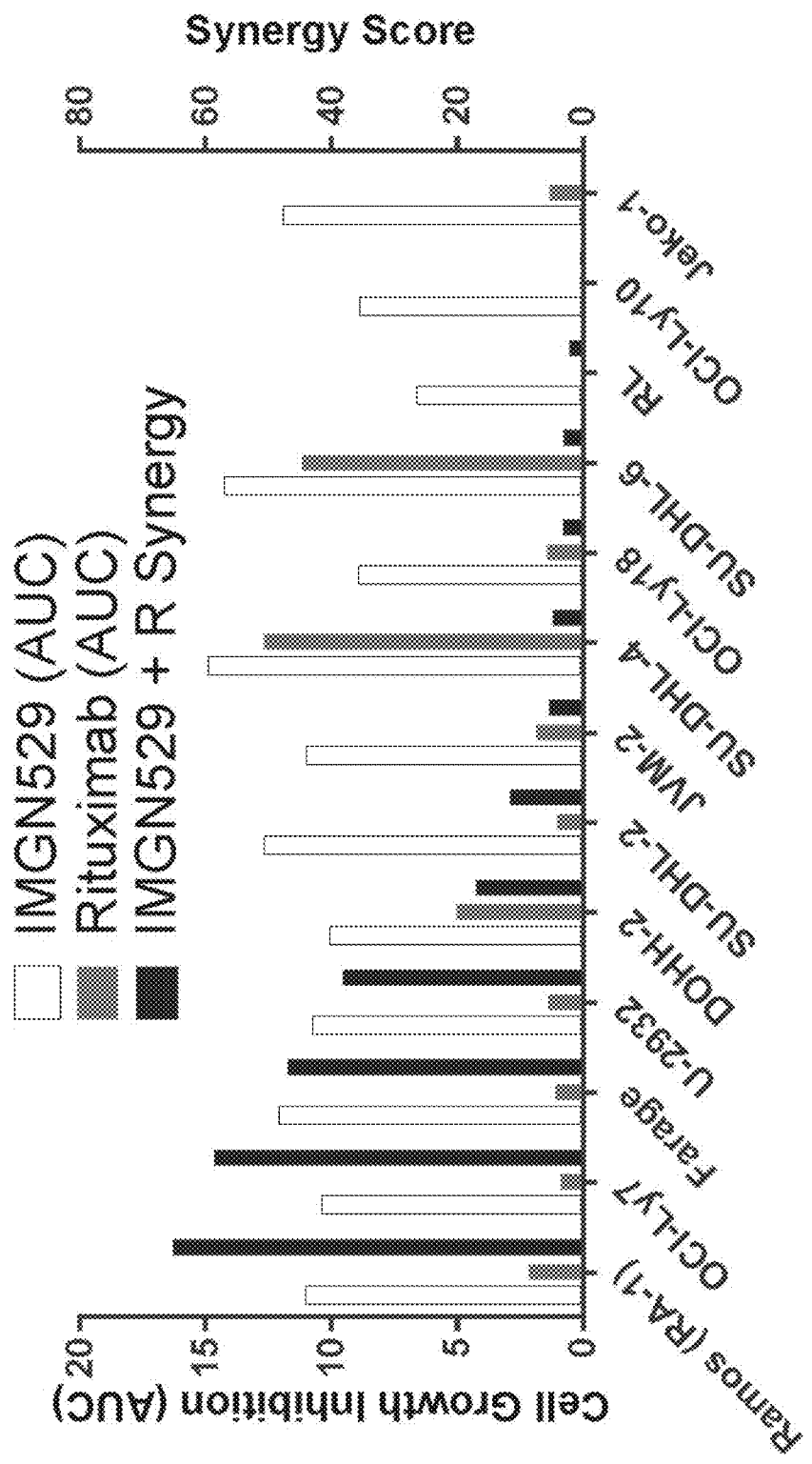

As shown in FIG. 9, the synergy of the combination of IMGN529 plus rituximab is not predicted by the single agent activity of either drug, suggesting a synthetic-lethal type interaction.

Figure 10:
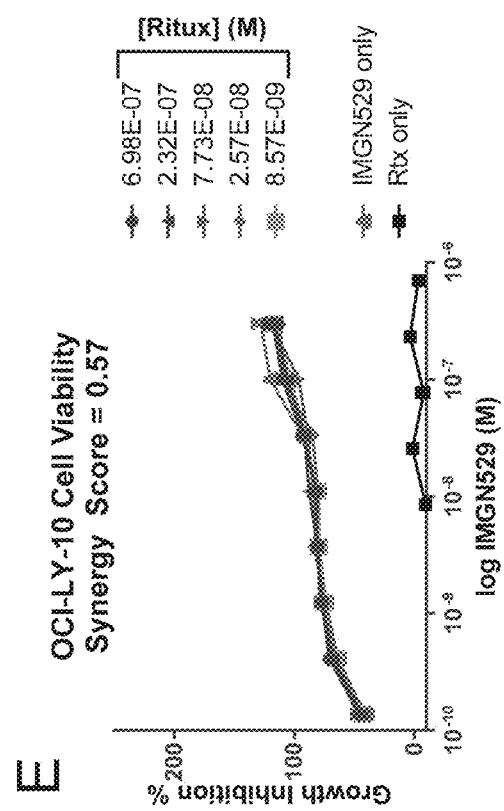
Figure 10:
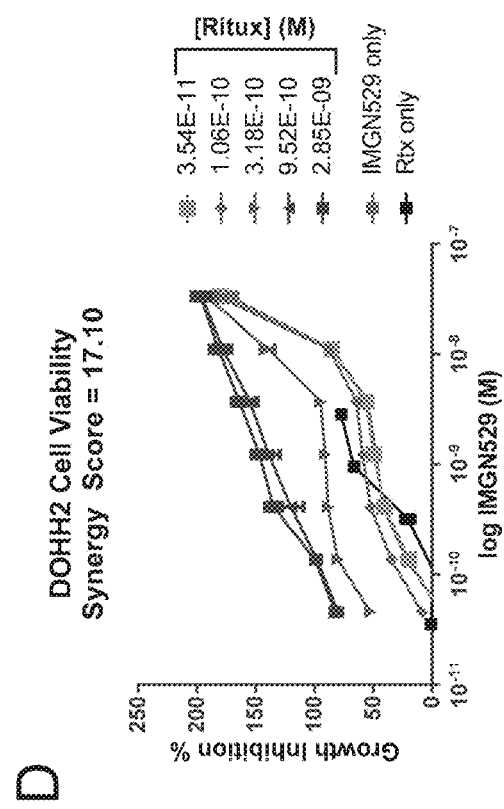

The combination of IMGN529 plus rituximab on reducing cell viability was recapitulated in the U2932 (ABC DLBCL), Farage (GCB DLBCL), OCI-Ly-7 (GCB DLBCL), OCI-Ly-10 (ABC DLBCL), and DOHH2 (GCB DLBCL) cells lines. The results are shown in FIG. 10, panels A-E. In the high synergy score cell lines (e.g., U2932, OCI-Ly7, and Farage, FIG. 10, panels A-C), low doses of rituximab reduced the dose of IMGN529 required for maximal cell killing. These results also suggest potent cell killing capabilities by the combination of IMGN529 plus rituximab in both the ABC and GCB DLBCL subtypes. In the lower synergy score cell lines (e.g., DOHH2, FIG. 10, panel D), there was a dose dependent synergy relative to rituximab. In cell lines with low/non-significant synergy (e.g., OCI-Ly-10, FIG. 10, panel E), there was no benefit from the addition of rituximab.

Example 2

In Vivo Efficacy IMGN529 and Rituximab Combination Therapy

To test the efficacy of IMGN529 for the ability to decrease tumor burden in vivo a disseminated tumor survival model was used, as described in the protocol below.

Female SCID mice were each inoculated intravenously in the lateral tail vein with $1\times10^7$ Farage cells, a human DLBCL cell line. On day 7 post-inoculation the mice were divided into groups, and treated by intravenous injection with IMGN529 alone or in combination with rituximab as outlined in Table 12 below. IMGN529 was administered once on day 7 at a dose of 2.5 or 5 mg/kg. Rituximab was dosed on days 7 and 21 post-inoculation in the monotherapy arm, and on days 7, 14, and 21 in the combination arms. Animals were monitored daily, and the measured end-point was survival. Animals were sacrificed when hind leg paralysis was present, body weight decreased by >20% of pre-treatment weight, or when any signs of distress were visible.

Figure 5:
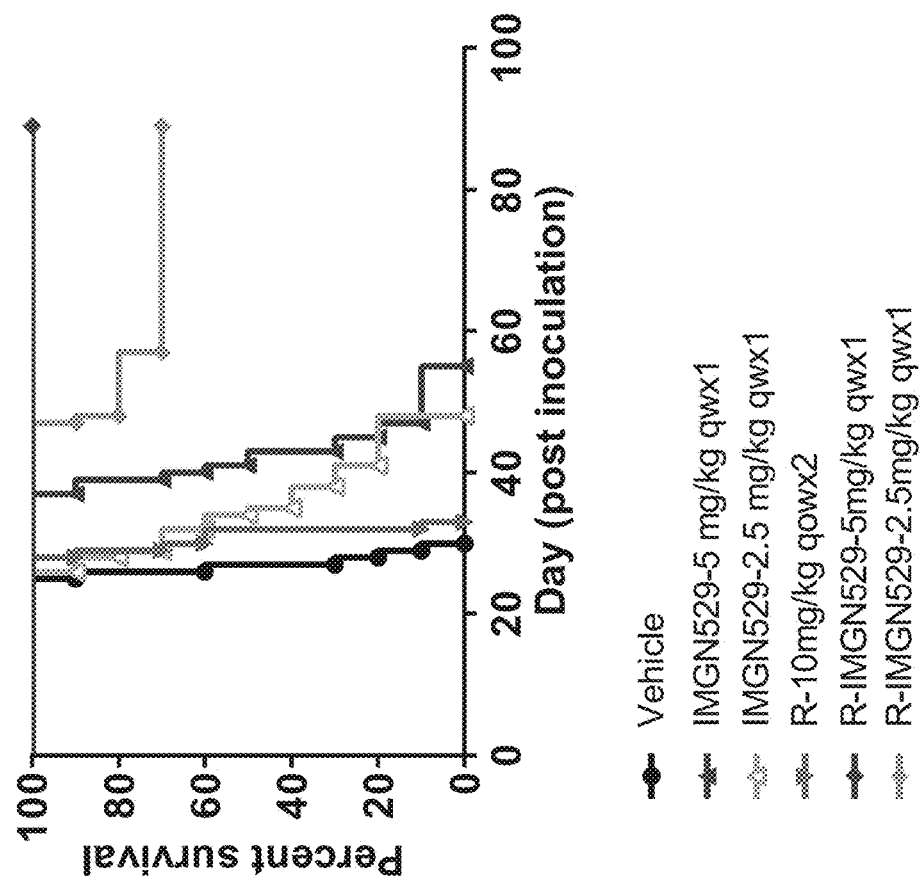

The results are shown in FIG. 5. The median survival time for vehicle treated animals was 27 days. Rituximab as a monotherapy increased the median survival time to 32 days. IMGN529 as a monotherapy dosed at 2.5 mg/kg and 5 mg/kg increased median survival to 34.5 and 42 days, respectively. The median survival time for animals treated with the combination of rituximab and IMGN529 was not determined because 7 of 10 animals treated with IMGN529 at 2.5 mg/kg in combination with rituximab and 10 of 10 animals treated with IMGN529 at 5 mg/kg in combination with rituximab were alive at day 90 post-inoculation of Farage cells. Thus, the combination of IMGN529 and rituximab dramatically increased survival time.

TABLE 12

Dosing Regimen and Results in Farage Mouse Model

| Group | Treatment | Dose (mg/kg) | Day(s) of dosing | Median survival (days) | Surviving animals (day 90) |
|---|---|---|---|---|---|
| A | vehicle | — | 7 | 27 | 0/10 |
| B | IMGN529 | 5 | 7 | 42 | 0/10 |
| C | IMGN529 | 2.5 | 7 | 34.5 | 0/10 |
| D | Rituximab | 10 | 7, 21 | 32 | 0/10 |
| E | IMGN529 | 5 | 7 | >90 | 10/10 |
|  | Rituximab | 10 | 7, 14, 21 |  |  |
| F | IMGN529 | 2.5 | 7 | >90 | 7/10 |
|  | Rituximab | 10 | 7, 14, 21 |  |  |

Example 3

Improved Efficacy and Toxicity of IMGN529 and Rituximab Combination Therapy in the SU-DHL-4, DLBCL Model The antitumor activity of IMGN529 was evaluated as a monotherapy and in combination with rituximab and R-CHOP combination chemotherapy in female SCID mice bearing SU-DHL-4 DLBCL lymphoma xenografts. Mice were randomized into groups (n=8 per group) by tumor volume and subsequently dosed on day 20 post inoculation. The groups included a control group dosed with vehicle (PBS), an IMGN529 single agent group dosed at 10 mg/kg, a single agent rituximab group dosed at 10 mg/kg, an IMGN529+rituximab combination group consisting of a 10 mg/kg dose of IMGN529 in combination with a single dose of rituximab at 10 mg/kg, and a group dosed with the R-CHOP combination chemotherapy. The R-CHOP chemotherapy regimen consisted of a single 10 mg/kg dose of the CD20 targeting antibody rituximab, a single 30 mg/kg dose of the DNA alkylating agent cyclophosphamide, a single 2.5 mg/kg dose of the DNA intercalating agent doxorubicin, a single 0.375 mg/kg dose of the microtubule inhibitor vincristine, and 5 daily 0.15 mg/kg doses of the corticosteroid prednisone.

Tumor volumes were measured one to two times weekly in three dimensions using a caliper. The tumor volume was expressed in $mm^3$ using the formula V=Length×Width×Height×½ (Tomayko and Reynolds, *Cancer Chemother. Pharmacol.* 24: 148-54 (1989)). Body weights were measured twice per week as a rough index of test agent toxicity. Activity was assessed as described in Bissery et al., *Cancer Res.* 51: 4845-52 (1991).

Tumor Growth Inhibition (T/C Value) was also assessed using the following formula:

T/C (%)=Median tumor volume of the treated/Median tumor volume of the control×100

Tumor volume was determined simultaneously for treated (T) and the PBS control (C) groups when tumor volume of the PBS control reached predetermined size. (Bissery et al., Cancer Res. 51: 4845-52 (1991).) The daily median tumor volume of each treated group was determined, including tumor-free mice (0 mm$^3$). According to NCI standards, a T/C ≤42% is the minimum level of anti-tumor activity. A T/C <10% is considered a high anti-tumor activity level.

Tumor Growth Delay (T–C) was also assessed. For the tumor growth delay (T–C) calculation, T and C are the median times (in days) required for the treatment group (T) and the PBS control (C) group tumors, respectively, to reach the predetermined size. Tumor free survivors are excluded from the calculations.

Tumor Doubling Time ($T_d$) was also is estimated from a nonlinear exponential curve fit of the daily median tumor volume of PBS control group.

Log Cell Kill (LCK) was also assessed. For subcutaneous growing tumors, the total log cell kill (LCK) is calculated from the following formula:

LCK=(T–C value in days)/(3.32×$T_d$)

where T–C is the tumor growth delay as described above and $T_d$ is the tumor volume doubling time in days. The log cell kill value can be converted to an activity rating according to the Southern Research Institute (SRI) criteria:

| SRI Activity Criteria | Log Cell Kill Gross |
|---|---|
| Highly active ++++ | >2.8 |
| +++ | 2.0 to 2.8 |
| ++ | 1.3 to 1.9 |
| + | 0.7 to 1.2 |
| Inactive – | <0.7 |

Tumor regression was also assessed. A subject was considered to have a partial regression (PR) when tumor volume was reduced by 50% or greater or have complete tumor regression (CR) when no palpable tumor could be detected. The number of tumor-free survivors (TFS) is the number of subjects that were tumor free at the end of the study (90 days post inoculation). Body weight of all the mice was measured once to twice per week as an index of drug toxicity.

Figure 6:
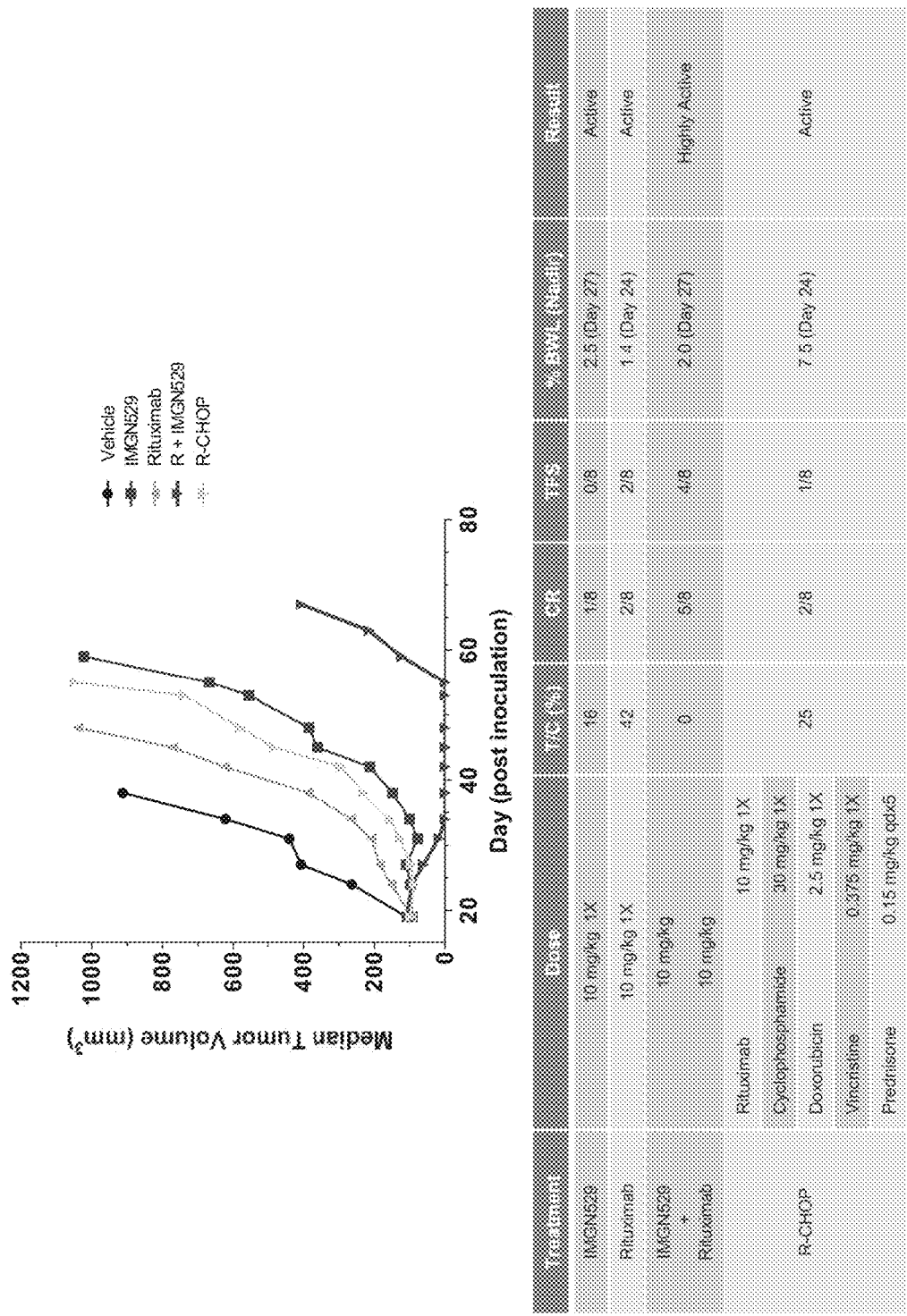

IMGN529 was active as a monotherapy (T/C of 16%, 1/8 CRs, and 0/8 TFS). Single dose rituximab was also active as a monotherapy (T/C of 42%, 2/8 CRs, and 2/8 TFS). R-CHOP therapy was active in the model (25% T/C, 2/8 CRs and 1/8 TFS). The IMGN529+rituximab combination was highly active (0% T/C, 5/8 CRs and 4/8 TFS). Single agent therapy as well as the IMGN529+rituximab combination therapy resulted in minimal nadir body weight loss (BWL) (2.5, 1.4 and 2.0% for the IMGN529, rituximab and IMGN529+rituximab groups, respectively). R-CHOP treatment resulted in appreciably more BWL at nadir (7.5%) compared to the IMGN529+rituximab combination (2.0%) (FIG. 6).

Example 4

Improved Efficacy of IMGN529 and Rituximab Combination Therapy in the DOHH2, Follicular Lymphoma (FL) Model The antitumor activity of IMGN529 was evaluated as a monotherapy and in combination with rituximab in female SCID mice bearing DoHH2 FL xenografts. Mice were randomized into groups (n=8 per group) by tumor volume and subsequently dosed on day 10 post inoculation. The groups included a control group dosed with vehicle (PBS), two IMGN529 single agent groups dosed at 10 mg/kg once every three weeks (qwx3) and 5 mg/kg qwx3, a rituximab single agent group dosed at 10 mg/kg qwx3, a R-CHOP group, and two IMGN529+rituximab combination groups receiving a 10 mg/kg qwx3 dose of rituximab in combination with IMGN529 at 10 mg/kg qwx3 or 5 mg/kg qwx3. The R-CHOP chemotherapy regimen consisted of a single 10 mg/kg dose of the CD20 targeting antibody rituximab, a single 30 mg/kg dose (iv) of the DNA alkylating agent cyclophosphamide, a single 2.5 mg/kg dose (iv) of the DNA intercalating agent doxorubicin, a single 0.375 mg/kg dose of the microtubule inhibitor vincristine (iv), and 5 daily 0.15 mg/kg doses (qdx5po) of the corticosteroid prednisone.

Tumor volumes and body weights were measured as described above.

Figure 7:
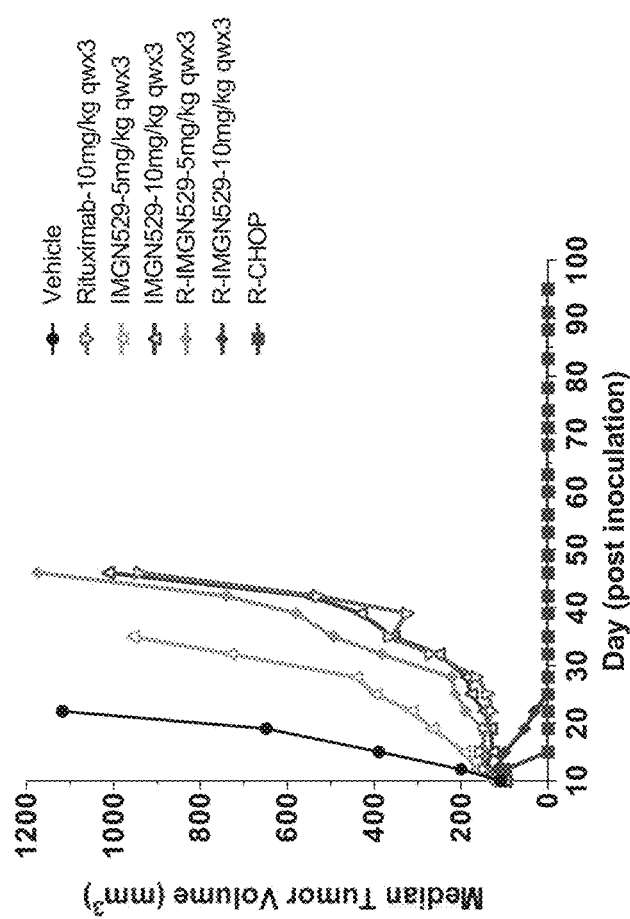

FIG. 7 provides the data. IMGN529 demonstrated dose dependent activity with 14% and 30% T/C, 1.14 and 2.13 LCK, 1/8 and 0/8 PR, 1/8 and 0/8 CR, 1/8 and 0/8 TFS for the 10 and 5 mg/kg qwx3 doses respectively. Both doses of IMGN529 were active by T/C values. Using SRI criteria, 5 mg/kg was + and 10 mg/kg was ++. As a monotherapy, rituximab was also active at 10 mg/kg qwx3 (13% T/C, 1.69 LCK, 3/8 PR, 3/8 CR, and 2/8 TFS). The combination of 10 mg/kg rituximab qwx3 with 5 mg/kg qwx3 IMGN529 was as active as monotherapy IMGN529 or rituximab (18% T/C, 1.69 LCK, 1/8 PR, 1/8 CR, 0/8 TFS). The combination of 10 mg/kg rituximab qwx3 with 10 mg/kg qwx3 IMGN529 was more active than the agents dosed as monotherapies (4% T/C, 2.13 LCK, 7/8 PR, 7/8 CR, 7/8 TFS). This combination was +++ active by SRI standards. Thus, the combination of an LCK++ active dose of IMGN529 (10 mg/kg) and rituximab was highly effective. R-CHOP was used for comparison in the study. The activity of combination IMGN529+rituximab when both agents were dosed at 10 mg/kg qwx3 was comparable to R-CHOP (4% vs 0% T/C, 2.13 vs 3.11 LCK, 7/8 vs 8/8 PR, 7/8 vs 8/8 CR, 7/8 vs 5/8 TFS). The IMGN529 vs rituximab combo treated mice lost slightly less weight than R-CHOP treated mice (3% vs 5%).

Example 5

IMGN529 and Rituximab Induce Apoptosis by Caspase Activation

Both IMGN529 and huCD37-3 can induce apoptosis in vitro in the absence of cross-linking IMGN529 shows enhanced cell killing activity as it combines the functional activity of the antibody component with targeted DM1 payload delivery. The mechanism of cell killing by IMGN529 alone or in combination with rituximab was studied by evaluating the induction of caspase 3 and 7 activities.

In these studies, cells were incubated at 10,000 cells per well in 100 µL RPMI-1640 media supplemented with 10% fetal bovine serum (FBS) in the presence of various treatments for 1 day in a humidified 37° C. incubator. Treatments were 10 nM huIgG1 isotype control antibody, 10 nM rituximab, 10 nM huCD37-3 antibody, 1 nM IMGN529, or a combination thereof. Staurosporine (Sigma-Aldrich), a potent inducer of apoptosis, was used as a positive control at 2 µM concentration. The Caspase-Glo® 3/7 assay kit (Promega) was used to detect Caspase 3/7 activity according to the manufacturer's instructions. Briefly, the Caspase- Glo® 3/7 buffer and lyophilized Caspase-Glo® 3/7 substrate were equilibrated to room temperature (RT) before use and then thoroughly mixed. The assay plates were removed from the incubator and allowed to equilibrate to RT and 100 µL of Caspase-Glo® 3/7 reagent were added to each well. Plates were gently mixed using an orbital plate shaker for 30 seconds to induce cell lysis. Assay plates were covered with foil and incubated at RT for 1 hour. The luminescence of each sample was measured in a Victor3 microplate reader (PerkinElmer) in relative luminescence units (RLU). Fold-induction of Caspase 3/7 was calculated for each treatment relative to huIgG1 isotype control antibody treated samples as mean RLU for each treatment divided by mean RLU from control sample. Data was plotted using GraphPad Prism v5 (GraphPad Software, Inc.).

Figure 8:
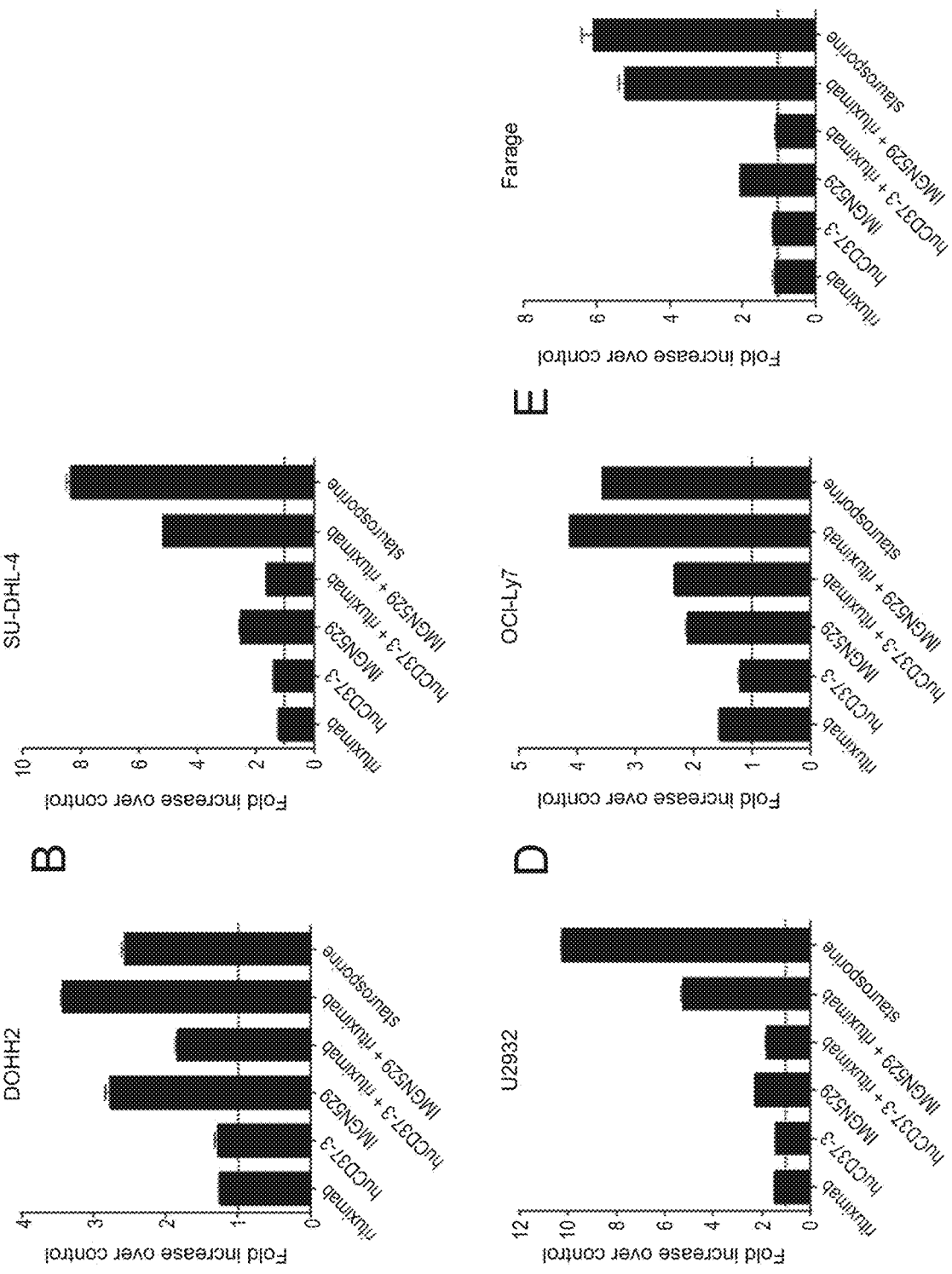

Results from these assays are presented in FIG. 8, panels A-E. IMGN529 induced Caspase 3/7 activity in a panel of CD37+ human lymphoma cell lines. IMGN529 treatment resulted in Caspase 3/7 activity that was approximately 1.8 to 2.5 times higher than the activity induced by the huIgG1 isotype control antibody in DOHH2, Farage, SU-DHL-4, U2932, and OCI-Ly7 cells. In combination with rituximab, IMGN529 induction of Caspase 3/7 activity increased in these cell lines and ranged from 3.4 to 5.2 times higher than the activity induced by the control antibody. These results indicates that IMGN529 induced cell death is associated with a caspase-mediated pathway. This is consistent with an apoptotic mechanism of cell death, and the activity can be enhanced by the presence of rituximab, an example of a Type 1 anti-CD20 antibody.

The combination effect of IMGN529 plus rituximab on Caspase 3/7 activation was also measured in replicate for the single agents and for pairwise combinations of the two agents at a series of concentrations, including zero as dose-combination matrices in the DOHH-2, OCI-Ly7, SU-DHL-4, and U2932 cell lines. Both single agents were prepared as a 4× working stock of $4 \times 10^{-8}$ M. A ⅓ serial dilution of IMGN529 and a ¼ serial dilution for rituximab was generated in complete RPMI-1640 media. Test samples (IMGN529, rituximab or both) were added in duplicate at 25 µL/well into white-walled 96-well assay plates (Costa 3917). The wells with non-treated cells were used as growth control. Exponentially growing cells were re-suspended at $3 \times 10^5$/mL in complete RPMI1640 media and 50 µL/well were added into the assay plate. The final assay conditions corresponded to 15,000 cells per well with IMGN529 from $1 \times 10^{-8}$ M to $1.4 \times 10^{-11}$ M with/without rituximab from $1 \times 10^{-8}$ M to $3.9 \times 10^{-11}$ M. Plates were incubated as indicated for 1 day (24 hours) in a humidified 37° C. incubator. The Caspase-Glo® 3/7 assay kit (Promega, Cat #PAG8092) was used to detect Caspase 3/7 activity throughout this study according to the manufacturer's instructions. The results from these experiments, in FIG. 11, panels A-D, show that treatment with IMGN529 plus rituximab results in dramatic Caspase 3/7 activation, leading to cell death.

Figure 11:
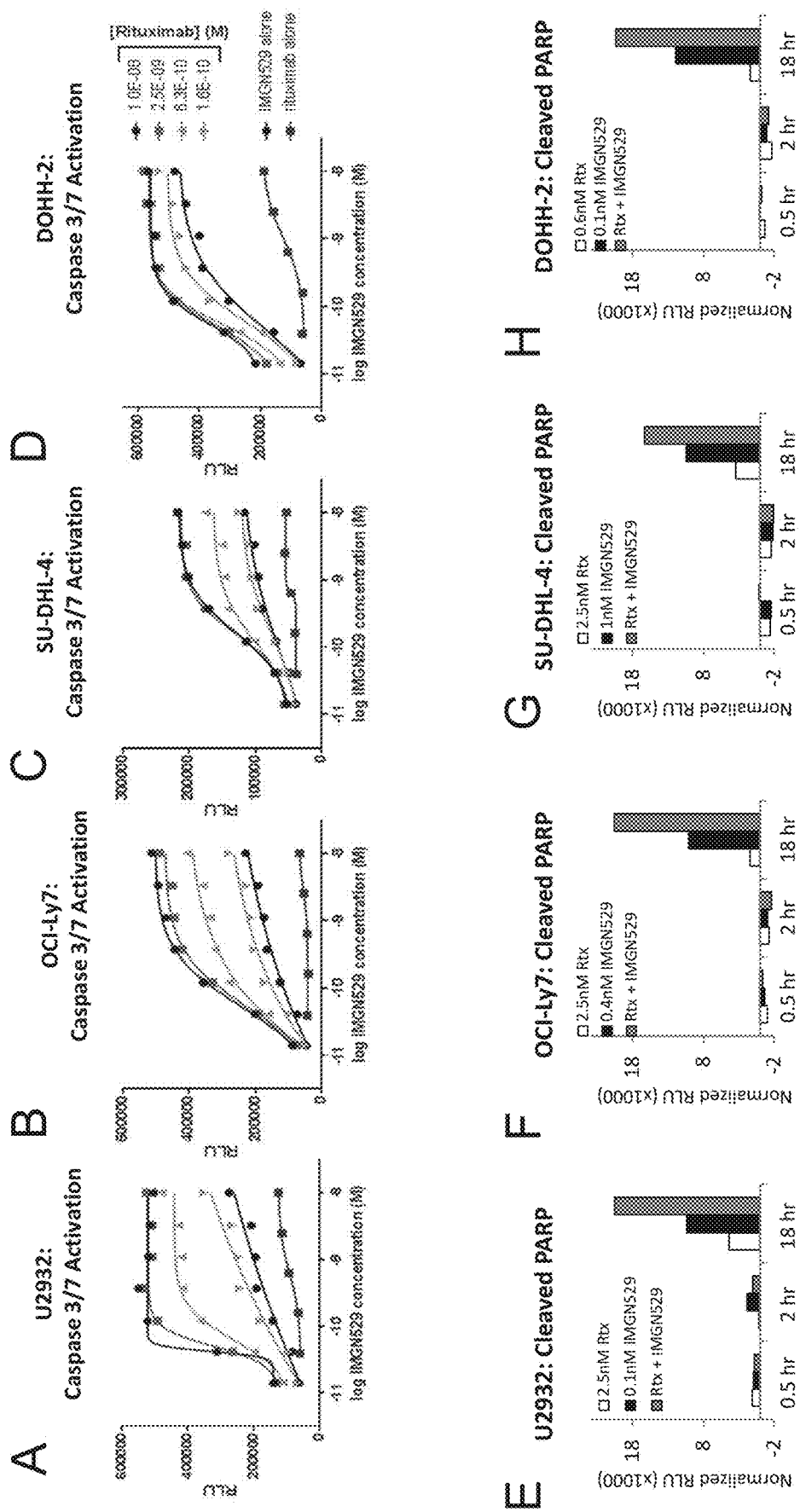

PARP cleavage was also examined following treatment with IMGN529 plus rituximab. Exponentially growing cells were harvested by centrifugation at 1,200 rpm for 5 minutes at RT and resuspended at $0.5 \times 10^6$/mL in complete RMPI-1640 medium. Cells were transferred to 10 mL per petri dish (Corning 430167) to equal $5 \times 10^6$ cells/dish. IMGN529 or rituximab or both were added at concentrations based on the results from the Caspase-Glo® 3/7 assay for each cell line. After incubation for 0.5 hours, 2 hours, and 18 hours, samples were collected and washed with 10 mL ice-cold 1×PBS. Pathscan stress and apoptosis signaling antibody array kit and PathScan intracellular signaling array kit (Cell Signaling #12856 and #7323) were used to detect the signaling molecules affected by the treatments according to the manufacturer's instructions. Briefly, cells were lysed with lysis buffer supplied by the kit with Halt protease and phosphatase inhibitor cocktail (thermo Scientific, prod #1861281). The lysates were normalized to 1 mg/mL and 50-75 µL of lysate were incubated with the array membranes. The arrays were incubated with detection antibody cocktail at RT for 1 hour followed by HRP-linked streptavidin at RT for 30 minutes. Slides were incubated with LumiGlo/Peroxide reagent and imaged using the Bio-Rad chemiDoc MP image system. Densitometry analysis was performed and data was exported and analyzed in Microsoft Excel. The RLU for each treatment relative to untreated control samples was calculated as the mean RLU for each treatment minus the mean RLU from untreated sample at each time point. As shown in FIG. 11, panels E-H, incubation of cells with IMGN529 plus rituximab for 18 hours increased cleavage of PARP, indicating that the cells are undergoing apoptosis.

Example 6

Study of IMGN529 in Combination with Rituximab in Patients with Relapsed or Refractory Diffuse Large B Cell Lymphomas The combination of IMGN529 and rituximab is tested for its efficacy and tolerability on relapsed and/or refractory Diffuse Large B Cell lymphomas and other forms of Non-Hodgkin's Lymphoma in human patients.

Study Design

In an open label, multicenter, non-randomized phase II (with safety run-in phase) study IMGN529 is administered in combination with rituximab to patients with relapsed and/or refractory Diffuse Large B-cell lymphomas (DLBCL) and other forms of Non-Hodgkin's Lymphoma. The study consists of a screening period, a treatment period, an end of treatment visit, and a follow-up period. Patients with DLBCL, follicular NHL (FL), Mantle Cell Lymphoma (MCL), or Marginal Zone/Mucosa-associated lymphoid tissue (MZL/MALT), or other NHL subtypes are eligible for enrollment in the safety run-in phase of the study. During the safety run-in, at least six DLBCL and six FL NHL patients are enrolled. In phase 2 of the study, patients are enrolled into two parallel cohorts according to disease diagnosis: Cohort 1, R/R DLBCL (approximately 30 patients; de novo or transformed) and Cohort 2, other subtypes of R/R NHL (approximately 30 patients).

Patients are given dexamethasone IV at 10 mg (or equivalent), antihistamines and antipyretics approximately 30-60 minutes prior to the IMGN529 infusion. Patients are instructed to take oral dexamethasone at 8 mg/daily on days 2 and 3 following the infusion. If necessary, patients are treated with granulocyte growth factor support. If granulocyte growth factor support is given, it is administered starting between days 6-10 of each cycle for as many days as deemed necessary by the treating physician to mitigate neutropenia. Patients with high tumor burden and/or high circulating lymphocyte counts ($>25 \times 10^9$/L) are at greater risk for tumor lysis syndrome (TLS) and are adequately hydrated beginning 12-24 hours prior to treatment. Patients are to receive prophylactic antiviral treatment as per institutional guidelines.

Adult patients with refractory or relapsed DLBCL, FL, MZL/MALT, MCL, or other forms of NHL, who have received at least one but no more than 6 prior lines of therapy/prior treatment regimens (prior anti-CD20 therapy, either alone or in combination, is allowed) are enrolled. Patients must have evaluable or measurable disease in accordance with the International Working Group Guidelines for Lymphoma (Cheson et al., J. Clin. Oncol. 25(5), 2007). Patients who have FDG-avid disease must be able to be followed by PET-CT from baseline through the end of study. Patients must have adequate blood counts and organ function and be willing to provide a fresh tumor biopsy unless archived tissue is available rom a biopsy that has been collected within the year preceding study enrollment. Primary refractory disease is defined as achieving less than a PR in a first therapy or relapsing from a response to a first-line of therapy within six months for the safety run-in phase only. Patients who have received prior allogeneic stem cell transplantation are excluded from the safety run-in phase of the study; however are allowed to enroll in Phase 2 if their graft versus host disease (GVHD) is controlled and the sponsor approves. Patients with ≥Grade 2 peripheral neuropathy, pregnant, breast feeding, or who have active hepatitis A, B, or C infection or other uncontrolled intercurrent illness are excluded. Patients who have received prior therapy with other anti-CD37-targeting antibody drug conjugates are excluded.

IMGN529 and rituximab are administered intravenously at the maximum tolerated dose (MTD) as defined in a Phase I IMGN529 study (0.7 mg/kg or an alternate dose as determined by the Safety Review Committee (SRC) made up of medical directors and investigators from participating sites responsible for safety data review during the course of the trial), and 375 mg/m$^2$ respectively, on week 1, day 1 of a 3 week schedule (i.e., Q3W). Treatment emergent adverse events (TEAEs) occurring in the patients enrolled into the safety run-in phase is reviewed by the SRC and taken into consideration when determining the safety profile of the combination treatment. Once the Phase 2 dose is determined by the SRC, Cohorts 1 and 2 are opened and enrolled simultaneously, with rituximab and IMGN529 being administered at the same schedule used in the safety run-in phase. The combined therapy is provided for as long as tolerated in the absence of unacceptable toxicity, disease progression or withdrawal of consent. The primary aims of the study are to determine the anti-tumor activity and the tolerability of treatment with the IMGN529 and rituximab combination regimen as assessed by the objective response rate (ORR) and the incidence of adverse events. Anti-tumor activity will be assessed by the Lugano Classification. CTCAE version 4.03 will be used to grade adverse events.

Disease assessment using CT/PET scan of chest, neck, abdomen, and pelvis is performed at baseline (within 28 days prior to first dose of study treatment) and repeat assessments will be performed every 6 weeks±1 week, beginning at Cycle 1, Day 1 and will not shift as a result delays in study treatment, and at the end of treatment (EOT, 28 days after the last administration of study treatment). Though less preferred, a magnetic resonance imaging (MRI) is acceptable. Patients with FDG-avid disease will be followed by [18F]-FDG-PET scan. PET is repeated as necessary. If not performed within the prior 3 months before inclusion, bone marrow biopsy is done at baseline. It is repeated only if involved at baseline for confirming a complete response (CR). At the end of therapy, responders continue to have tumor assessments every 12 weeks (+/−3 (±4 weeks)) until documented progressive disease or initiation of a new lymphoma-specific therapy, whichever occurs earlier. All patients are followed for survival for at least 24 months.

Safety Data

Vital signs, physical examination, ECOG Performance Status (PS), and laboratory safety tests are obtained prior to drug administration and at designated intervals throughout the study in all patients. Changes from baseline in hematology, blood chemistry, vital signs, and ECG results are summarized by treatment. Shifts in hematology and blood chemistry from baseline values are summarized. Plasma also will be evaluated for the presence of humoral responses against the humanized anti CD37 antibody component or against the DM1 component. Adverse events are coded with the Medical Dictionary for Regulatory Activities and summarized per system organ class (SOC). Concomitant medications are coded using the World Health Organization Drug Dictionary. Pharmacokinetics are performed at designated intervals during the treatment. PK parameters ($C_{max}$, $T_{max}$, terminal half-life ($t_{1/2}$), volume of distribution at steady state ($V_{ss}$), clearance (Cl), $AUC_{0-t}$, $AUC_{inf}$) are derived from plasma concentrations of IMGN529, total humanized CD37 monoclonal antibody, DM1, and total rituximab using the actual sampling times. Individual plasma concentration vs. actual time profiles for each patient and treatment as well as the mean (+/−STD) plasma concentration vs. scheduled time profiles for each dose level are presented graphically on normal and semi-log scale. Tumor tissue samples are used for characterizing the patients' tumors and making correlations with disease outcome.

Efficacy Data

Data is analyzed to evaluate primary and secondary objectives. The primary objective is the determination of the efficacy and tolerability of IMGN529 in combination with rituximab. Objective response rate (ORR) is determined by the investigator for each evaluable patient as complete response (CR), partial response (PR), stable disease (SD), or relapsed disease/progressive disease (PD). Responses are tabulated by dose cohort assigned as well as the dose at which the response occurred along with the 95% confidence interval (CI). To meet the definition of response-evaluable, patients must have undergone radiographic assessment at baseline, received at least one dose of IMGN529 and rituximab, and must have had at least one post-dose tumor assessment. Secondary objectives include characterization of the pharmacokinetics and pharamacodynamics of the combination regimen. Patients are evaluated to demonstrate an increase in progression-free survival (PFS), time to progression (TTP), and overall survival (OS). PFS will be analyzed using the Kaplan-Meier method. Median PFS and 95% CI (if feasible) and the rate of PFS at six months and their 95% CI are estimated and presented. OS will be analyzed using the Kaplan-Meier method. Median OS and 95% confident intervals (if feasible) are presented. The OS rate at one year along with the 95% CI are estimated and presented. Time to response and duration of response (DOR) are also evaluated. DOR is estimated for all evaluable patients who achieve an objective response (PR or CR). Median duration and associated 95% CIs are presented. Exploratory objectives include investigating the correlation between anti-tumor activity of the combination regimen with CD37 and CD20 antigen expression with antitumor activity of IMGN529 and rituximab and to explore potential predictive and prognostic biomarkers including, but not limited to, cell of origin classification, MYC, BCL2, and IgVH status, expression profiling and mutational analysis of relevant genes as well as FcγRIIIA and/or FcγRIIA genotype.

Example 7

Improved Efficacy of IMGN529 and Rituximab Combination Therapy in SCID Mice Bearing U2932 Tumor Cells The antitumor activity of various doses of IMGN529 alone or in combination with rituximab compared to R-CHOP was evaluated in female SCID mice bearing U2932 tumor cells, an ABC DLBCL model. Thirteen days post inoculation, mice were randomized into 7 groups (n=8 per group) by tumor volume. The groups included a control group dosed with vehicle (PBS), IMGN529 at 5 mg/kg or 10 mg/kg, rituximab 10 mg/kg QWx3, IMGN529 5 mg/kg or 10 mg/kg in combination with rituximab 10 mg/kg QWx3, and R-CHOP chemotherapy regimen (consisting of a single 10 mg/kg dose of the CD20 targeting antibody rituximab, a single 30 mg/kg dose (iv) of the DNA alkylating agent cyclophosphamide, a single 2.5 mg/kg dose (iv) of the DNA intercalating agent doxorubicin, a single 0.375 mg/kg dose (iv) of the microtubule inhibitor vincristine, and 5 daily 0.15 mg/kg doses (qdx5po) of the corticosteroid prednisone).

Figure 12:
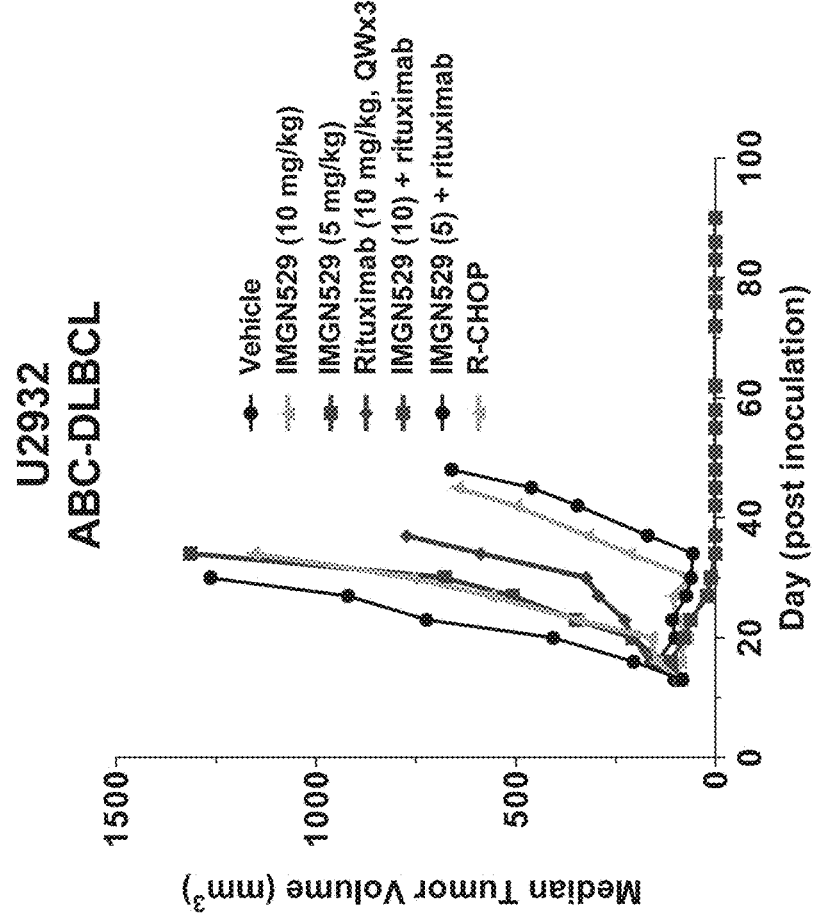

Tumor volumes and body weights were measured as described above and the results are shown in FIG. 12. Briefly, IMGN529 monotherapy at 5 mg/kg or 10 mg/kg was inactive in this model. IMGN529 monotherapy at 5 mg/kg had a T/C of 62%, 0/8 PR, and 0/8 CR at study end. IMGN529 at 10 mg/kg had a T/C of 55%, 0/8 PR, and 0/8 CR at study end. Rituximab 10 mg/kg QWx3 monotherapy was active with a T/C of 32%, 0/8 PR, and 0/8 CR at study end. The combination arms of IMGN529 5 mg/kg and 10 mg/kg with rituximab 10 mg/kg QWx3 were both highly active in this model. IMGN529 at 5 mg/kg in combination with rituximab 10 mg/kg QWx3 had a T/C of 2%, 7/8 PR, and 6/8 CR at study end. IMGN529 at 10 mg/kg in combination with rituximab 10 mg/kg QWx3 had a T/C of 8%, 4/8 PR, and 4/8 CR at study end. R-CHOP as a standard of care was also active in this model having a T/C of 12%, 4/8 PR, and 2/8 CR at study end. There was mean body weight loss (data not shown) observed in R-CHOP (4% nadir) but not in the monotherapy arms or combination therapy arms.

The results from this study and the studies in Examples 2 through 4 suggest that the combination of IMGN529 plus rituximab is efficacious in both ABC and GCB subtypes of DLBCL.

Example 8

IMGN529 and Rituximab Combination Down Regulates Anti-Apoptotic Protein and Proliferative Signaling in Both ABC and GCB DLBCL NHL Cell Lines The combination of IMGN529 and rituximab has a synergistic effect on tumor growth inhibition. The underlying molecular mechanisms of this synergy was evaluated by the levels and activities of various anti-apoptotic and proliferative molecular signaling pathways in both DOHH2 (GCB DLBCL) and U2932 (ABC DLBCL) cell lines.

Figure 13:
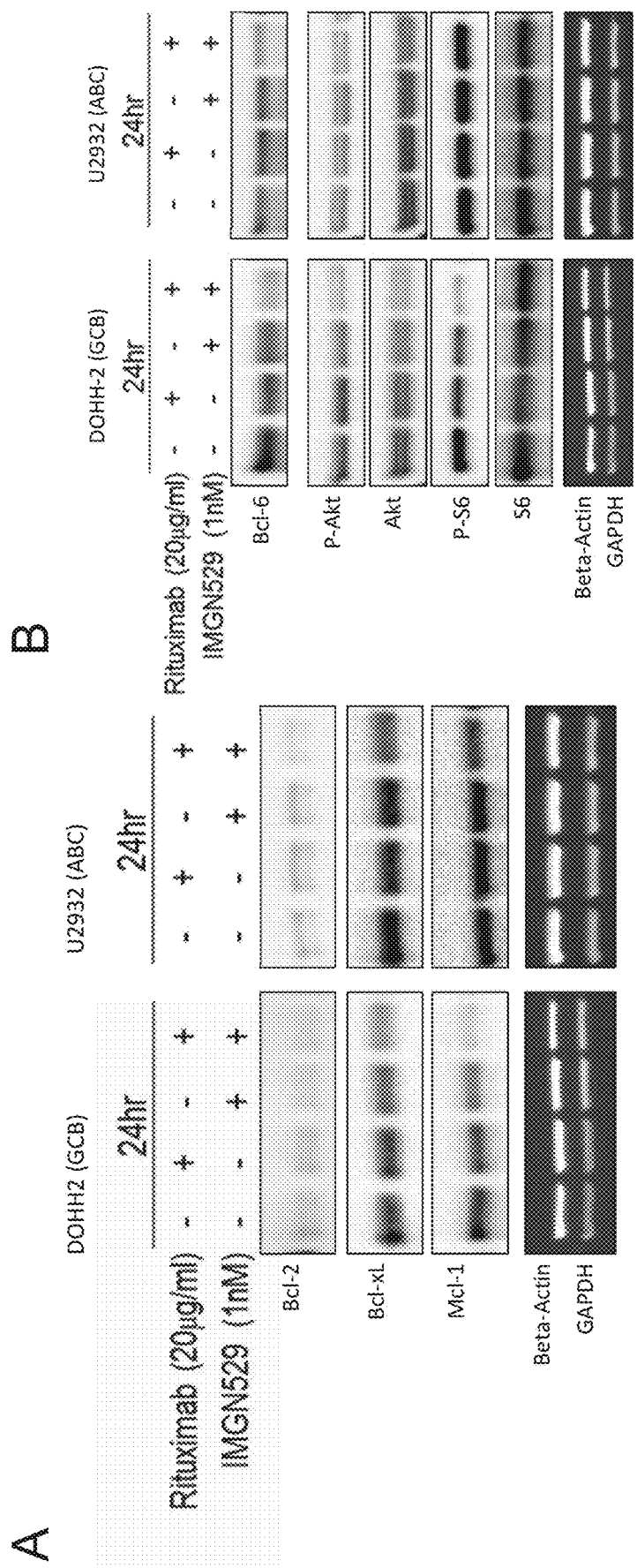

$1 \times 10^7$ cells were treated with IMGN529 and rituximab either alone or in combination for 24 hours. Cells were washed in PBS and harvested by centrifugation. Cells were re-suspended and lysed in M-PER (Pierce) containing both protease and phosphatase inhibitors for 10 minutes at 4° C. with periodic vortexing. Protein lysates were centrifuged to remove debris and the protein concentration was measured using the BCA assay (Pierce). Equivalent amounts of linearized protein were prepared for western blotting using XT-Sample Buffer and XT-Reducing Agent (BioRad) and by heating at 100° C. for 10 minutes on a heat block. Gel electrophoresis and western blotting were carried out as described in the manufacturer's instructions using the Criterion gels and equipment (BioRad). Proteins were transferred to PVDF membranes and protein levels assessed using appropriate primary and secondary antibodies (Cell Signaling Technologies). Equal protein loading was confirmed by blotting for the reference genes GAPDH and beta-Actin. The results are shown in FIG. 13, panels A and B.

Cells were treated with IMGN529 and rituximab at 1 nM and 20 µg/mL respectively. In the GCB DLBCL cell line DOHH2 and the ABC DLBCL cell line U2932, the combination of IMGN529 and rituximab decreased anti-apoptotic protein (BCL-XL, BCL-2, MCL-1) expression to a greater extent than single agent activities alone (FIG. 13, panel A). Similarly, the combination treatment down regulated the activity of the PI3K/AKT axis (as measured by phospo-AKT and phospho-S6 levels) to a greater extent than single agent treatments (FIG. 13, panel B).

Example 9

Improved Efficacy of IMGN529 and Rituximab Combination Therapy in OCI-Ly18 Double Hit DLBCL Tumor Xenograft The antitumor activity of the combination of IMGN529 and rituximab was evaluated in female SCID mice bearing OCI-Ly18 double hit DLBCL tumor xenografts. Mice were randomized into groups (n=8 per group) by tumor volume and subsequently dosed on day 12 post inoculation. All treatments consisted of single doses. The groups included a control group dosed with vehicle (phosphate buffered saline (PBS)), an IMGN529 single agent group dosed at 10 mg/kg, a rituximab single agent group dosed at 10 mg/kg, and an IMGN529+rituximab group dosed at 10 mg/kg and 10 mg/kg respectively.

Tumor volumes were measured one to two times weekly in three dimensions using a caliper. The tumor volume was expressed in mm3 using the formula V=Length×Width×Height×½ (Tomayko 1989). Body weights were measured twice per week as a rough index of test agent toxicity. Activity was assessed as described in Bissery et al. (1991).

Figure 14:
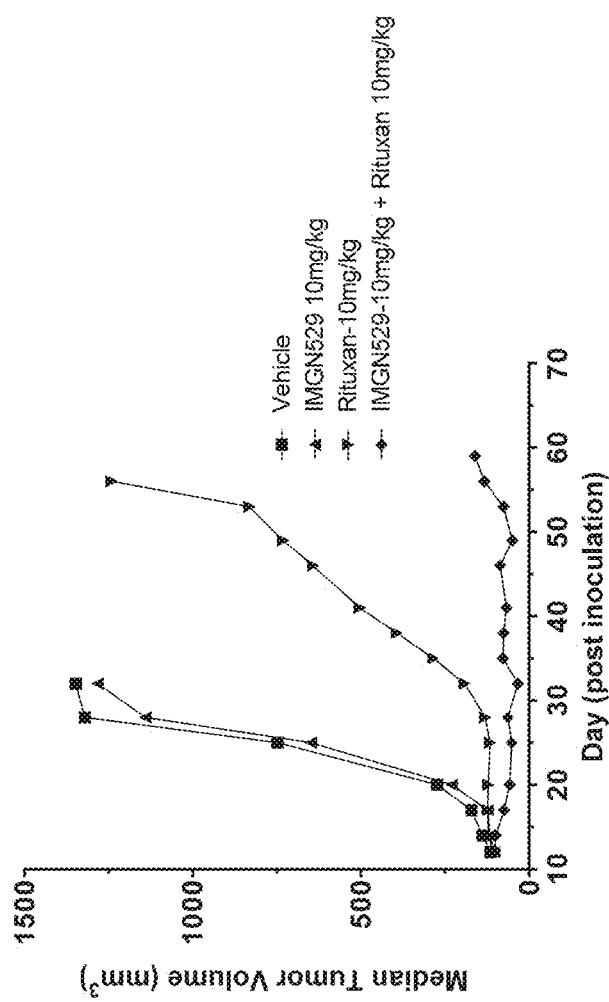
FIG. 14 shows the results of treating mice bearing OCI-Ly18 double hit DLBCL tumor xenografts with vehicle (PBS), IMGN529, rituximab, or a combination of IMGN529 and rituximab (R-IMGN529). T/C % represents tumor growth inhibition, TFS indicates tumor free survival, LCK indicates log cell killing, and BWL indicates body weight loss.

IMGN529 single agent was inactive (T/C of 88%, 0/8 CRs and 0/8 TFS). Rituximab single agent was active (T/C of 12%, 0/8 CRs and 0/8 TFS). The combination of IMGN529+rituximab was highly active (T/C of 0.1%, 2/8 CRs and 1/8 TFS). The combination IMGN529+rituximab was more active than all single agent treatments (see, FIG. 14).

Example 10

In Vitro Processing Model for IMGN529 and Rituximab Combination Therapy Shows Rituximab Co-Treatment Increases the Amount of Anti-CD37 Antibody Being Processed To assess the on-cell target binding, uptake and lysosomal degradation of IMGN529 alone and in combination with rituximab a previously-described $^3$H-propionamide-labeled antibody processing method was used (Lai et al., *Pharm Res.* 2015 November; 32(11):3593-603). Using this model, the anti-CD37 targeting moiety of IMGN529, the huCD37-3 antibody, was trace labeled with tritiated propionate via lysine residues. We have previously shown that upon cellular binding, uptake, and trafficking to the lysosome, [$^3$H] propionate labeled-Ab ($^3$H-Ab) is degraded and lysine-[$^3$H] propionamide is released. This single catabolite has been identified and quantified in amounts similar to the lys-SMCC-DM1 single catabolite from Ab-SMCC-DM1 conjugates such as IMGN529. Therefore to examine the IMGN529+/−rituximab cellular processing in vitro, a panel of DLBCL cell lines were treated with [$^3$H]propionate labeled-huCD37-3 antibody.

The following DLBCL cell lines, U2932, OCI-Ly7, SU-DHL-4, SU-DHL-6, Farage and DOHH2, were treated with 10 nM $^3$H-huCD37-3 antibody after determination of antigen saturation via binding curve. Some cells were pre-blocked with 500 nM (50×) unlabeled huCD37-3 antibody while others were untreated. Additional replicates were co-treated with either an anti-CD19 specific antibody, anti-CD20 specific antibodies (rituximab or GA101), and an anti-CD22 specific antibody, or non-targeting isotype control Ab (chKTI). CD19, CD20 and CD22 are B-cell markers co-expressed on DLBCL cells. Cells were pulse-treated with reagent(s) as previously described. Briefly, cells were incubated with $^3$H-huCD37-3 antibody+/−Ab(s) for 30 minutes before spinning and washing 3 times in fresh media. Cells were plated in 6-well plates and incubated overnight at 37° C. with 5% $CO_2$. After 20-24 hr. incubation cells were harvested and protein precipitated with 4:3 volume acetone: media/cell mixture. Samples were frozen at −80° C. for a minimum of 1 hr before thawing and separating by centrifuge. Pellets were treated to solubilize protein prior to counting for 5 minutes in a Tri-Carb liquid scintillation counter (LSC). Per manufacturer's protocol, 1 mL of SOLV-ABLE (Perkin Elmer) was added to each pellet sample and incubated in a 50° C. water bath overnight. Samples were removed from the water bath, transferred to 20 mL glass scintillation vials and EDTA and $H_2O_2$ were added to samples followed by an additional 1 hr 50° C. incubation. Samples were quenched with HCl, 15 mL of Optima Gold liquid scintillation fluid (Perkin Elmer) was added, and samples were vortexed thoroughly. Samples were kept in the dark for a minimum of 4 hr before counting by LSC. Protein-free acetone extract samples were dried to <1 mL volumes under vacuum and processed using Solvable as described above prior to LSC. The amount of bound, degraded, and intact labeled antibody were calculated from the resulting sample CPM values.

Figure 15:
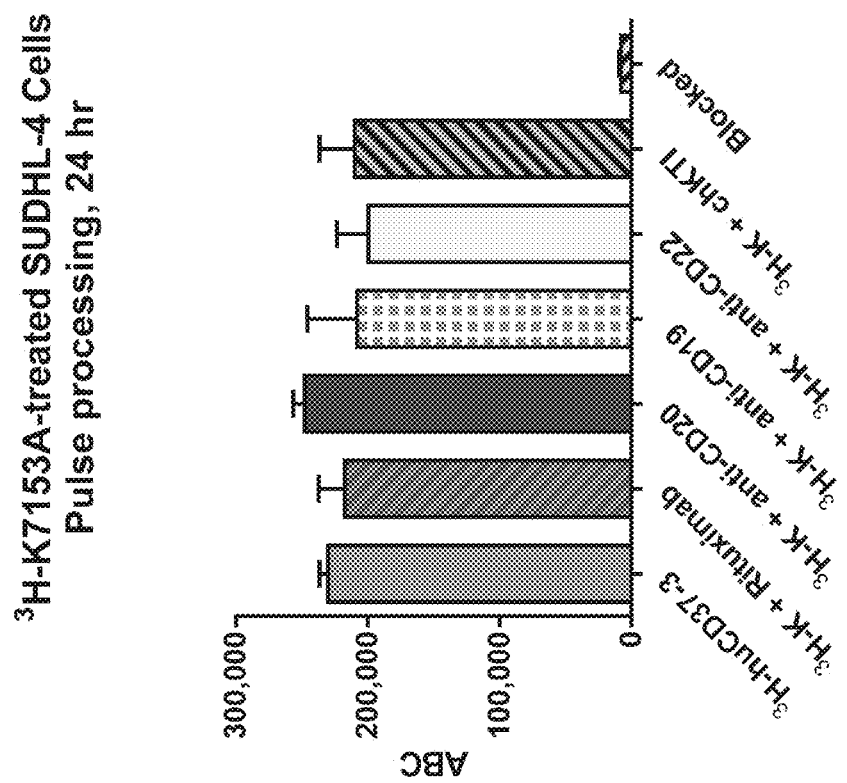
FIG. 15 shows CD37 cell surface expression (antibody bound per cell (ABC)) alone or in combination with B-cell targeting or non-targeting antibodies as measured by $^3$H-huCD37-3 treatment+/− an anti-CD19 antibody, rituximab, an anti-CD20 antibody, an anti-CD22 antibody, or non-targeting IgG antibody (chKTI) on SU-DHL-4 cells.

Upon pulse-treatment of $^3$H-huCD37-3 antibody alone or in combination with B-cell targeting or non-targeting antibody the cell surface expression of CD37 (antibody bound per cell (ABC)) remained constant. The results with SU-DHL-4 cells, of GCB sub-type is illustrated in FIG. 15. Similar results were seen with GCB subtype SU-DHL-6, Farage, DOHH2, OCI-Ly7 and ABC subtype U2932 cells. These results demonstrate that the cell surface expression of CD37, as measured by $^3$H-huCD37-3 antibody binding, remains the same during the course of the pulse-treatment regardless of co-treatment with B cell targeting or irrelevant Abs.

Figure 16:
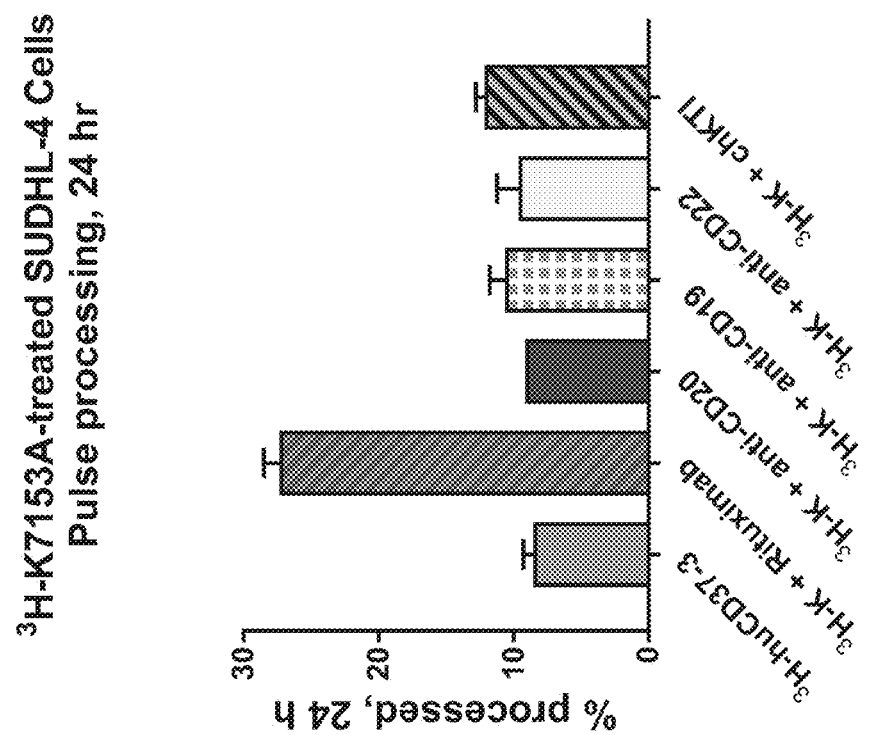
FIG. 16 shows the amount of processed $^3$H-huCD37-3 antibody with co-treatment of rituximab, B-cell targeting antibodies (CD19, CD20, CD22), or chKTI antibody.

The level of processing of $^3$H-huCD37-3 antibody whether alone or in combination with B-cell or non-targeting antibodies was determined after pulse-treatment and overnight incubation at 37° C. $^3$H-huCD37-3 antibody processing could be fully blocked by pre-treatment with a large excess of unlabeled huCD37-3 antibody. A modest 8-25% of bound $^3$H-huCD37-3 antibody was processed after 24 hr under single-agent pulse treatment, depending on the cell line tested. This level remained similar upon co-treatment with the type II anti-CD20 antibody, GA101, an anti-CD19 antibody, an anti-CD22 antibody, or chKTI Abs. However, the level increased an additional 8-21% with rituximab co-incubation in 5 of the 6 cell lines tested (OCI-Ly7, SUDHL-4, SUDHL-6, U2932, and Farage), resulting in a 1.4 to 3.4-fold increase in overall $^3$H-huCD37-3 antibody processed. In DOHH2 cells the levels of processing of $^3$H-huCD37-3 antibody alone or with rixutimab were similar: 25% and 29%, respectively. See FIG. 16 for an illustration of the processing result on SU-DHL-4 cells. These results demonstrate that the amount of receptor-bound $^3$H-huCD37-3 antibody which is internalized and degraded is increased upon co-treatment of rituximab (type 1 anti-CD20 antibody) but not upon co-treatment with other B-cell expressing antibodies or non-targeting chKTI antibody.

In order to explore whether increased processing with rituximab co-treatment was unique to CD37 antigen we ran the same series of experiments with a radiolabeled anti-CD19 specific antibody. In SU-DHL-4 cells (and observed for other cell lines, data not shown) upon pulse-treatment of the labeled anti-CD19 antibody alone or in combination with B-cell targeting or non-targeting antibodies, the surface expression of CD19 remained constant. The percent of labeled anti-CD19 antibody processed after pulse treatment remained similar upon incubation alone or in combination with GA101, huCD37-3 antibody an anti-CD22 antibody, or chKTI antibodies (data not shown). These results demonstrate that the $^3$H-huCD37-3 antibody+rituximab observations described above are specific to anti-CD37 antibody/rituximab and not anti-CD19 antibody/rituximab.

Example 11

Flow Cytometry-Based Internalization Experiments Demonstrate Increased Internalization of Anti-CD37 Antibody Upon Co-Treatment with Rituximab huCD37-3 antibody, an anti-CD19 specific antibody, and rituximab Alexa488 antibody conjugates were generated using Alexa Fluor 488 tetrafluorophenyl ester according to the manufacturer's instructions (Thermofisher). The conjugates were eluted in sodium azide free PBS, pH7.2 to enable internalization assays. The concentration and degree of labeling were calculated from absorption measurements at 280 nm and 494 nm. FACS binding assays were performed to ensure that Alexa488-labeling did not adversely affect target binding.

U2932, OCI-Ly7, SU-DHL-4, SU-DHL-6, Farage and DOHH2 cells were treated with a saturating concentration of the indicated Alexa488-labeled antibody alone or combination with unlabeled anti-CD37, anti-CD19, anti-CD20 (rituximab, ofatumumab or obinutuzumab) or the a non-binding isotype control antibody (chKTI) on ice or at 37° C. for the indicated amount of time. Cells were washed with ice-cold PBS twice, and replicate wells were resuspended in ice-cold PBS without (unquenched samples) or with 300 nM anti-A488 antibody (quenched samples). All samples were incubated for 30 m on ice. Cells were then pelleted and fix in 1% paraformaldehyde. Cells were analyzed by flow cytometry. The fluorescence of cells incubated on ice for 30 m in the presence of anti-Alexa488 antibody represents the unquenchable fluorescent fraction and was subtracted from all other samples prior to calculating internalization. Internalization was calculated as fluorescence of quenched samples corrected for incomplete surface quenching (intracellular fluorescence) divided by that of unquenched cells (total fluorescence).

To evaluate the effect of the anti-CD20 antibody, rituximab, on the internalization of IMGN529, DLBCL cell lines were incubated with Alexa488-labeled huCD37-3 antibody, the anti-CD37 targeting moiety of IMGN529, alone or in combination with rituximab or a non-targeting isotype control antibody (chKTI). At the indicated times, cells were assessed for total and intracellular fluorescence by flow cytometry. Over the course of 2 hours when incubated alone, ~18% of the total huCD37-3 antibody-Alexa488 was internalized in Farage cells (see, FIG. 17, panel A). The amount internalized remained similar when co-treated with a non-targeting control antibody (chKTI). When cells were co-incubated with huCD37-3 antibody-Alexa488 and rituximab, the internalization of huCD37-3 antibody increased to ~35% (see, FIG. 17, panel A). The increase in internalization of huCD37-3 antibody was greatest when incubated with type I (rituximab and ofatumumab) as opposed to type II (obinutuzumab) anti-CD20 antibodies (see, FIG. 17, panel A). Interestingly, there was no increase in internalization of a B-cell targeting anti-CD19 antibody in the presence of rituximab (data not shown). The increased internalization of huCD37-3 antibody was observed after 30 minutes and maintained during the course of the experiment. While treatment of cells with rituximab increased the internalization of huCD37-3 antibody, the internalization of rituximab was unchanged whether incubated alone or in the presence of huCD37-3 antibody, an anti-CD19 antibody, or a non-targeting antibody (see, FIG. 17, panel B). Similar increases in huCD37-3 antibody internalization were observed when incubated with rituximab in DLBCL-GCB subtype SU-DHL-6, Farage, DOHH2, OCI-Ly7 and the DLBCL-ABC subtype U2932 cell lines. The efficacy of IMGN529 relies on of the internalization, intracellular trafficking, and degradation of the antibody drug conjugate. The increased potency of IMGN529 and rituximab co-treatment can in part be explained by the increase in internalization of IMGN529, which likely leads to generation of higher amounts of cytotoxic catabolites.

It is to be appreciated that the Detailed Description section, and not the Summary and Abstract sections, is intended to be used to interpret the claims. The Summary and Abstract sections sets forth one or more, but not all, exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for treating a human patient having a B-cell cancer comprising administering to said patient in need thereof (i) an immunoconjugate that binds to CD37 comprising a DM1 maytansinoid, an SMCC linker, and an antibody that binds to CD37 comprising the heavy chain sequence set forth in SEQ ID NO:18 and the light chain sequence set forth in SEQ ID NO: 21; and (ii) rituximab, wherein said immunoconjugate that binds to CD37 is administered at a dose of 0.7 mg/kg once every three weeks and wherein the rituximab is administered at a dose of about 375 mg/m2 on week 1, day 1 of a three week schedule.

2. The method of claim 1, wherein the immunoconjugate that binds to CD37 and the rituximab produce a synergistic effect, with a Synergy Score of at least 4 in vitro.

3. The method of claim 1, wherein the immunoconjugate that binds to CD37 and the rituximab have a combination index value of less than 0.5.

4. The method of claim 1, wherein the cancer is leukemia or lymphoma.

5. The method of claim 1, wherein the cancer is selected from the group consisting of NHL, precursor B-cell lymphoblastic leukemia/lymphoma, B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), cutaneous follicle center lymphoma, marginal zone B-cell lymphoma, hairy cell leukemia, diffuse large B-cell lymphoma (DLBCL), Burkitt's lymphoma, plasmacytoma, plasma cell myeloma, post-transplant lymphoproliferative disorder, Waldenstrom's macroglobulinemia, acute lymphoblastic leukemia (ALL), and anaplastic large-cell lymphoma (ALCL).

6. The method of claim 1, wherein the cancer overexpresses MYC and/or BCL2.

7. The method of claim 1, wherein the immunoconjugate that binds to CD37 and the rituximab are administered intravenously.

8. The method of claim 1, further comprising administering a corticosteroid to the patient.

9. The method of claim 1, further comprising administering a growth factor to the patient.

10. The method of claim 1, wherein the human patient has relapsed diffuse large B-cell lymphoma (DLBCL).

* * * * *